United States Patent [19]
Schwartz et al.

[11] Patent Number: 5,714,481
[45] Date of Patent: Feb. 3, 1998

[54] DERIVATIVES OF 5-ANDROSTEN-17 ONES AND 5-ANDROSTAN-17-ONES

[75] Inventors: Arthur G. Schwartz, Philadelphia; John R. Williams, Merion, both of Pa.; Magid Abou-Gharbia, Wilmington, Del.; Daniel Swern, deceased, late of Elkins Park, Pa., by Ann R. Swern, Executrix; Marvin Louis Lewbart, Media, Pa.

[73] Assignee: Research Corporation Technologies, Inc., Tucson, Ariz.

[21] Appl. No.: 456,269

[22] Filed: May 31, 1995

Related U.S. Application Data

[63] Continuation of Ser. No. 49,752, Apr. 19, 1993, abandoned, which is a continuation of Ser. No. 826,349, Jan. 27, 1992, abandoned, which is a continuation of Ser. No. 615,758, Jan. 19, 1990, abandoned, which is a continuation of Ser. No. 940,677, Dec. 11, 1986, abandoned, which is a continuation-in-part of Ser. No. 762,584, Aug. 2, 1985, abandoned, which is a continuation-in-part of Ser. No. 519,550, Aug. 2, 1983, abandoned.

[51] Int. Cl.⁶ ............ A61K 31/56; C07J 9/00; C07J 11/00; C07J 13/00
[52] U.S. Cl. ............ 514/177; 514/178; 552/536; 552/624; 552/650; 552/651; 552/652
[58] Field of Search ............ 552/536, 624, 552/650, 651, 652; 514/177, 178

[56] References Cited

U.S. PATENT DOCUMENTS

| | | | |
|---|---|---|---|
| 2,833,793 | 5/1958 | Dodson et al. | 260/397.4 |
| 2,911,418 | 11/1959 | Johns et al. | 260/397.4 |
| 3,018,298 | 1/1962 | Klimstra et al. | 260/397.4 |
| 3,148,198 | 9/1964 | Goldcamp | 260/397.3 |
| 3,166,578 | 1/1965 | Klimstra et al. | 260/397.3 |
| 3,357,888 | 12/1967 | Campbell et al. | 167/65 |
| 3,391,166 | 7/1968 | Klimstra | 260/397.3 |
| 3,471,480 | 10/1969 | Fritsch et al. | 260/239.55 |
| 3,471,526 | 10/1969 | Klimstra | 260/397.4 |
| 3,580,937 | 5/1971 | Campbell et al. | 260/397.4 |
| 3,976,691 | 8/1976 | Middleton et al. | 260/544 F |
| 4,518,595 | 5/1985 | Coleman et al. | 514/178 |
| 4,628,052 | 12/1986 | Peat | 514/171 |
| 4,666,898 | 5/1987 | Coleman et al. | 514/177 |
| 4,897,390 | 1/1990 | Ruhe | 514/177 |
| 4,898,694 | 2/1990 | Schwartz et al. | 260/397.5 |
| 5,001,119 | 3/1991 | Schwartz et al. | 514/177 |
| 5,028,631 | 7/1991 | Schwartz et al. | 514/691 |
| 5,157,031 | 10/1992 | Schwartz et al. | 514/177 |

FOREIGN PATENT DOCUMENTS

| | | |
|---|---|---|
| 0 067 480 | 12/1982 | European Pat. Off. |
| 133995 | 3/1985 | European Pat. Off. |
| 2317954 | 2/1977 | France. |
| 2035738 | 7/1969 | Germany. |
| 2705917 | 8/1978 | Germany. |
| 893145 | 4/1962 | United Kingdom. |
| 989503 | 4/1965 | United Kingdom. |

OTHER PUBLICATIONS

Rao et al. Cancer Research (51), 4528–4534, Sep. 1, 1991.
Schwartz et al. Carcinogenesis, vol. 10, No. 10, 1809–1813, 1989.
Ratko et al. Cancer Research (51), 481–486, Jan. 15, 1991.
Schwartz, *Nutr Cancer*, 3, 46–53 (1981).
*Fels Ann. Report* 1979–1980 pp. 32–33.
Pashko, Chem. Abs. 101315K (1984).
Schwartz, et al., *Chem Abs.* 103, 123791m (1985).
Robinson, et al., *J. Org. Chem.* 28, 975–980 (1963).
Hanson, et al. *Perkin Transactions* I, 499–501 (1977).
Goldman, et al., *Biochimica and Biophysics Acta*, 233–249 (1973).
Pashko, et al., *Carcinogenesis*, 2, 717–721 (1981).
Abou-Gharbia et al., *Journal of Pharmaceutical Sciences*, 70, 1154 (1981).
Raineri and Levy, *Biochemistry* 9, 233–2243 (1970).
Pelc, et al., *Collection Czechoslov. Chem. Comm.*, 31, 1064 (1966).
Klimstra, et al., *Journal of Med. Chem.* 9, 924 (1966).
Bridgeman, et al., *J. Chem. Soc.*, C, 250 (1970).
Mailloux, et al., *Bulletin de la Societe Chemiau de France*, 617 (1969).

(List continued on next page.)

*Primary Examiner*—Mark L. Berch
*Assistant Examiner*—Bruck Kifle
*Attorney, Agent, or Firm*—Scully, Scott, Murphy & Presser

[57] ABSTRACT

Steroids of the formula:

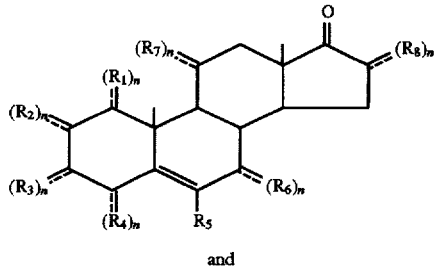

and

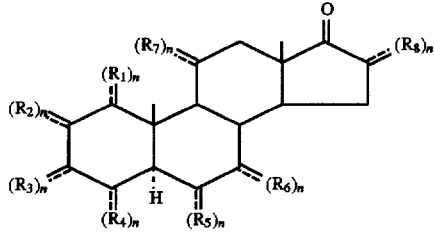

useful as cancer preventive agents, anti-obesity agents, anti-hyperglycemic agents, anti-aging agents, and anti-hypercholesterolemic agents and anti-auto-immune agents.

88 Claims, No Drawings

OTHER PUBLICATIONS

Catsoulacos, *Chemical Abstracts* 67, 54331K (1967).
Catsoulacos, et al., . *Org. Chem.*, 32, 3723–3724 (1967).
Sheppard, et al., *J.C.S. Perkins I*, 2551 (1977).
Crabb, et al., *J.C.S. Perkins I*, 1041 (1981).
Bird, *Chemical Abstracts* 92, 213616v (1980).
Geoffrey, et al., *J.C.S. Perkins I*, 750 (1980).
Kirk, et al., *J.C.S. Perkins I*, 762 (1976).
Evans, *Chemical Abstracts* 79, 42729 (1973).
Denny, et al., *J.C.S. Perkins I*, 486 (1972).
*Chemical Abstracts* 89, 105865g (1978).
Merk Index 1976, p. 376.
Numazawa, et al., *Steroids* 32, 514–527 (1978).
Pashko, et al., *Carcinogenesis* 5, #4, 463–466 (1984).
Harrison's Principle of Internal Medicine, 350, (1983).
*Chemical Abstracts* 89, 10586b (1978).
Shoppe, et al., *J.C.S.* (C) 2767 (1969).
Bird, et al., *Journal of Chemical Society*, 1979, pp. 65–66.
Jones, et al., *Journal of Chemical Society, Perkin Transactions I*, 22, 1975, 2308–2312.
Wolf et al., *J. Org. Chem.* 41, No. 7, 1976, pp. 1254–1255.
Combe, et al., *J.C.S.*, Series C, pp. 2300–2305 (1971).
Jones, et al., *J.C.S.*, Series C, 2421–2426 (1970).
Labler, et al., *Collection Czechoslov. Chem., Comm.*, 33, 2226–2237 (1967).
*Chemical Abstracts* 63, 11647–11648 (1965).
Ramseyer, et al., *Steroids*, 3347–3365 (1967).
Johnston, et al., *J.C.S.*, Series C, 1847–1856 (1966).
*Chemical Abstracts* 85, 5945b (1976).
Browne et al., *J.A.S., Perkin Transaction I*, pp. 1493–1499 (1973).
Djerassi, Carl, "Steroid Reactions", p. 199 (1963).

DERIVATIVES OF 5-ANDROSTEN-17 ONES AND 5-ANDROSTAN-17-ONES

This is a continuation of application Ser. No. 049,752, filed on Apr. 19, 1993, which is a continuation of Ser. No. 826,349 filed on Jan. 27, 1992, now abandoned which is a continuation of Ser. No. 615,758 filed on Jan. 19, 1990, now abandoned which is a continuation of Ser. No. 940,677 filed Dec. 11, 1986, now abandoned, which is a continuation-in-part of Ser. No. 762,584 filed Aug. 2, 1985, now abandoned, which is a continuation-in-part of Ser. No. 519,550 filed Aug. 2, 1983, now abandoned.

This invention described herein was made in the course of work under a grant or award sponsored in part by the National Institutes of Health.

This invention relates to novel steroids and more particularly to androsterone derivatives useful as anti-cancer, anti-obesity, anti-diabetic and hypolipidemic agents.

Dehydroepiandrosterone (DHEA) and DHEA-sulfate are major adrenal secretory products in humans. The plasma concentration of DHEA-sulfate, which next to cholesterol, is the most abundant steroid in humans, undergoes the most marked age-related decline of any known steroid.

Although DHEA-sulfate is the main precursor of placental estrogen and may be converted into active androgens in peripheral tissue, there is no obvious biological role for either DHEA or DHEA-sulfate in the normal individual. Several retrospective and prospective studies suggest that women with sub-normal levels of these steroids may be predisposed to develop breast cancer. For example, see Brownsey, et al., "Plasma dehydroepiandrosterone sulfate levels in patients with benign and malignant breast disease," Eur. J. Cancer, 8, 131–137 (1972); Bulbrook, et al., "Relation between urinary androgen and corticoid excretion and subsequent breast cancer," Lancet, 2, 395–398 (1971); Rose, et al., "Plasma dehydroepiandrosterone sulfate, androstenedione and cortisol, andurinary free cortisol excretion in breast cancer," Eur. J. Cancer, 13, 43–47 (1977); Wang, et al., "Studies of the sulfate esters of dehydroepiandorsterone and androsterone in the blood of women with breast cancer," Eur. J. Cancer, 10, 477–482 (1974); and Zumoff, et al., "Abnormal 24-hr mean plasma concentrations of dehydroisoandrosterone and dehydroisoandrosterone sulfate in women with primary operable breast cancer," Cancer Research, 41, 3360–3363, September 1981.

It has also been established that DHEA is a potent non-competitive inhibitor of mammalian glucose-6-phosphate dehydrogenase (G6PDH). For example, see Oertel, et al., "The effects of steroids on glucose-6-phosphate dehydrogenase," J. Steroid Biochem., 3, 493–496 (1972) and Marks, et al., "Inhibition of mammalian glucose-6-phosphate dehydrogenase by steroids," Proc. Nat'l Acad. Sci, U.S.A., 46, 477–452 (1960). Moreover, Yen, et al., "Prevention of obesity in $A^{vy}/a$ mice by dehydroepiandrosterone," Lipids, 12, 409–413 (1977), reported that long-term administration of DHEA to VY-$A^{vy}$/a mice prevented the development of obesity without suppressing appetite.

Furthermore, it is also known that the long-term treatment of C3H mice with DHEA, in addition to reducing weight gain without suppressing appetite, markedly inhibits spontaneous breast cancer development and may delay the rate of aging. It has been observed that DHEA antagonizes the capacity of the tumor promoter, 12-O-tetradecanoylphorbol-13-acetate, to stimulate $^3$H-thymidine incorporation in mouse epidermis and in a cultured rat kidney epithelial cell line. See, Schwartz, "Inhibition of spontaneous breast cancer formation in female C3H-$A^{vy}$/a mice by long-term treatment with dehydroepiandrosterone, Cancer Res., 39, 1129–1132 (1979); and Schwartz, et al., "Dehydroepiandrosterone: an anti-obesity and anti-carcinogenic agent," Nut. Cancer 3, 46–53 (1981).

Ben-David, et al., "Anti-hypercholesterolemic effect of dehydroepiandrosterone in rats," Proc. Soc. Expt. Biol. Med., 125, 1136–1140 (1967) have observed that DHEA treatment has an anti-hypercholesterolemic effect in mice, while Coleman, et al. (Diabetes 31, 830, 1982) report that administration of DHEA produces a marked hypoglycemic effect in C57BL/KsJ-db/db mice. The latter authors suggest that the therapeutic effect of DHEA might result from its metabolism to estrogens.

It is further known that DHEA and 16α-bromo-epiandrosterone are inhibitors of Epstein-Barr virus-induced transformation of human lymphocytes and that 16α-bromoepiandrosterone is a more potent inhibitor of mammalian G6PDH than DHEA. See, Schwartz, et al. Carcinogensis, Vol. 2 No. 7, 683–686 (1981).

While DHEA has been found effective in the afore-described manners, there is however, evidence of an estrogenic effect after prolonged administration. DHEA is not an estrogen per se but is well known to be convertible into estrogens. In addition, the therapeutic dose of DHEA is rather high. It would therefore be highly desirable to provide steroids, which while having the same afore-described advantage of DHEA are more potent and do not produce an estrogenic effect.

Besides DHEA, other steroids are known in the art.

Great Britain Patent No. 989,503 to Burn, et al. discloses 6,16β-dimethyl-3β-hydroxyandrost-5-en-17-ones. These compounds are disclosed to be useful as possessing pituitary inhibiting action.

U.S. Pat. No. 2,833,793 to Dodson, et al. discloses 1β,3β-dihydroxy-5-androsten-17-one as an androgenic and anabolic agent.

U.S. Pat. No. 2,911,418 to Johns, et al. discloses 16α-chloro-3β-hydroxyandrost-5-en-17-one and 3β-hydroxy-16α-iodoandrost-5-en-17-one as an anti-androgen.

Goldkamp, et al. in U.S. Pat. No. 3,148,198 disclose that 16α,16β-difluoro-3β-hydroxyandrost-5-en-17-one possess androgenic properties.

French Application No. FR-A 2,317,934 discloses the following compounds:

3β-hydroxy-16ξ-methylandrost-5-en-17-one

3β-hydroxy-16ξ-ethylandrost-5-en-17-one

3β-hydroxy-16ξ-isopropylandrost-5-en-17-one

U.S. Pat. No. 3,976,691 discloses the following compounds:

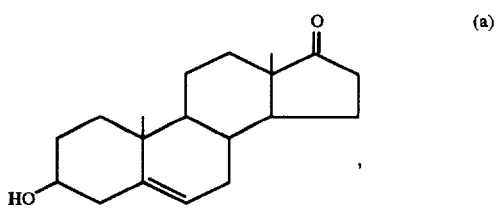

(a)

-continued

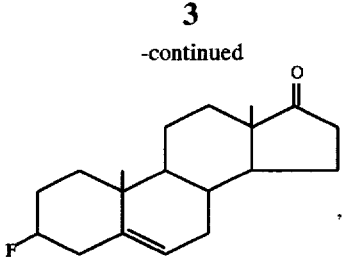

(b)

U.S. Pat. No. 3,471,480 to Fritsch, et al. discloses the following compounds which are useful as progestational agents:

(a) 3β-iodo-Δ$^5$-6-methyl-17-oxoandrostene
(b) 3β-chloro-Δ$^5$-6-methyl-17-oxoandrostene
(c) 3β-hydroxy-Δ$^5$-6-methyl-17-oxoandrostene Hanson, et al. in Perkin Transactions I, 1977, pp. 499–501, disclose 3β,4β-dihydroxyandrost-5-en-17-one. No utility is disclosed.

Chemical Abstract 89:105866b discloses that 3β-hydroxy-5α-androstan-17-one can be hydroxylated in the 15α-position. Furthermore, said reference teaches that hydroxylation of 3β-hydroxy-5αandrosten-17-one gave both the 7α and 7β-hydroxyisoandrosterones.

Numazawa, et al. in Steroids, 32, 519–527 disclose 3β,16α-dihydroxyandrost-5-en-17-one. No utility is disclosed.

DE-A- 2,035,738 discloses 7α-Methyl-3β-hydroxy-5-androsten-17-one and 6,7α-dimethyl-3β-hydroxy-5-androsten-17-one.

DE-A2 705917 discloses 3β,16β-dihydroxy-5-androsten-17-one.

The Annual Report of the Fels Research Institute, pp. 32–33, (1979–1980) discloses the following compounds as having tumor-preventive, anti-obesity and anti-aging qualities:

3β-hydroxy-16α-bromo-5α-androstan-17-one
3β-hydroxy-16α-chloro-5α-androstan-17-one
3β-hydroxy-16α-fluoro-5α-androstan-17-one
3β-hydroxy-16α-iodo-5α-androstan-17-one
3β-hydroxy-16α-bromoandrost-5-en-17-one
16αbromoandrostan-17-one Abou-Gharbia, et al. in *Journal of Pharmaceutical Sciences*, 70, 1154–1156 (1981) disclose the syntheses of:

3β-hydroxy-16α-chloro-5α-androstan-17-one,
3β-hydroxy-16α-fluoro-5α-androstan-17-one,
3β-hydroxy-16α-bromo-5α-androstan-17-one,
3β-hydroxy-16α-iodo-5α-androstan-17-one.

Pashko, et al. in *Carcinogenesis*, 2, 717–721 (1981) disclose that 16α-Br-epiandrosterone is more active than DHEA in inhibiting G6PDH and in reducing the rate of [$^3$H] thymidine incorporation into mouse breast epithilum and epidermis. The authors suggest that this compound may be useful in suppressing breast cancer development.

Neef, et al. in *J. Org. Chem*, 43, 4679–4680 (1978) disclose the syntheses of 3β-hydroxy-16α-methyl-5-androsten-17-one and 3β-hydroxy-16β-methyl-5-androsten-17-one.

Robinson, et al. in *Journal of Org. Chem.*, 28, 975–980 (1963) disclose the synthesis of 3β-hydroxy-16α,16β-difluoro-5-androsten-17-one.

Raineri, et al. in *Biochemistry*, 9, 2233–2243 (1970) tested the inhibitory activity of the following steroids on NADP and NAD linked activity of glucose 6-phosphate dehydrogenase:

3β-hydroxy-5α-androstan-17-one

3β-hydroxy-5β-androstan-17-one
3α-hydroxy-5α-androstan-17-one
11β-hydroxy-5α-androstan-17-one
3α-hydroxy-4α-methyl-5αandrostan-17-one
3α-hydroxy-7α-methyl-5αandrostan-17-one
3β-hydroxy-7α-methyl-5βandrostan-17-one
3β-hydroxy-16α-bromo-5αandrostan-17-one
3β-chloro-5α-androstan-17-one.

SUMMARY OF THE INVENTION

Accordingly, it is one object of the present invention to provide novel steroids.

It is another object of this invention to provide steroids exhibiting significant and desirable pharmacological properties.

Still another object of the present invention is to provide steroids useful as cancer preventive agents.

A further object of this invention is to provide steroids useful as anti-obesity agents.

A still further object of the present invention is to provide steroids useful as anti-hyperglycemic agents.

Another object of this invention is to provide steroids useful as anti-aging agents.

Still another object of the present invention is to provide steroids useful as anti-hypercholesterolemic agents.

A further object of this invention is to provide steroids, useful as anti-cancer, anti-obesity, anti-hyperglycemic, anti-aging and anti-hypercholesterolemic agents, and which do not evidence estrogenic effects.

An even further object of the present invention is to provide a process for the treatment and/or prevention of cancer, obesity, aging, diabetes and hyperlipidemia.

These and other objects are accomplished herein by providing novel steroids of the general formula:

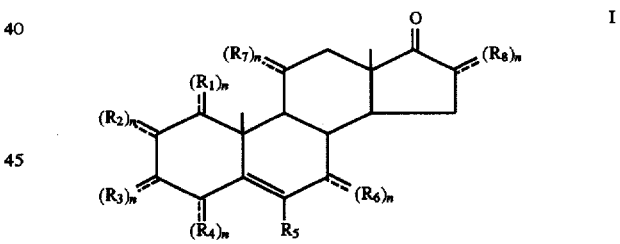

I wherein $R_1$, $R_2$, $R_3$, $R_4$, $R_6$, $R_7$ and $R_8$ are each independently selected from the group consisting of hydrogen, alkyl, alkenyl, alkynyl, halogen and hydroxyl, $R_5$ is hydrogen, alkyl, alkenyl, alkynyl or halogen, n is an integer from 1 to 2 inclusive with the proviso that when $R_1$, $R_2$, $R_3$, $R_4$, $R_5$, $R_6$, $R_7$ or $R_8$ is alkenyl or alkynyl, n is 1; and with the further provisos that at least one of $R_1$, $R_2$, $R_3$, $R_4$, $R5$, $R_6$, $R_7$ or $R_8$ is other than hydrogen; that when $R_3$ is hydroxy, any one of the substituents $R_2$, $R_4$, $R_5$, $R_6$, $R_7$ or $R_8$ is other than hydrogen and $R_1$ is other than hydrogen or hydroxy; when $R_3$ is hydroxy $R_1$ may only be alkyl when any one of $R_2$, $R_4$, $R_5$, $R_6$, $R_7$ or $R_8$ is other than hydrogen; when $R_3$ is hydroxy, $R_4$ may only be halogen or hydroxy when $R_1$, $R_2$, $R_5$, $R_6$, $R_7$ or $R_8$ is other than hydrogen; when $R_3$ is hydroxy, $R_6$ may only be hydroxy when $R_1$, $R_2$, $R_4$, $R_5$, $R_7$ or $R_8$ is other than hydrogen; when $R_3$ is hydroxy, $R_2$ may only be alkyl when one of $R_1$, $R_4$, $R_5$, $R_6$, $R_7$ or $R_8$ is other than hydrogen; when $R_3$ is hydroxy, $R_6$ can only be methyl when $R_1$, $R_2$, $R_4$, $R_7$ or $R_8$ is other than hydrogen and $R_5$ is other than hydrogen or methyl; when $R_3$ is hydroxy, $R_7$ may only be hydroxy when $R_1$, $R_2$, $R_4$, $R_5$, $R_6$ or $R_8$ is other than hydrogen; when $R_3$ is hydroxy, $R_8$ may only be methyl, ethyl, isopropyl, hydroxy or halogen when $R_1$, $R_2$, $R_4$, $R_5$, $R_6$ or $R_7$ is other than hydrogen; when $R_3$ is hydroxy, $R_5$ may only be alkyl when $R_1$, $R_2$, $R_4$ or $R_7$ is other than hydrogen and $R_6$ or $R_8$ is other than hydrogen or methyl; when $R_3$ is fluorine, any one of the substituents $R_1$, $R_2$, $R_4$, $R_5$, $R_6$, $R_7$ or $R_8$ is other than hydrogen; when $R_3$ is iodine or chlorine, $R_5$ may only be methyl when $R_1$, $R_2$, $R_4$, $R_6$, $R_7$ or $R_8$ is other than hydrogen; and when $R_3$ is hydroxy, $R_4$ may only be hydroxy when $R_1$, $R_2$, $R_5$, $R_6$ or $R_8$ is other than hydrogen.

Further objectives are accomplished herein by providing novel steroids of the formula:

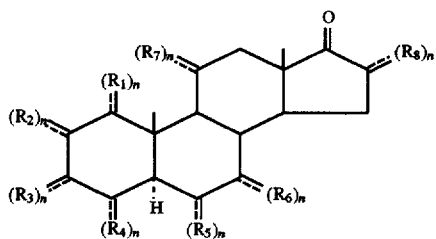

II wherein $R_1$, $R_2$, $R_3$, $R_4$, $R_6$ $R_7$ or $R_8$ are selected from the group consisting of hydrogen, alkyl, alkenyl, alkynyl, halogen and hydroxyl, $R_5$ is hydrogen, alkyl, alkenyl, alkynyl or halogen, n is an integer from 1 to 2 inclusive with the proviso that when $R_1$–$R_8$ are alkenyl or alkynyl n is 1 and with the further provisos that $R_3$ may be hydroxy or halogen only when any one of $R_1$, $R_2$, $R_4$, $R_5$, $R_6$, $R_7$ or $R_8$ is other than hydrogen; when $R_3$ is hydroxy, $R_1$ may be hydroxy or halogen only when any one of $R_2$, $R_4$, $R_5$, $R_6$, $R_7$ or $R_8$ is other than hydrogen; when $R_3$ is hydroxy, $R_2$ may be methyl or halogen only when any one of $R_4$, $R_5$, $R_6$, $R_7$ or $R_8$ is other than hydrogen; when $R_3$ is hydroxy, $R_4$ may be halogen, methyl or hydroxy only when any one of $R_1$, $R_2$, $R_3$, $R_5$, $R_6$, $R_7$ or $R_8$ is other than hydrogen; when $R_3$ is hydroxy, $R_5$ may be methyl, halogen or hydroxy only when $R_1$, $R_2$, $R_4$, $R_6$, $R_7$ or $R_8$ is other than hydrogen; when $R_3$ is hydroxy, $R_6$ may be hydroxy or methyl only when $R_1$, $R_2$, $R_4$, $R_5$, $R_7$ or $R_8$ is other than hydrogen; when $R_3$ is hydroxy, $R_7$ may be hydroxy only when $R_1$, $R_2$, $R_4$, $R_5$, $R_6$ or $R_8$ is other than hydrogen; when $R_3$ is hydroxy, $R_8$ may be methyl, hydroxy or halogen only when $R_1$, $R_2$, $R_4$, $R_5$, $R_6$ or $R_7$ is other than hydrogen; $R_7$ may be only hydroxy when any one of $R_1$, $R_2$, $R_3$, $R_4$, $R_5$, $R_6$ and $R_8$ is other than hydrogen; and $R_8$ may be bromo only when $R_1$, $R_2$, $R_3$, $R_4$, $R_5$, $R_6$ or $R_7$ is other than hydrogen.

Other objects of the invention are achieved herein by providing processes for the prophylaxis of cancer, obesity, aging, diabetes and hyperlipidemia by administering to a host, e.g. mammals, a therapeutically effective amount of the afore-identified steroids.

Additional objects are accomplished herein by providing processes for the prophylaxis of cancer, obesity, aging, diabetes, hyperlipidemia comprising administering to a host, e.g. mammals, a therapeutically effective amount of the afore-identified steroids or asteroid having the general formula:

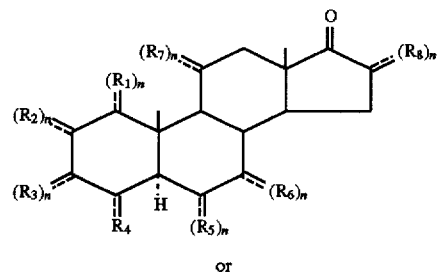

or

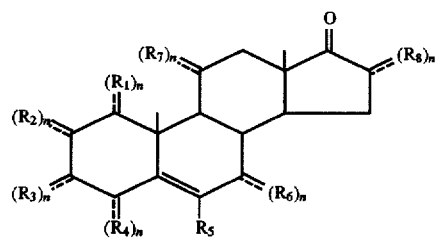

wherein $R_1$, $R_2$, $R_3$, $R_4$, $R_6$, $R_7$ and $R_8$ are selected from the group consisting of hydrogen, alkyl, alkenyl, alkynyl, halogen and hydroxyl, $R_5$ is hydrogen, alkyl, alkenyl, alkynyl or halogen, n is an integer from 1 to 2 inclusive, and with the proviso that when $R_1$–$R_8$ are alkenyl or alkynyl, n is 1. However, when with respect to the prophylaxis of cancer, obesity and aging, said compound can not be 16α-halo-3β-hydroxy-5α-androstan-17-one, 16α-Bromoandrostan-17-one or 3β-hydroxy-16α-bromoandrost-5-ene-17-one.

DETAILED DESCRIPTION OF THE INVENTION

In accordance with the present invention, it has been surprisingly discovered that steroids having a certain structure, described hereinafter in more detail, are characterized with significant pharmacological properties without toxic or undesirable estrogenic effects. That is, it has been quite unexpectedly discovered that the steroids of the present invention are useful as cancer preventive, anti-obesity, anti-diabetic, anti-aging and anti-hypercholesterolemic agents, but unlike DHEA are more potent and exhibit very little or no estrogenic effects.

More particularly, the steroids of the present invention have the general formulas:

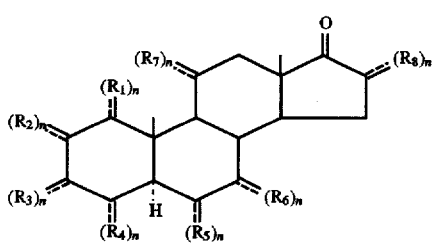

and

-continued

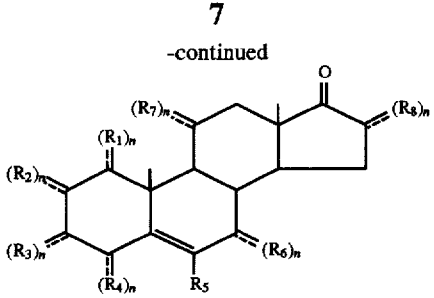

wherein $R_1$, $R_2$, $R_3$, $R_4$, $R_5$, $R_6$, $R_7$ and $R_8$ are as defined hereinbefore. The $R_1$–$R_8$ substituents are designated as being in the α-position by means of a broken line (---) joining the substituent to the steroid nucleus, the substituents are designated as being in the β-position by means of a solid line (—) joining the substituent to the steroid nucleus and in those cases in which the substituent may be either in the α- or β-position the substituents are indicated as being joined to the steroid nucleus by a broken line and a solid line placed side to side. Furthermore, in accordance with I.U.P.A.C. nomenclature, the carbon atoms of the steroids of the present invention are numbered as follows and the steroids have the designated I.U.P.A.C. stereochemistry:

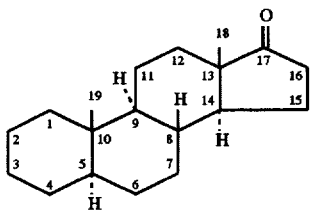

A subgenus of the novel compounds of Formula I is:

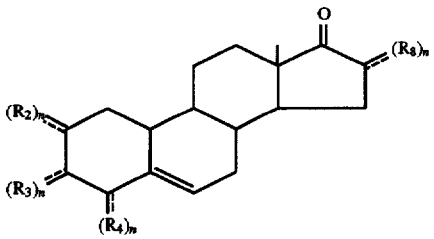

wherein $R_2$ is hydrogen or lower alkyl;

$R_3$ is hydroxy or lower alkyl;

$R_4$ is hydrogen or lower alkyl;

$R_8$ is hydrogen, halogen, hydroxy or lower alkyl; and n is 1 or 2 with the proviso that when $R_3$ is hydroxy, at least one of $R_2$, $R_4$ and $R_8$ is other than hydrogen and with the further proviso, that when $R_3$ is hydroxy and $R_2$ and $R_4$ are hydrogen, $R_8$ is other than halogen, methyl, ethyl or isopropyl.

Preferred compounds of Formula I have the following formula:

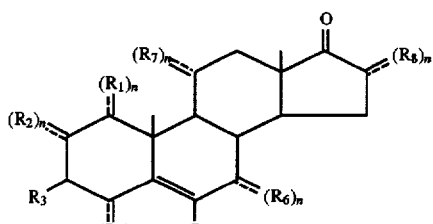

or

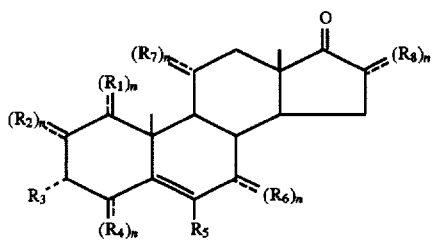

wherein $R_1$, $R_2$, $R_4$, $R_5$, $R_6$ and $R_7$ are each independently hydrogen or lower alkyl;

$R_3$ is lower alkyl;

$R_8$ is halogen, lower alkyl, hydroxy or hydrogen when it is in the α-position;

$R_8$ is lower alkyl, halogen or hydrogen when it is in the β-position; and n is 1 or 2.

In the above formulas, the preferred stereochemical configuration of carbon-16 on the steroid is depicted.

Especially preferred compounds of Formula I have the formula:

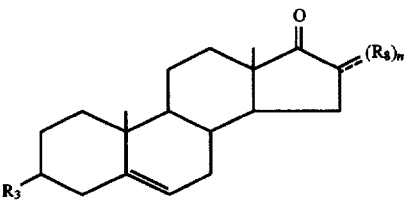

wherein $R_3$ is lower alkyl;

$R_8$ is halogen, lower alkyl, hydroxy or hydrogen when it is in the α-position;

$R_8$ is lower alkyl, halogen or hydrogen when it is in the β-position; and n is 1 or 2.

Specific illustrative compounds within the structural formula and useful in accordance with the present invention include:

3β-hydroxy-1α-methyl-5-androsten-17-one

1α-methyl-5-androsten-17-one

3β-hydroxy-2α-methyl-5-androsten-17-one

2α-ethynyl-3β-hydroxy-5-androsten-17-one

3β-hydroxy-2α,6-dimethyl-5-androsten-17-one

2α,6,16α-trimethyl-5-androsten-17-one

3β-hydroxy-2α,6,16α-trimethyl-5-androsten-17-one

3β-hydroxy-2α-ethynyl-6,16α-dimethyl-5-androsten-17-one

2α-ethynyl-6-chloro-5-androsten-17-one
3β-methyl-5-androsten-17-one
3β-ethenyl-5-androsten-17-one
3β-ethynyl-5-androsten-17-one
3β-ethynyl-6-methyl-5-androsten-17-one
3β-ethynyl-6-chloro-5-androsten-17-one
3β-ethynyl-6-chloro-16α-methyl-5-androsten-17-one
3β-ethyl-5-androsten-17-one
3β-butyl-5-androsten-17-one
3β-ethynyl-6,16α-dimethyl-5-androsten-17-one
3β,16α-diethynyl-5-androsten-17-one
3β-ethynyl-6-methyl-16α-ethyl-5-androsten-17-one
3β-ethynyl-7β-methyl-5-androsten-17-one
2α,7β-dimethyl-5-androsten-17-one
1α-chloro-3β-methyl-5-androsten-17-one
3β-hydroxy-4α-methyl-5-androsten-17-one
3β-hydroxy-4α-ethynyl-5-androsten-17-one
3β-hydroxy-4α-ethenyl-5-androsten-17-one
3β-hydroxy-16α-ethyl-4α-ethynyl-5-androsten-17-one
3β-hydroxy-16α-methyl-4α-ethynyl-5-androsten-17-one
2α,3β-dihydroxy-5-androsten-17-one
2α,3β-diethynyl-5-androsten-17-one
3β-hydroxy-4α,6-dimethyl-5-androsten-17-one
3β-methyl-4α-ethynyl-5-androsten-17-one
3β-methyl-7β-chloro-5-androsten-17-one
3β-methyl-16α-ethyl-5-androsten-17-one
3β-methyl-16α-ethynyl-5-androsten-17-one
3β-hydroxy-6-ethyl-5-androsten-17-one
3β-hydroxy-11α-methyl-5-androsten-17-one
3β-hydroxy-11α-chloro-5-androsten-17-one
3β-hydroxy-16α-methyl-5-androsten-17-one
3β-hydroxy-16α-ethyl-5-androsten-17-one
3β-hydroxy-16α-ethenyl-5-androsten-17-one
3β-hydroxy-16α-ethynyl-5-androsten-17-one
3β-hydroxy-6-ethenyl-5-androsten-17-one
3β,16α,16β-trimethyl-5-androsten-17-one
3β-methyl, 16α,16β-difluoro-5-androsten-17-one
3β-hydroxy-6-ethynyl-5-androsten-17-one
2α-methyl-3β-hydroxy-6-ethynyl-5-androsten-17-one
3β-hydroxy-7β-methyl-5-androsten-17-one
3β-hydroxy-7β-ethenyl-5-androsten-17-one
3β-hydroxy-7β-ethynyl-5-androsten, 17-one
2α-methyl-3β-hydroxy-7β-ethynyl-5-androsten-17-one
2α,3β-dimethyl-5-androsten-17-one
3β,4α-dimethyl-5-androsten-17-one
2α,3β-diethynyl-5-androsten-17-one
3β,4α-diethynyl-5-androsten-17-one
2α,3β-diethenyl-5-androsten-17-one
3β,4α-diethenyl-5-androsten-17-one
2α,3β,6-trimethyl-5-androsten-17-one
3β,4α,7β-trimethyl-5-androsten-17-one
3β-ethynyl-7β-methyl-5-androsten-17-one
6-methyl-5-androsten-17-one
7β-methyl-5-androsten-17-one
16α-bromo-3β-methyl-5-androsten-17-one
11α-methyl-5-androsten-17-one 16α-methyl-5-androsten-17-one
3β-hydroxy-4,4-difluoro-5-androsten-17-one
3β-hydroxy-16,16-difluoro-5-androsten-17-one
2α-fluoro-3β-hydroxy-5-androsten-17-one
3β-hydroxy-6-bromo-5-androsten-17-one
3β,16β-dimethyl-5-androsten-17-one
16α-hydroxy-3β-methyl-5-androsten-17-one
16α-fluoro-5-androsten-17-one
16α-fluoro-3β-methyl-5-androsten-17-one
16α-fluoro-3β,16β-dimethyl-5-androsten-17-one
16α-fluoro-16β-methyl-5-androsten-17-one The compounds of Formula I do not only possess effective therapeutic properties. These compounds are important intermediates in the formation of compounds of Formula II. Compounds of Formula II can be prepared by art recognized techniques known in organic chemistry, such as by reduction of the double bond in the β-ring of the steroid.

Preferred compounds of Formula II have the formula:

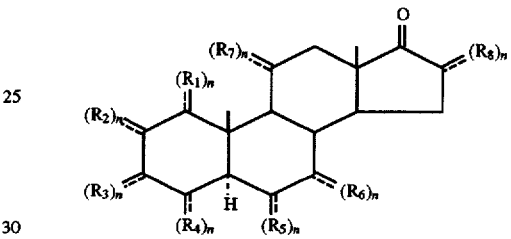

wherein
$R_1$, $R_2$, $R_4$, $R_5$, $R_6$, and $R_7$ are each independently hydrogen or lower alkyl;
$R_3$ is lower alkyl;
$R_8$ is halogen, hydroxy, hydrogen, lower alkyl, lower alkoxy when it is in the α-position;
$R_8$ is lower alkyl, halogen or hydrogen when it is in the β-position; and
n is 1 or 2.

The stereochemical configuration at carbon-16 of the steroid is specifically depicted.

The preferred compounds of Formula II are the 5α-androstan-17-one derivatives.

Especially preferred are compounds of the formula:

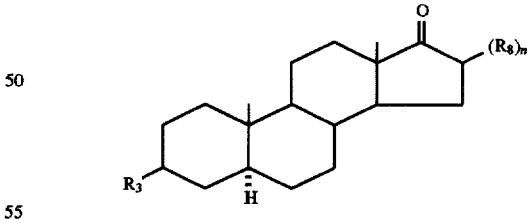

wherein
$R_3$ and $R_8$ and n are as defined hereinabove.

Specific illustrative compounds of structural Formula II and useful in accordance with the present invention include:
3β-methyl-5α-androstan-17-one
3βmethyl-4α-ethynyl-5α-androstan-17-one
3β-methyl-7β-chloro-5α-androstan-17-one
3β-methyl-16α-ethyl-5α-androstan-17-one
3β-methyl-16α-ethynyl-5α-androstan-17-one
3β-hydroxy-6-ethyl-5α-androstan-17-one 3β-hydroxy-11α-methyl-5α-androstan-17-one
3β-hydroxy-11α-chloro-5α-androstan-17-one
3β-hydroxy-16α-methyl-5α-androstan -17-one
3β-hydroxy-16α-ethyl-5α-androstan-17-one
3β-hydroxy-16α-ethynyl-5α-androstan-17-one
3β-hydroxy-6-ethenyl-5α-androstan-17-one
2α-methyl-3β-hydroxy-6-ethynyl-5α-androstan-17-one
3β-hydroxy-7β-methyl-5α-androstan-17-one
3β-hydroxy-7β-ethenyl-5α-androstan-17-one
3β-hydroxy-7β-ethynyl-5α-androstan-17-one
2α-methyl-3β-hydroxy-7β-ethynyl-5α-androstan-17-one
2α,3β-dimethyl-5α-androstan-17-one
3β,4α-dimethyl-5α-androstan-17-one
2α,3β-diethynyl-5α-androstan-17-one
3β,4α-diethynyl-5α-androstan-17-one
2α,3β-diethenyl-5α-androstan-17-one
1α-methyl-5α-androstan-17-one
3β,16β-dimethyl-5α-androstan-17-one
16α-hydroxy-3β-methyl-5α-androstan-17-one
16α-fluoro-3β-methyl-5α-androstan-17-one
16α-hydroxy-3β-methyl-5α-androstan-17-one
16α-fluoro-3β-methyl-5α-androstan-17-one
16α-fluoro-3β,16β-dimethyl-5α-androstan-17-one
16α-fluoro-3β,16β-dimethyl-5α-androstan-17-one
3β,16α,16β-trimethyl-5α-androstan-17-one
3β-methyl-16α,16β-difluoro-5α-androstan-17-one The present invention provides processes for the prophylaxis of cancer, obesity, aging, diabetes, and hyperlipidemia and autoimmune diseases, such as lupus erythematosus or Coomb's positive hemolytic anemia comprising administering to a host, e.g., mammals, a therapeutically effective amount of the present new steroids.

In accordance with the present invention, it has been surprisingly discovered that steroids having a certain structure, described hereinabove and hereinafter in more detail, are characterized with significant pharmacological properties without toxic or undesirable estrogenic effects. That is, it has been quite unexpectedly discovered that the steroids of the present invention are useful as cancer preventive, anti-obesity, anti-diabetic, anti-aging, anti-autoimmune and anti-hypercholesterolemic agents, but unlike DHEA are more potent and exhibit very little or no estrogenic effect. Furthermore, unlike DHEA compounds of the present invention do not induce liver enlargement and increased catalase activity.

In the present invention, the alkyl groups are preferably lower alkyl, which may be straight or branched chain, and which contain up to 5 carbon atoms. Examples include methyl, ethyl, propyl, isopropyl, butyl, isobutyl, pentyl, amyl and the like. The most preferred alkyl group is methyl.

The halo atoms are preferably Br, F or Cl, especially F.

Additional variations in the structural formula representing the instant compounds can be effected without significantly altering the therapeutic properties. For example, the alkyl moieties can be substituted by one or more of a variety of substituents, such as hydroxy, halogen, alkoxy and the like.

The steroids of the present invention may be prepared in accordance with conventional organic syntheses. The following procedures are illustrative of some procedures which may be utilized to prepare the steroids included herein.

For example, the steroids of the present invention can be prepared from steroids which are known or are readily available, such as dehydroepiandrosterone (DHEA), by methods of alkylation, halogenation, hydroxylation or substitution reactions known in the art. For those final products which contain both an alkyl group and a halogen or hydroxy group the various substituents may be added to the steroid in any order, but it is preferred that the alkylation step precedes the halogenation, hydroxylation or substitution step.

ALKYLATION

CARBON-1-ALKYLATION

A representative procedure for alkylation at carbon-1 and specifically the synthesis of a 1α-methyl DHEA 3a and 1α-methyl-desoxy DHEA 3b is given in Scheme 1.

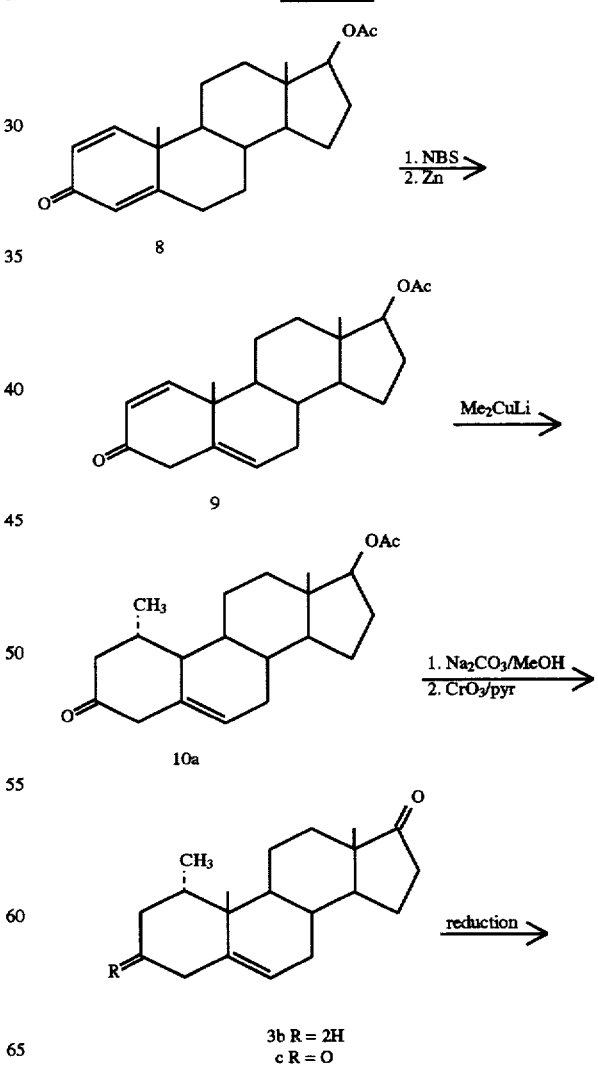

-continued
Scheme 1

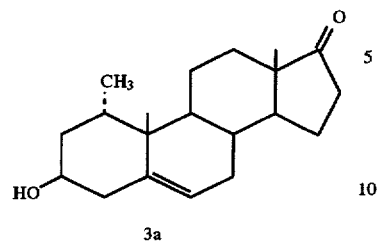

Allylic bromination (e.g. with N-bromosuccinimide (NBS)) of 17β-acetoxyandrosta-1,4-dien-3-one 8 followed by treatment with zinc affords the non-conjugated enone 9.

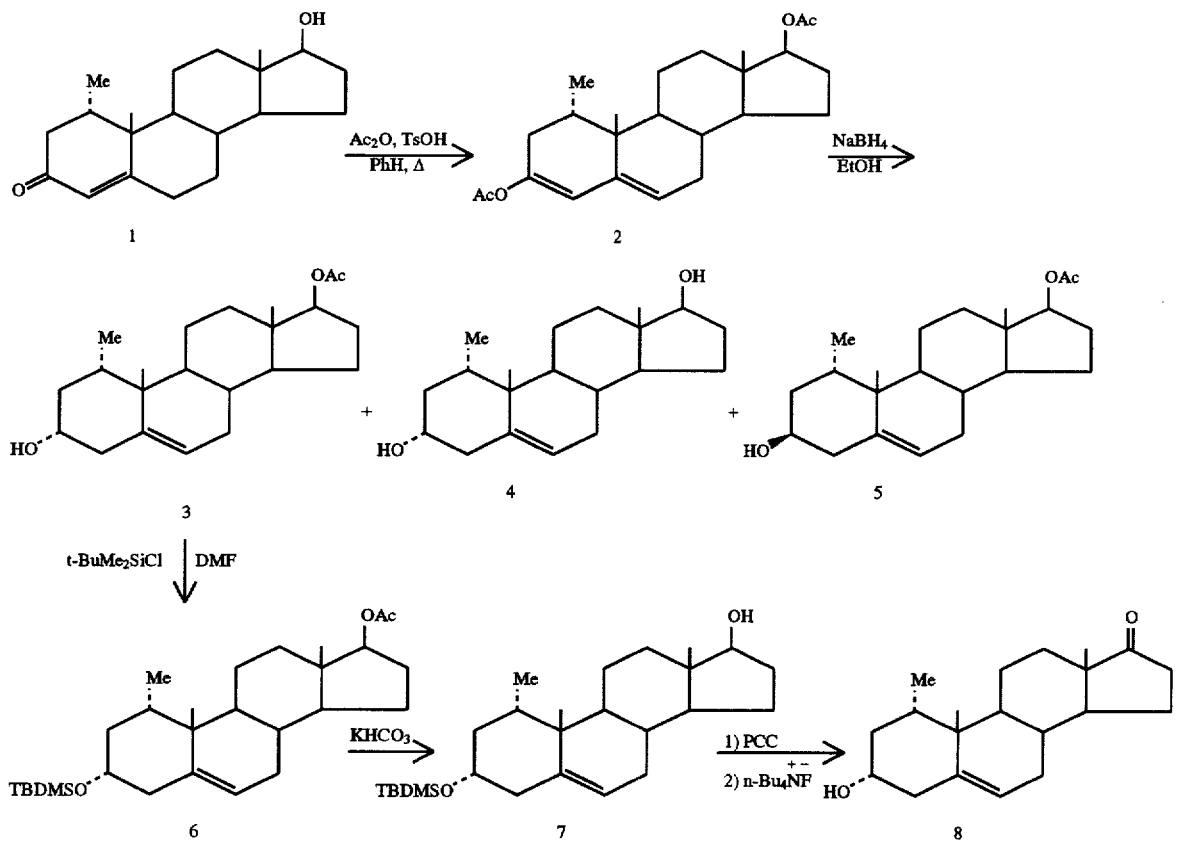

1,4-Alkylation with lithiodimethyl cuprate provides the 1α-methyl ketone 10a. At this stage the 10a may be converted to a methylene by Wolff-Kishner reduction or the Huang Minlon modification thereof. These vigorous reaction conditions result in hydrolysis of the resulting carbon-17 acetate thereby yielding the hydroxy desoxy derivative, 17β-hydroxy-1α-methylandrost-5-ene (3b). Both 10a and its desoxy derivative can be converted via standard reactions, i.e., hydrolysis of the 17-acetate with sodium carbonate and methanol followed by chromium trioxide oxidation of the resulting 17-alcohol to the carbon-17 ketone. Selective reduction of the carbon-3 ketone, 3,17-diketone 3c using sodium borohydride pyridine (pyr) yields 1α-methyl dehydroepiandrosterone 3a.

Alternatively, the 1α-methyl dehydroepiandorsterone can be synthesized according to the following procedure:

1α-methyltestosterone, 1, was reacted with acetic anhydride and p-toluenesulfonic acid in refluxing benzene, yielding the 3,5-dienol diacetate 2. Sodium borohydride reduction of 2 afforded 3α-hydroxy-17-acetate, 3 and 3α, 17β-diol 4 and a small amount of 3β-hydroxy-17-acetate 5.

The 3-hydroxy group was protected with a protecting group known in the art. For example, 3 was converted to its t-butyldimethylsilyl ether 6. Hydrolysis of 6 with a base, such as potassium, bicarbonate, in aqueous methanol afforded the 17β-hydroxy steroid 7. Pyridinium chlorochromate oxidation of the 17β-hydroxyl group followed by treatment with tetra n-butylammonium fluoride afforded the 3α-hydroxy-1α-methyl-androst-5-en-17-one.

CARBON-2-ALKYLATIONS

The following procedures are illustrative for alkylation at carbon-2 and are figuratively illustrated in Scheme 2 below.

Alkylation of testosterone (I) with an alkylating agent, such as methyl iodide, in the presence of a strong base, such as 2,2,6,6-tetramethyl lithium piperidide, lithium diethyl amide, lithium diisopropylamide (LDA), triphenylmethyl lithium, n-butyl lithium and the like gives a mixture of the 2α- and 2β-alkyl-17-β-hydroxy-4-androsten-3-one (2 and 3). Treatment of the mixture with a strong base, such as sodium methoxide in methanol, epimerizes the 2β-axial alkyl to the 2-α-equitorial configuration (2). Acetylation of 2 with an acetylating agent, such as acetic anhydride (Ac$_2$O) and p-toluenesulfonic acid (p-TSA) in toluene afforded 2α-methyl-3,17β-dihydroxy-3,5-androstadien-3,17-diacetate (4). Treatment of the diacetate (4) with sodium borohydride in 95% ethanol yielded 2α-methyl-3β,17β-dihydroxy-5-androsten-17-acetate (5). Protection of the 3-hydroxy group as a tetrahydropyranyl ether followed by hydrolysis of the 17-acetate yielded 2α-methyl-3β,17β-dihydroxy-5-androsten-3-tetrahydropyranyl ether 7. Oxidation of the C-17 hydroxy group in 7 followed by hydrolysis of the tetrahydropyranyl ether with hydrochloric acid and aqueous acetone yielded 3β-hydroxy-2α-methylandrost-5-en-17-one (9).

The following is a specific example for the synthesis of 2α-methyl DHEA.

To a solution of diisopropylamine (5.3 ml, 38 mmol) in freshly distilled tetrahydrofuran (80 ml) stirred at −78° C. was added n-butyllithium (29.3 ml of 1.3M in hexane, 38 mmol). This was stirred at −78° C. for 30 minutes then warmed to −30° and 17β-hydroxy-4-androsten-3-one (1) (5.0 g, 17.3 mmol) in tetrahydrofuran (30 ml) was added dropwise. After 30 minutes at −30° C. iodomethane (4 ml, 80 mmol) was added. The mixture was allowed to slowly warm to room temperature with stirring, then saturated ammonium chloride solution was added and the product was extracted with ether. The organic layer was dried and the solvent removed to give a mixture of isomers 2 & 3 as an oil (5.26 g) which was used in the next step.

To a stirred solution of sodium (0.75 g, 32 mmol) dissolved in methanol (100 ml) was added the epimeric mixture of 2-methyl-17β-hydroxy-4-androsten-3-one, 2 & 3 (4.93 g, 16.2 mmol) in methanol (100 ml). After 17 hours at room temperature, saturated ammonium chloride solution was added and most of the solvent was removed in vacuo. The product was extracted with dichloromethane, washed with water, dried and the solvent removed to give a gum (4.86 g) which was purified by column chromatography on silica gel. Elution with hexane ether gave 1.6 g of 2 which crystallized from methanol mp 149°–151° C.;

H$^1$ NMR (CDCl$_3$) δ5.64 (s, 1, H-4), 3.60 (t, 1, H-17, J=9 Hz), 1.24 (s, 3, H-19), 1.13 (d, 3, H-2 methyl, J=6 Hz), 0.83 (s, 3, H-18); MS m/e 302(M$^+$,33), 260(21), 246(29), 28(100).

A solution of 2α-methyl-17β-hydroxy-4-androsten-3-one (2) (4.86 g, 16.1 mmol) product mixture from the previous step in acetic anhydride (40 ml) and paratoluene sulfonic acid (200 mg) in toluene (100 ml) was refluxed 3½ hours. Pyridine (1 ml) was added, and the mixture was concentrated on a rotary evaporator, then partitioned between methylene chloride and water. The organic layer was dried and the solvent removed. The product mixture (5.78 g) was separated on a flash silica column to give 2α-methyl-3,5-androstadien-3,17βdioldiacetate (4) 1.81 g (27.4%) crystallized from Et$_2$O-hexane.mp 170°–171° C.

H$^1$ NMR(CDCl$_3$) δ 5.57 (s, 1, H-4), 5.40 (m, 1, H-6), 4.55 (t, 1, H-17, J=9 Hz), 2.08 (s, 3, 3-acetate), 2.01 (s, 3, 17-acetate), 1.06 (s, 3, H-19), 0.98 (d, 3, 2 methyl, J=6 Hz), 0.83 (s, 3, H-18); MS m/e 386(M$^+$,3) 358(12) , 43(100).

A suspension of 2α-methyl-3,5-androstadien-3,17β-dioldiacetate (4) (1.31 g, 3.4 mmol) and sodium borohydride (1.3 g) in 95% ethanol (100 ml) was stirred at room temperature for 3½ hours. The solution was cooled to 0° C. and glacial acetic acid was added, followed by saturated sodium bicarbonate solution. The product was partitioned between dichloromethane and water, the organic layer dried, and the solvent removed to give 1.23 g product mixture which was separated on 40 g of flash silica column eluted to give 5, 0.7 g from ether hexane) mp 179°–182° C.;

$^1$H NMR (CDCl$_3$) δ 5.27 (m, 1, H-6), 4.62 (t, 1, H-17, J=9 Hz), 3.03 (t, 1, H-3, J=9 Hz) 2.05 (s, 3, 17-acetate), 1.07 (s, 3, H-19), 1.02 (d, 3, 2-methyl, J=8 Hz), 0.83 (s, 3, H-18).

A solution of 2α-methyl-3β,17β-dihydroxy-5-androsten-17-acetate 5 (1.42 g, 4.1 mmol) dihydropyran (DHP) (10 ml) and paratoluene sulfonic acid (100 mg) in ether (50 ml) was stirred at room temperature for 17 hours. The ether solution was washed with saturated sodium bicarbonate solution, then water, and dried, and the solvent was removed to give the product mixture as an oil (1.65 g). The product was not purified but carried on to the next step.

2α-Methyl-3β,17β-dihydroxy-androst-5-ene-3-tetrahydropyranyl ether 17-acetate, 6, from the previous step (1.65 g, 3.84 mmol) was dissolved in a solution of 5% potassium carbonate in 4:1 methanol:water (100 ml) and refluxed 1.5 hours. Most of the solvent was removed under reduced pressure and the product was partitioned between chloroform and water. The organic layer was dried and solvent removed to give 1.45 g of the product 7 which was used in the next step.

The product mixture 7 from the previous step (1.45 g, 3.84 mmol) was dissolved in pyridine (10 ml) and added to the complex formed by mixing chromium trioxide (2 g) in pyridine (20 ml). This was stirred 2½ hours at room temperature, then 1:1 ether:benzene (30 ml) was added and the mixture was filtered through celite then silica gel. The solvent was removed to give the product mixture 8, 1.52 g as an oil, which was carried on to the next step.

A solution consisting of the product mixture 8 from the previous step (1.52 g, 3.94 mmol) and 3N HCl (2 ml) in acetone (40 ml) was stirred at room temperature for 3 hours. Saturated sodium bicarbonate solution was added and the product was extracted with dichloromethane. The organic layer was dried and the solvent removed to give 1.17 g product mixture which was separted on a flash silica column. Elution with 30:70 ether:hexane gave 3β-hydroxy-2α-methyl-androst-5-en-17-one (9) (317 g) which was crystallized from ether:hexane mp 171.5–173;

H$^1$ NMR(CDCl$_3$) δ 5.45 (m, 1, H-6), 3.10 (broad m, 1, H-3) 1.13 (s, 3, H-19), 1.07 (d, 3, 2 methyl, J=8 Hz), 0.97 (s, 3 H-18).

As stated before, the above reactions involving alkylation at carbon-2 are figuratively illustrated in Scheme 2.

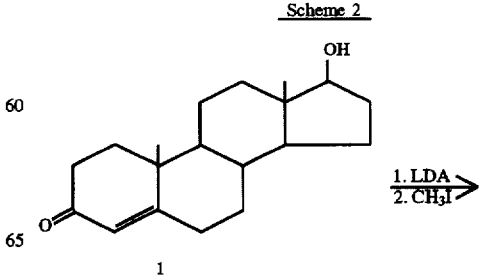

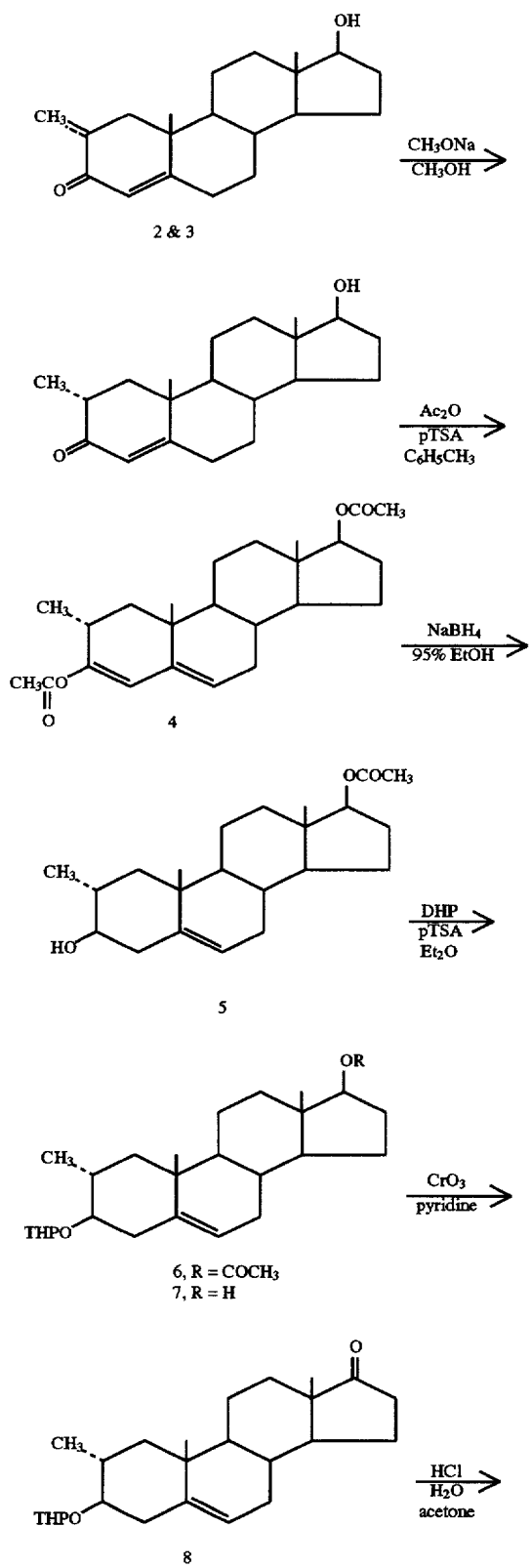

CARBON 3-ALKYLATIONS

The schematic for carbon 3-alkylations are shown figuratively in scheme 3 below.

Synthesis of dehydroepiandrosterone with a methyl group replacing the hydroxyl group at carbon-3 is shown below in scheme 3. The methyl configuration at carbon-3 is β, as determined by X-ray analysis. 3β-Hydroxy-5-androst-en-17-one (10) was iodinated at carbon-3 with O-phenylenephosphorochloridite followed by decomposition of the resulting phosphite ester with iodine. 3β-Iodoandrost-5-en-17-one (11) was ketalized, then alkylated with a mixture of methyl lithium and cuprous cyanide in tetrahydrofuran to yield 3β-methylandrost-5-en-17-ethylene ketal (13). Hydrolysis of the ketal afforded 3β-methylandrost-5-en-17-one (14)

SCHEME 3

-continued
SCHEME 3

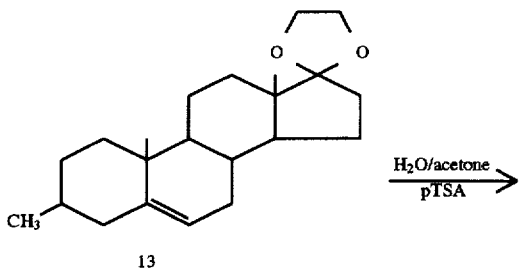

More specifically, 3β-iodoandrost-5-en-17-one (11) (11.83 g, 29.7 mmol), ethylene glycol (20 ml) and p-toluene sulfonic acid (200 mg) in benzene (250 ml) were refluxed under a Dean-Stark trap for 72 hrs. The solution was washed with saturated sodium bicarbonate, water, then dried over magnesium sulfate. Evaporation and recrystallization from ether afforded 11.5 g (87.3%) of 3β-iodocandrost-5-en-17-one-17-ethyleneketal (12): mp 140°–141° C., IR(KBr): 3010, 2940, 1470, 1425, 1375 cm$^{-1}$; $^1$H NMR (CDCl$_3$) :δ5.44 (brd J=6 Hz, 1H, H-6), 3.91 (s, 4H, ketal), 1.07 (s, $^3$H, C-19 Me), 0.88 (s, 3H, C-18 Me); MS (m/e): 442 (M$^+$, 1), 380 (35), 315 (57), 253 (67), 227 (11), 105 (24), 99 (100), 91 (35), 55 (27), 41 (33).

Cuprous cyanide (4.465 g, 49.9 mmol) was placed in a dry 500 ml 3 neck round bottom flask equipped with a magnetic stirrer. The system was flushed with N$_2$, and dry THF (30 ml) was added. The suspension was cooled to −78° C. and MeLi solution, 1.5M (66.5 ml, 99.8 mmol), was added via a syringe. The solution was allowed to warm to 0° C. for 5 min., which resulted in a clear tan solution.

After recooling to −78° C., the 3β-iodo-17-ketal (3) (7.35 g, 16.6 mmol) in 40 ml dry tetrahydrofuran was added via a syringe, and the solution was allowed to warm to room temperature and was stirred for 18 hrs. under N$_2$. The solution-was extracted with 100 ml of 90% saturated NH$_4$Cl/10% conc. NH$_4$OH. The organic layer was separated, dried over MgSO$_4$ and evaporated to give 6.69 g of crude product. Chromatography on flash silica (240 g) and elution with 1% Et$_2$O/99% hexane gave 6.41 g of colorless crystals. Recrystallization from methanol (200 ml) gave 3β-methylandrost-5-en-17-one 17-ethyleneketal, mp 121–122° C.

Anal. Calc. C 80.06, H 10.38. Found C 80.12, H 10.55

IR(KBr) 3010, 2930, 1450, 1430, 1370 cm$^{-1}$; $^1$H NMR (CDCl$_3$):δ5.33 (brd J=6 Hz, 1H, H-6), 3.90 (s, 4H, ketal), 1.03 (s, 3H, C-19 Me) 0.91 (s, $^3$H, C-18 Me); 0.97 (d, 3H, C-3 Me); MS (m/e): 330 (M$^+$, 16) 316(7), 268(29), 253(22), 239(9), 99 (100), 91(22), 55(27), 41(22).

The 3β-methylandrost-5-en-17-one 17-ethylene-ketal (1.3) (2.20 g 6.7 mmol) was dissolved in acetone (100 ml). p-Toluenesulfonic acid (100 mg) and H$_2$O (20 ml) were added and the solution was refluxed for 2 hrs. The solution was evaporated, taken up in ether (30 ml), washed with saturated NaHCO$_3$, H$_2$O, and then dried over MgSO$_4$. The solution was filtered and evaporated to give a colorless solid which was recrystallized from methanol to give 3β-methylandrost-5-en-17-one (14) as colorless plates, 1.17 g (61%) mp 148°–150° C.; IR(KBr) 3010, 2910, 1740, 1455, 1430, 1365 cm$^{-1}$; $^1$H NMR (CDCl$_3$):δ5.41 (brd, J=6 Hz, 1H, H-6), 1.11 (s, 3H, C-19 Me), 0.99 (s, 3H, C-18 Me), 1.07 (d, 3H, C-3 Me); MS (m/e) 286 (M$^+$, 58) 271(51), 229 (31) 159 (36), 105 (72), 91 (95), 79 (89), 55 (9), 41 (100).

Anal. Calc. C 83.85, H 10.55 C 83.66, H 10.65

Similarly, by using the appropriate starting materials, the following compounds were also prepared:

3β-Ethylandrost-5-en-17-one (91%)

mp 73°–75° C.; NMR (CDCl$_3$) δ 5.31 (br s, 1H, H-6), 0.99 (s, 3H, C-19 Me), 0.88 (s, 3H, C-18 Me); IR (KBr) 2910, 1735, 1435, 1365, 1010; MS 300 M$^+$, 100), 285(68), 272(85), 267(13), 257(38), 250 M* (285–267), 215(25), 203(53); Anal. Calcd for C$_{21}$H$_{32}$O; C, 83.93; H, 10.74. Found: C, 83.73; H, 10.85.

3β-n-Propylandrost-5-en-17-one (80%)

mp 103°–105° C.; NMR (CDCl$_3$) δ 5.3 (br s, 1H, H-6), 1.01 (s, 3H, C-19 Me), 0.87 (s, 3H, C-18 Me), 2.5–1.0 (m, complex); IR (KBr) 2900, 1735, 1445, 1365, 1070; MS 314 (M$^+$, 49), 299(4), 272(2), 255(37), 238(36), 229(39), 215 (15), 99(100); Anal. Calcd for C$_{22}$H$_{34}$O; C, 84.01; H, 10.89. Found: C, 83.99; H, 10.63.

3β-n-Butylandrost-5-en-17-one (82%)

mp 84°–86° C.; NMR (CDCl$_3$) δ 5.31 (br s, 1H, H-6), 0.98 (s, 3H, C-19 Me), 0.87 (s, 3H, C-18 Me), 2.5–1.0 (m, complex); IR (KBr) 2900, 1735, 1450, 1370, 1015; MS 328 (m$^+$, 8), 313(5), 272(100), 255(47), 238(15), 229(10), 215 (31), 203(45); Anal. Calcd for C$_{23}$H36O: C, 84.08; H, 11.04. Found: C, 83.96; H, 11.12.

ALKYLATION AT CARBON 4

A procedure for carbon-4 alkylation and the synthesis of 4β-methyl DHEA is given in Scheme 4.

SCHEME 4

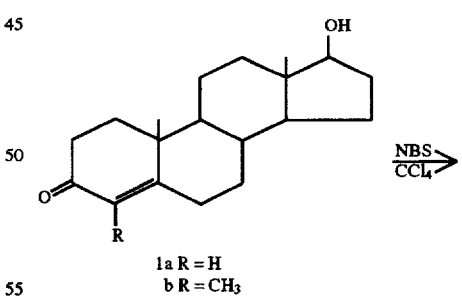

1a R = H
b R = CH$_3$

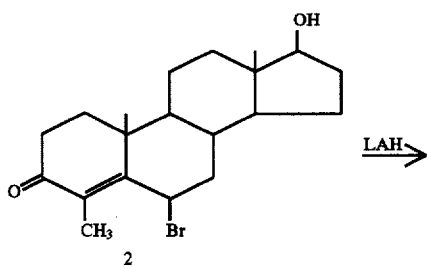

2

SCHEME 4 -continued

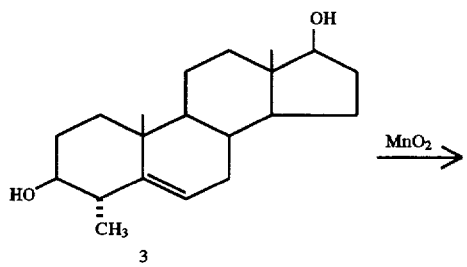

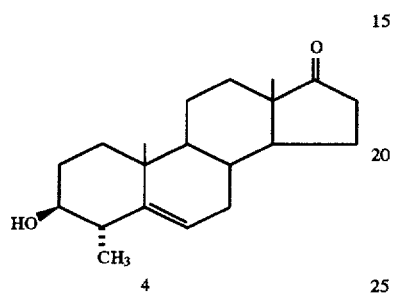

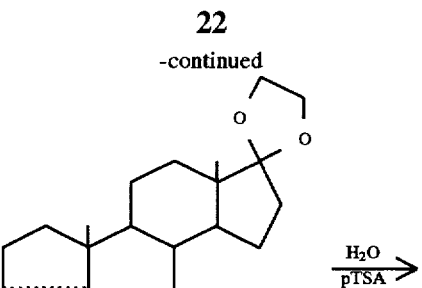

With reference to Scheme 4, alkylation of testesterone 1a using potassium t-butoxide and methyl iodide yielded 4-methyltestosterone 1b. Allylic bromination of 4-methyltestosterone using N-bromosuccinimide in carbon tetrachloride yields the 6β-bromo-4-methylandrost-4-en-17β-ol3-one 2. Lithium aluminum hydride reduction of the ketone 2 with concomitant double bond migration and loss of bromide yields 3, according to the method of Knapp and Schroepfer, *J. Org. Chem.* 1974, 39, 3247. Selective manganese dioxide oxidation of 3 affords 3β-hydroxyl-4α-methylandrost-5 en-17-one.

3α,5-Cyclosteroids such as 3α,5-cyclo-5α-androstan-6, 17-dione 17 ketal 1 are readily available by solvolysis of steroidal 5-ene-3β-tosylates and mesylates followed by oxidation of the C-6 hydroxyl group. Methylenation of 1 affords 6-methylene-3α,5-cyclo-5α-androstan-17-one 17-ketal 2 (R=H). Treatment of 2 with aqueous acid results in the addition of water and the formation of 3β-hydroxy-6-methylandrost-5-en-17-one, 3 (R=H). Alkenylated derivatives of 3 may be synthesized starting with the appropriated substituted Wittig reagent, such as $Ph_3P^{\oplus}$—$CH^{\ominus}$—$CH=CH_2$.

ALKENYLATION AND ALKYLATION AT CARBON-6

Steroids may be alkylated at carbon-6 using the method of U. Stache and W. Fritsch, *Liebigs Analen* 1966, 697, 204.

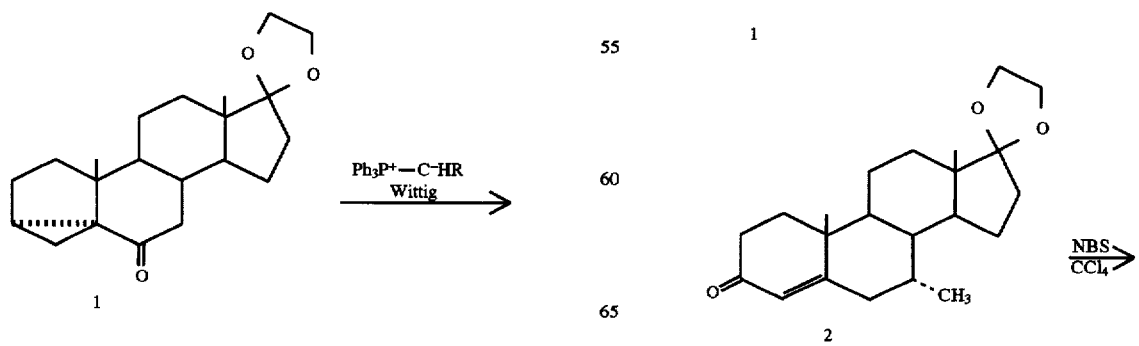

Alkylation at C-7

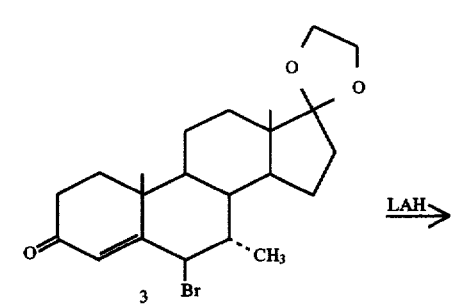

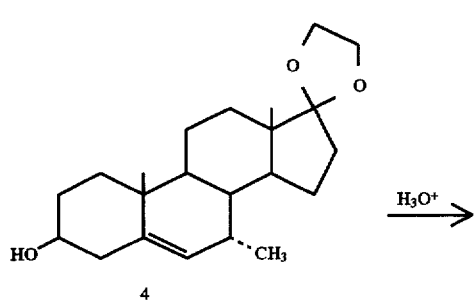

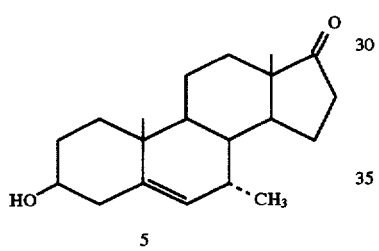

Alkylation of androsta-4,6-dien-3,17-dione 17 ketal 1 with methyl magnesium bromide in the presence of cuprous chloride, proceeds via conjugate addition to yield 7α-methylandrost-5-en-3,17-dione 17 ketal 2. Allylic bromination of 2 using N-bromosuccinimide in carbon tetrachloride yields the 6β-bromo-7α-methylandrost-4-en-3,17-dione 17 ketal 3. Lithium aluminum hydride reduction of the ketone in 3 with concomitant double bond migration and loss of bromide should yield 4. Deprotection of the C-17 ketone with aqueous acid yields 3β-hydroxy-7α-methylandrost-5-en-17-one, 5. Higher homologues may be synthesized using the substituted Grignard reagent i.e. R=CH₃, C₂H₅, C₃H₇. The 7β-epimer can be synthesized by treatment of 2 with DDQ-dichlorodicyanoquinone to generate another olefin at C-7. Catalytic reduction of this olefin should occur from the α face of the steroid to yield the 7β-methyl steroid i.e. 7β-methylandrost-5-en-3,17-dione 17 ketal. Following the same sequence as above yields 3β-hydroxy-7β-methylandrost-5-en-17-one.

Alkylation at Carbon-11

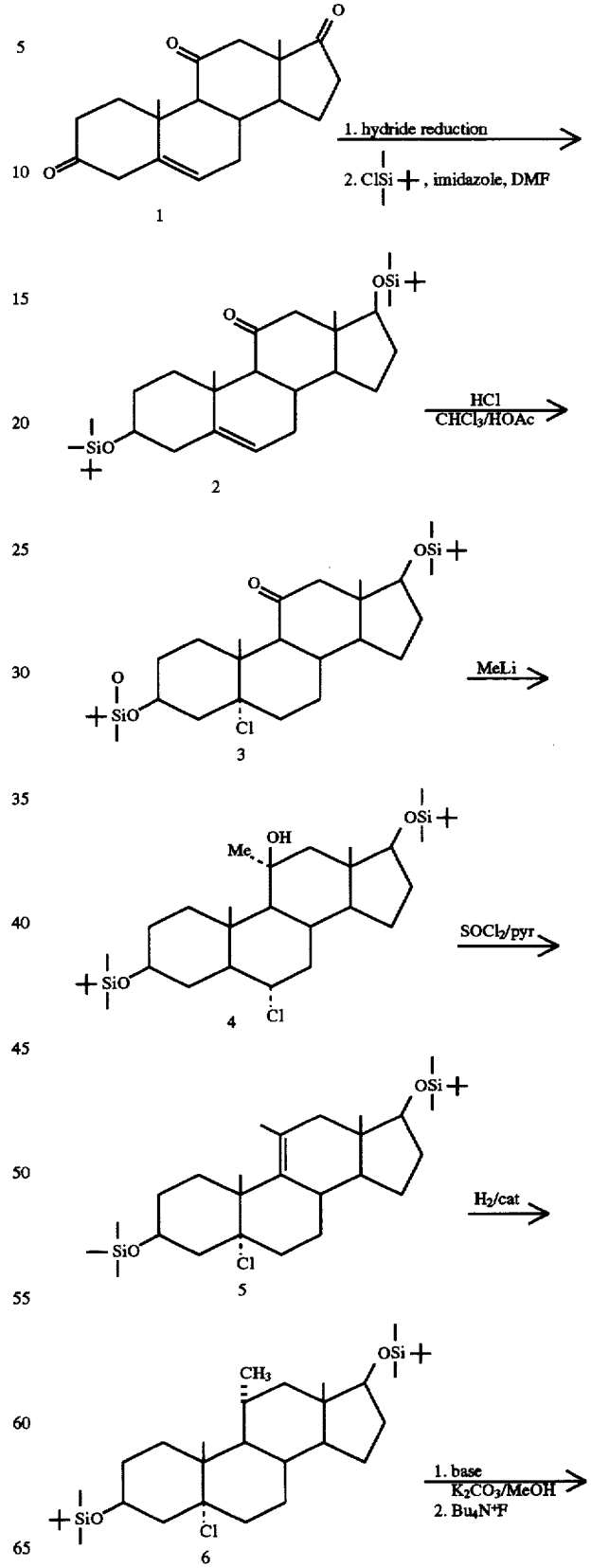

Alkylation at Carbon-11

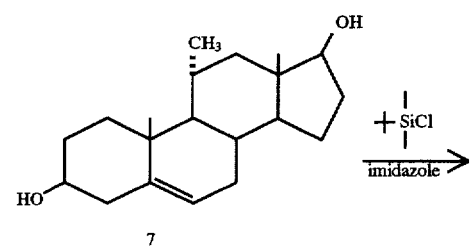

7

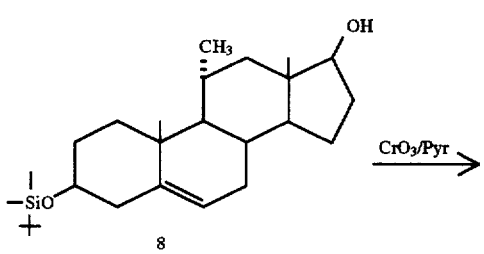

8

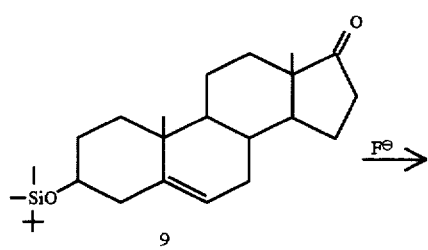

9

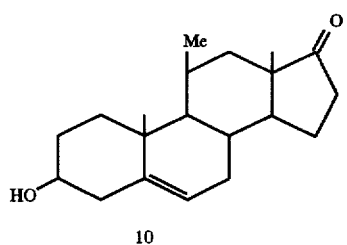

10

Due to the hindered nature of the C-11 ketone, selective reduction of androst-5-en-3,11,17-trione 1 with hydride should yield the C-3, C-17 dihydroxy steroid 2a, R=H which is protected as its bis(dimethyl-tertbutylsilyl)ether 2b R=Si (CH₃)₂t-Bu. Addition of hydrogen chloride across the C-5 olefin affords 5α-chloro-3,β,17β-dihydroxyandrost-5-en-11-one 3,17-bis(dimethyl-t-butylsilyl) ether 3. Alkylation with methyl lithium proceeds from the less hindered α face to yield 5α-chloro-11α-methylandrostan-3β,11β,17β-triol-3,17-bis(dimethyl-t-butylsilyl) ether 4. Dehydration of the methylcarbinol 4 with thionyl chloride in pyridine provides the olefin 5. Catalytic hydrogenation of 5 gives the saturated 11α-methyl-5αchloro-bis (silyl) ether 6. Treatment of the chloro silyl ether 6 with base followed by tetrabutyl ammonium fluoride affords 11α-methylandrost-5-en-3β,17β-diol 7. Selective silylation yields 11α-methylandrost-5-en-3β, 17β-diol 3-dimethyl t-butylsilyl ether 8. Oxidation of the C-17 alcohol in 8 yields 9 and deprotection of the 3-alcohol yields 11α-methylandrost-5-en-3β-ol-17-one 10. (11α-methyl DHEA).

Alkylation at Carbon-16

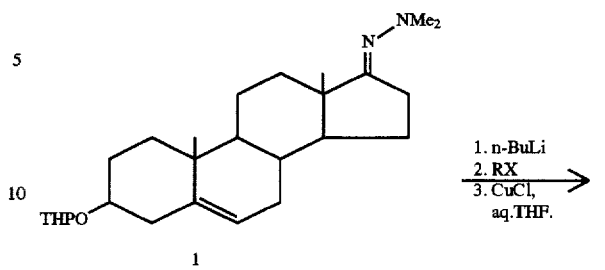

1

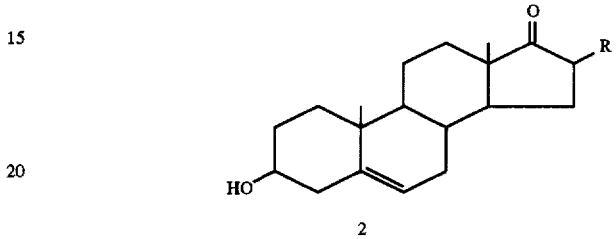

2

Alkylation of the 17-ketodimethylhydrazone of DHEA 3-tetrahydropyranyl ether using n-butyl lithium as the base followed by an alkyl halide RX, afforded the 16α-alkylated steroid. Hydrazone cleavage with cuprous chloride in aqueous tetrahydrofuran led to regeneration of the C-17 ketone and concomitant cleavage of the tetrahydropyranyl ether resulting in the 16α-alkyl-3β-hydroxy-androst-5-en-17-one 2.

The following procedure is illustrative for the preparation of 16-methyl derivatives of 3β-methyl-5-androsten-17-ones.

As shown supra, 3β-methyl-5-androsten-17-one 2 was prepared from DHEA (1).

Treatment of 2 with lithium diisopropylamide in tetrahydrofuran at −78° C. generated an enolate which was smoothly alkylated with excess methyl iodide to afford 3β,16α-dimethylandrost-5-en-17-one 3, along with small amounts of the 16β-methyl and 16,16-dimethyl derivatives 4 and 5, respectively.

SCHEME

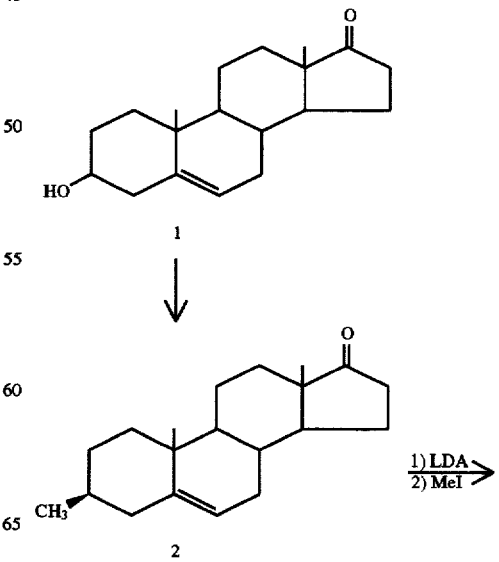

27
-continued
SCHEME

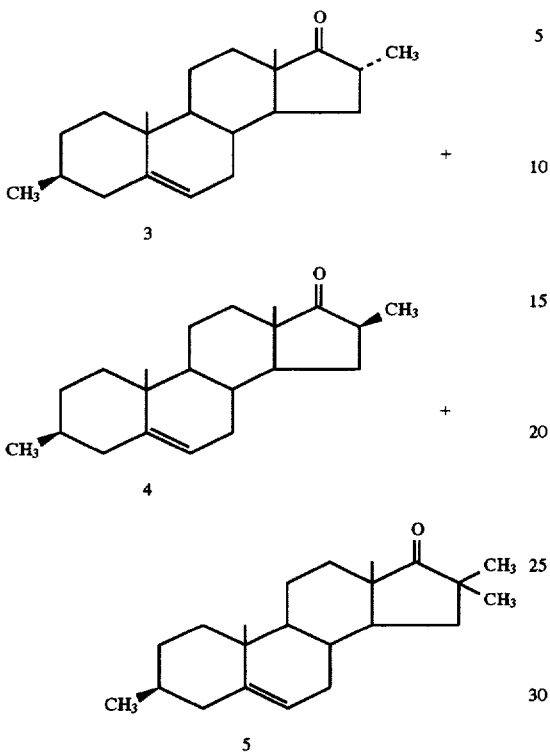

The following procedures are illustrative of alkenylation and alkynylation at Carbon-1.

Alkenylation (—CH=CHR) may be effected using the vinyl analogue of the organocuprate reagent i.e. (CHR=CH)₂CuLi as in Scheme 1 above. Alkynylation (—C≡C—R) using dialkynyl lithium cuprate is possible but this reagent is extremely sluggish. However, using a tri-n-butylstannyl ethylene which may be oxidized by lead tetraacetate to an acetylene (E. J. Corey and R. H. Wollenberg, *J. Amer. Chem. Soc.*, 1974, 96, 5581) affords a convenient method for the introduction of an acetylide group. Thus using 2-tri-n-butylstannyl ethenyl 1'-pentynyl lithium cuprate ([C₃H₇C≡C—Cu—CH=CHSn nBu₃]Li), tri-n-butylstannylethylene is added to the steroid. Oxidation using lead tetraacetate proceeds with the loss of tin and affords the corresponding acetylide. Also aluminum acetylides undergo conjugate addition to enones.

Alkenylation and Alkynylation at Carbon-2

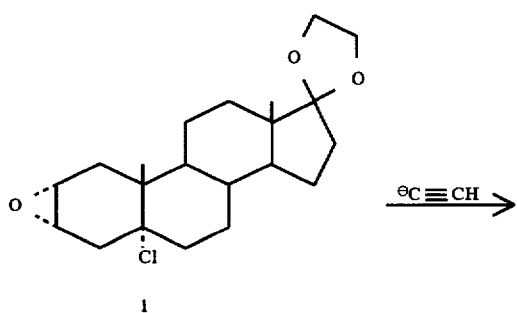

28
-continued
Alkenylation and Alkynylation at Carbon-2

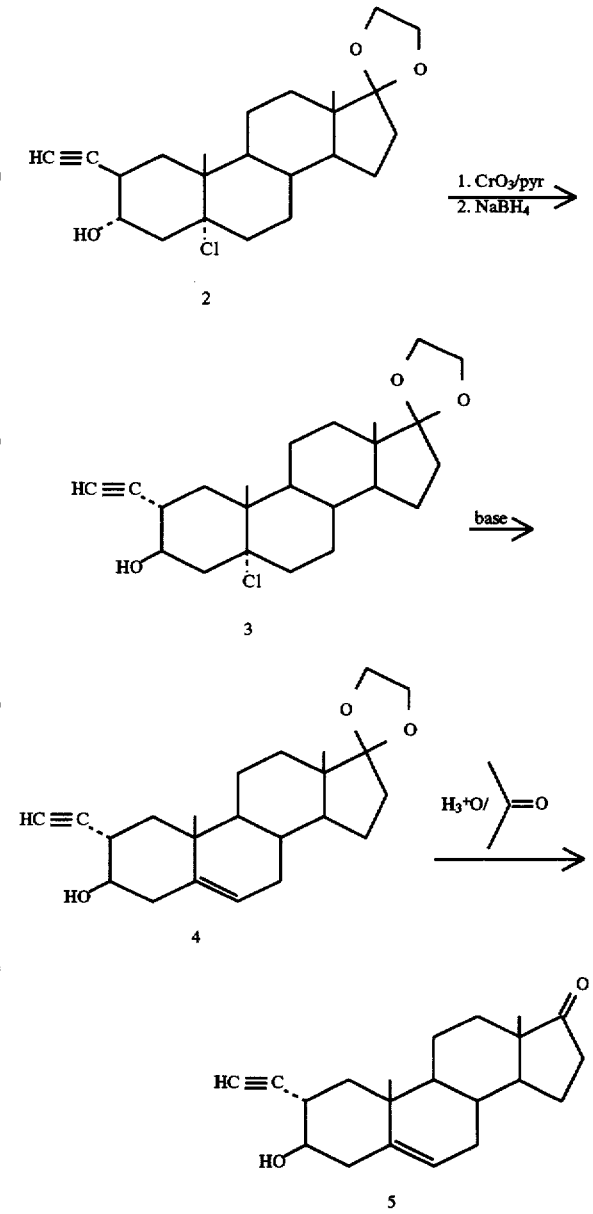

Reaction of 5α-chloro-2α,3α-epoxyandrostan-17-one 17 ketal 1 with lithium acetylide ethylene diamine complex yields 5α-chloro-2β-ethynylandrostan-3α-ol-17-one 17-ketal 2. Epimerisation of the C-3 alcohol by oxidation to the C-3 ketone (chromium trioxide/pyridine) and reduction with sodium borohydride affords 5α-chloro-2β-ethynylandrostan-3β-ol-17-one 17-ketal 3. Deprotection of the C-5 olefin and 17-ketone by treatment first with base (K₂CO₃ in methanol) followed by aqueous acid yields 2α-ethynyl-3β-hydroxyandrost-5-en-17-one 5. The 2α-ethenyl steroid can be synthesized from the ethynyl derivative by careful catalytic reduction with Lindlar catalyst to yield 2α-ethenyl-3β-hydroxyandrost-5-en-17-one.

Reaction of 3β-iodoandrost-5-en-17-one 17-ketal 1 with the organo cuprate reagent (R¹CH=CH)₂ Cu(C≡N)Li₂ generated from the appropriate vinyl lithium reagent and cuprous cyanide, should yield the 3β-alkenylandrost-5-en-17-one 2 (R=CH=CHR¹) following removal of the C-17-ketal. Similarly, reaction of 1 with the tri-n-butyl stannyl derivative R¹=nBu₃Sn yields upon oxidation with lead tetraacetate and hydrolysis of the C-17 ketal, 3β-ethynyl-androst-5-en-17-one 2 (R=C≡CH).

Reaction of 3α,4α-epoxyandrost-5-en-17-one-17-ketal 1 with lithium acetylide diethylamine complex affords 4β-ethynyl-3α-hydroxyandrost-5-en-17-one 17-ketal 2. Epimerisation of the C-3 alcohol by oxidation to the C-3 ketone with chromium trioxide/pyridine followed by reduction with sodium borohydride affords 4β-ethynyl-3, β-hydroxyandrost-5-en-17-one 17-ketal 3. Careful hydrolysis of the C-17 ketal affords 4α-ethynyl 3β-hydroxyandrost-5-en-17-one, 4.

-continued
Alkynylation at Carbon-6

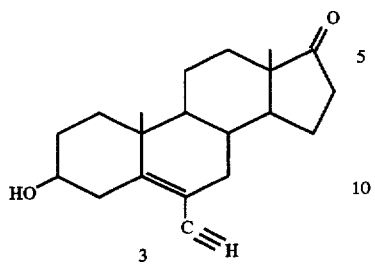

Treatment of 3α,5-cyclo-5-androstan-6,17-dione 17-ketal 1, with lithium acetylide diethyl amine complex yields 6α-ethynyl-6β-hydroxy-3α,5-cyclo-5α-androstan-17-one 17-ketal 2. Reaction of 2 with aqueous acid yields 6-ethynyl-3β-hydroxyandrost 5-en-17-one, 3.

Alkenylation and Alkynylation at Carbon-7

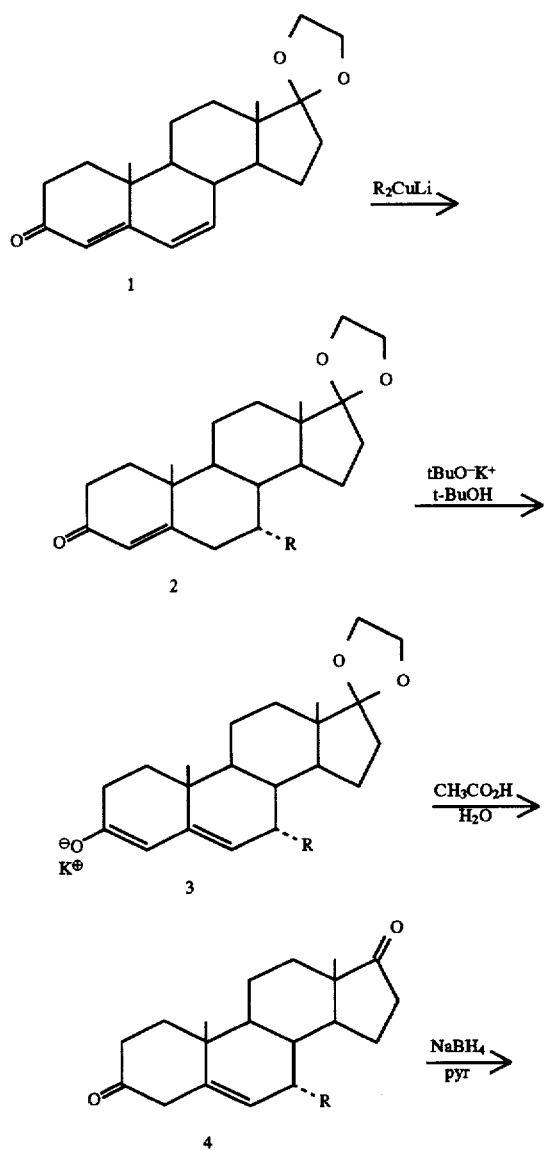

-continued
Alkenylation and Alkynylation at Carbon-7

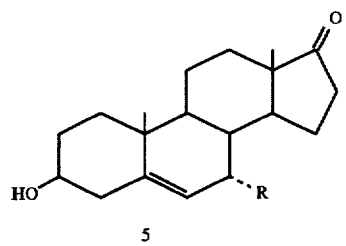

Alkenylation and alkynylation of androsta-4,6-dien-3,17-dione 17-ketal 1 with (CHR=CH)$_2$CuLi yields the 7α-alkenyl steroid 2. Treatment of 2 with potassium t-butoxide in t-butanol yields the dienolate 3 which upon protonation with acetic acid yields 7α-alkenylandrost-5-en-3,17-dione 4. Selective reduction of the C-3 ketone using sodium borohydride in pyridine yields 3β-hydroxy-7α-alkenyl-androst-5-en-17-one, 5 (R=CH=CHR$^1$). Alkynylation may be effected using 2-tri-n-butylstannyl ethenyl 1'-pentynyl lithium cuprate ([C$_3$H$_7$C≡C—Cu—CH=CHSnBu$_3$]Li), as the alkynylating reagent. The tri-n-butylstannylethylene added by this reagent is oxidized using lead tetraacetate resulting in the loss of tin and the formation of an acetylide, namely 3β-hydroxy-7α-alkynylandrost-5-en-17-one, 5 (R=C≡CH).

Alkenylation and Alkynylation at Carbon-11

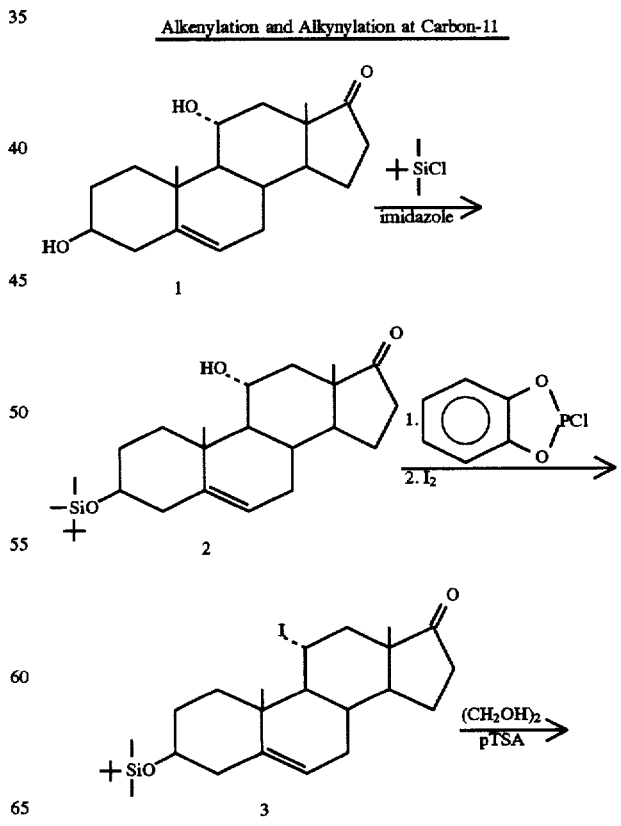

-continued
Alkenylation and Alkynylation at Carbon-11

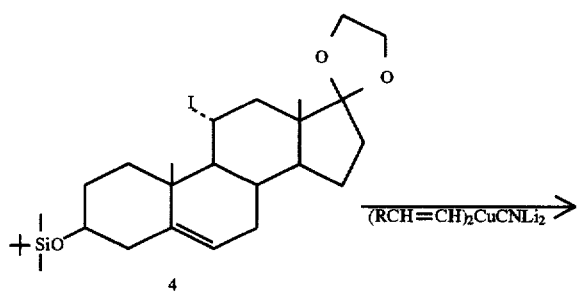

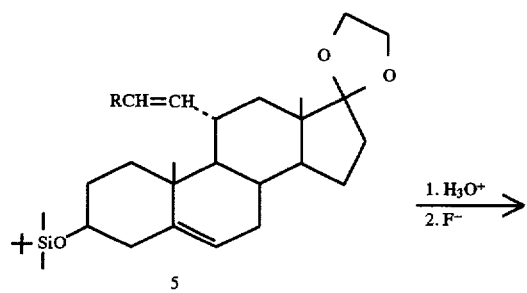

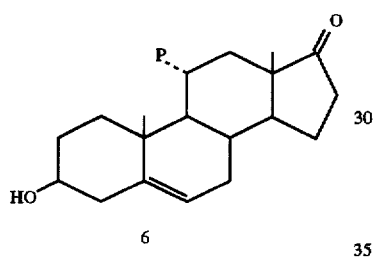

Reaction of the less hindered 3β-hydroxy of 3β,11α-dihydroxy-5-androsten-17-one 1 with t-butyldimethylsilyl chloride yields the 3β-t-butyldimethylsilyl ether 2. Treatment of this ether 2 with ortho-phenylene phosphochloridite followed by displacement with iodine yields 3β-hydroxy-11α-iodoandrost-5-en-17-one dimethyl-t-butylsilyl ether 3. Protection of the C-17 ketone as the 1,3-dioxolane 4 followed by alkenylation using dialkenyl dillthio cyano cuprate, (RCH=CH)₂ CuCNLi₂ yields 11α-alkenyl-3β-hydroxyandrost-5-en-17-one t-butyldimethylsilyl ether 5. Depcotection of the C-17 ketone and 3βalcohol affords 11α-alkenyl 3β-hydroxylandrost-5-en-17-one 6. If 6 has R=2'-tri-n-butylstannyl ethenyl then lead tetraacetate oxidation affords 11α-alkynyl 3β-hydroxyandrost-5-en-17-one, 6, (R=C≡CH).

Alkynylation and Alkenylation at Carbon-16

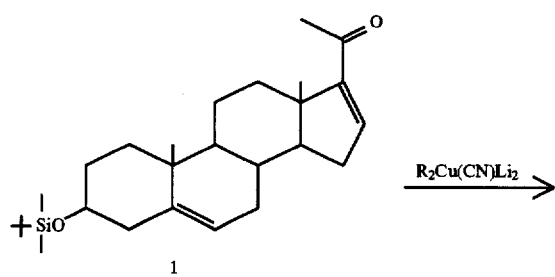

-continued
Alkynylation and Alkenylation at Carbon-16

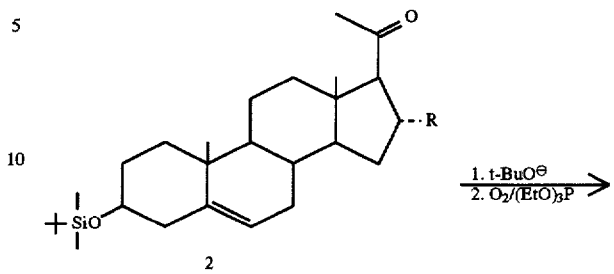

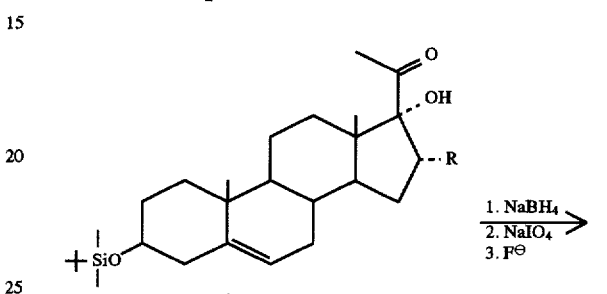

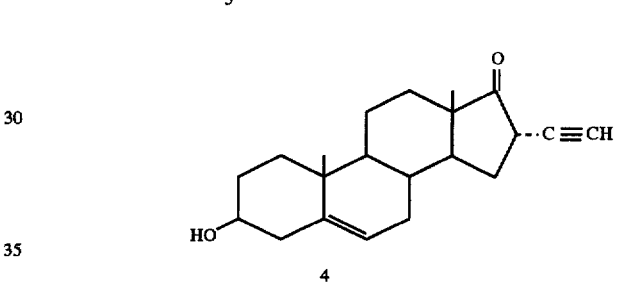

Michael addition of a suitably substituted organo copper reagent such as 2-tri-n-butylstannyl ethenyl 1'-pentynyl lithium cuprate ([C₃H₇C≡C—Cu—CH=CH Sn nBu₃]Li) to 3β-hydroxypregna-5,16-dien-20-one 3-t-butyl dimethylsilyl ether 1 yields a 16α-tri-n-butylstannyl ethylene (2, R=CH=CHSn nBu₃). Lead tetraacetate oxidation proceeds with the loss of tin and yields the corresponding acetylide. Treatment of 2 with t-butoxide followed by oxygen to generate a C-16α-hydroperoxide which is reduced by triethylphosphite to 16α-ethynyl-3β,17α-dihydroxy-pregn-5-en-20-one 3-t-butyldimethylsilyl ether 3. Reduction of the C-20 ketone to an alcohol followed by cleavage of the diol with sodium periodate and deprotection of the 3β-hydroxyl group with fluoride, yields 16α-ethynyl-3β-hydroxyandrost-5-en-17-one, 4. Careful reduction of the acetylene in 4 should afford the 16α-vinyl substituted steroids. Higher homologues of these substituents may be synthesized via similar routes.

The following procedures illustrate hydroxylation at Carbon-1, 2, 4, 7, 11 or 16.

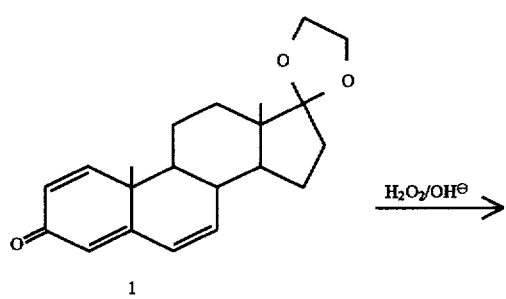

1

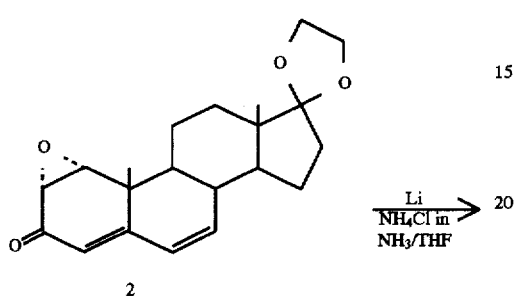

2

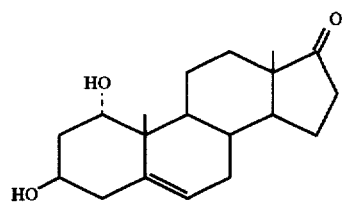

Dodson, R. M., Goldkamp, A. M., and Muir, R. D., *JACS*, 1957, 79, 3921.

Dodson, R. M., Goldkamp, A. M., and Muir, R. D., *JACS*, 1960, 82, 4026.

Penicillium hydroxylates DHEA at C-1 in the α-position. Therefore, other substrates that look like DHEA should by hydroxylated at C-1 by this enzyme.

C-2 Hydroxylation

2α,3β-dihydroxyandrost-5-en-17-one

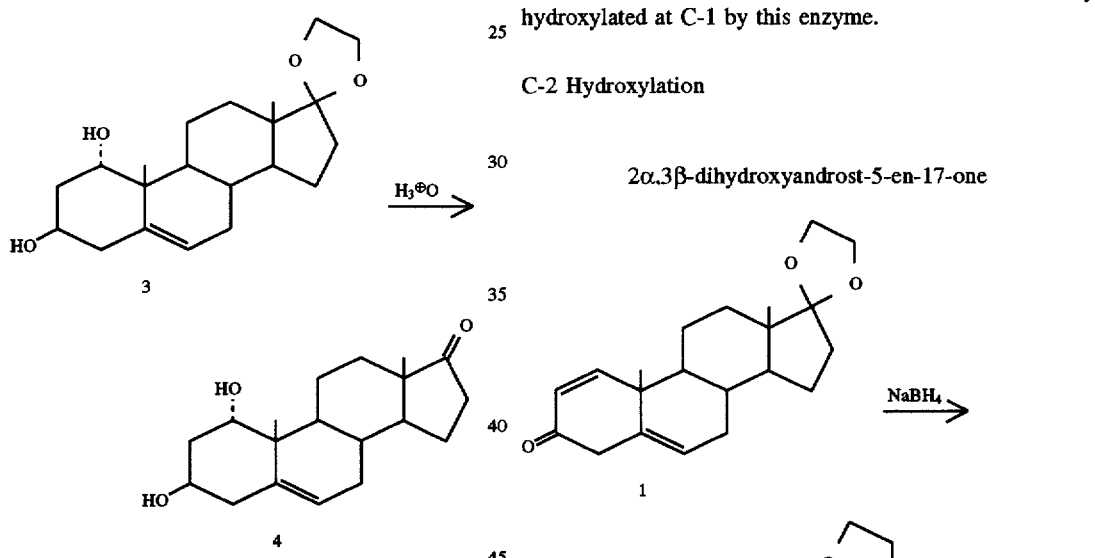

Alkaline hydrogen peroxide epoxidation of androsta-1,4, 6-triene-3,17-dione 17-ketal 1 with basic hydrogen peroxide yields the 1α,2α-epoxide 2. Treatment of 1α,2α-epoxyandrosta-4,6-dien-3,17-dione 17-ketal 2 with a large excess each of lithium metal and ammonium chloride in ammonia-tetrahydrofuran (1:1) under reflux leads to 1α,3β-dihydroxyandrost-5-en-17-one 17-ketal 3. Hydrolysis of the ketal affords 1α,3β-dihydroxyandrost-5-en-17-one, 4. Also, fermentation of DHEA with *penicillium aspergillus* affords 4, i.e. *penicillium aspergillus* may be able to 1α-hydroxylate other substrates.

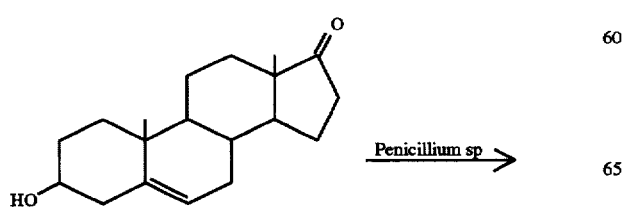

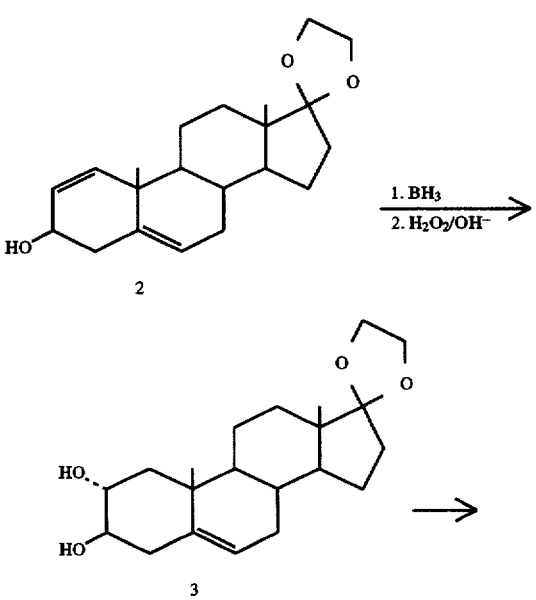

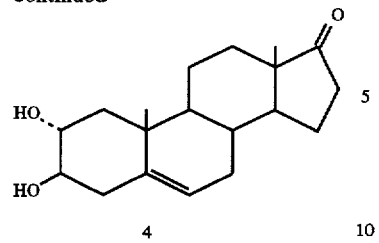

Reduction of androsta-1,5-dien-3,17-dione-17-ketal 1 with sodium borohydride yields 3β-hydroxyandrosta-1,5-diene-17-one 17-ketal 2. Hydroxylation of the C-1 double bond by hydroboration followed by oxidation with alkaline hydrogen peroxide affords 2α,3β-dihydroxy-androst-5-en-17-one 17-ketal 3. Deprotection of the C-17 ketone with aqueous acid yields 2α,3β-dihydroxy-androst-5-en-17-one, 4.

Carbon-4 Hydroxylation

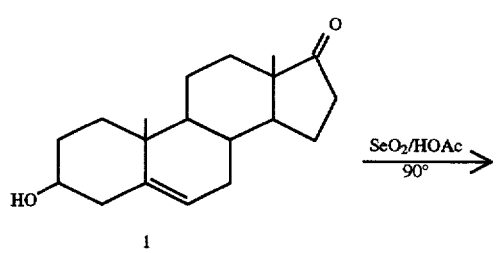

Selenium dioxide oxidation of 3β-hydroxyandrost-5-en-17-one yields 3β,4β-dihydroxyandrost-5-en-17-one 2. The axial C-4 alcohol may be epimerized to the equatorial position by reaction with sodium ethoxide in ethanol to yield 3β,4α-dihydroxyandrost-5-en-17-one, 3.

Carbon-7 Hydroxylation

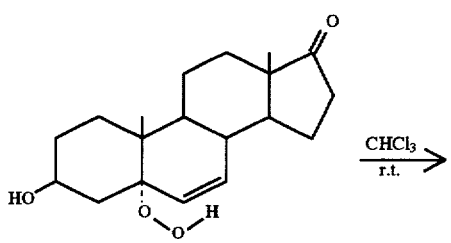

3β-Hydroxyandrost-5-en-17-one (DHEA) 1 reacts with singlet oxygen to yield 5α-hydroperoxy-3β-hydroxy-androst-6-en-17-one 2. This hydroperoxide undergoes a rearrangement when in chloroform solution to yield 7α-hydroperoxy-3β-hydroxyandrost-5-en-17-one, 3. Treatment of the hydroperoxide with zinc and acetic acid yields 3β,7α-dihydroxy-androst-5-en-17-one, 4.

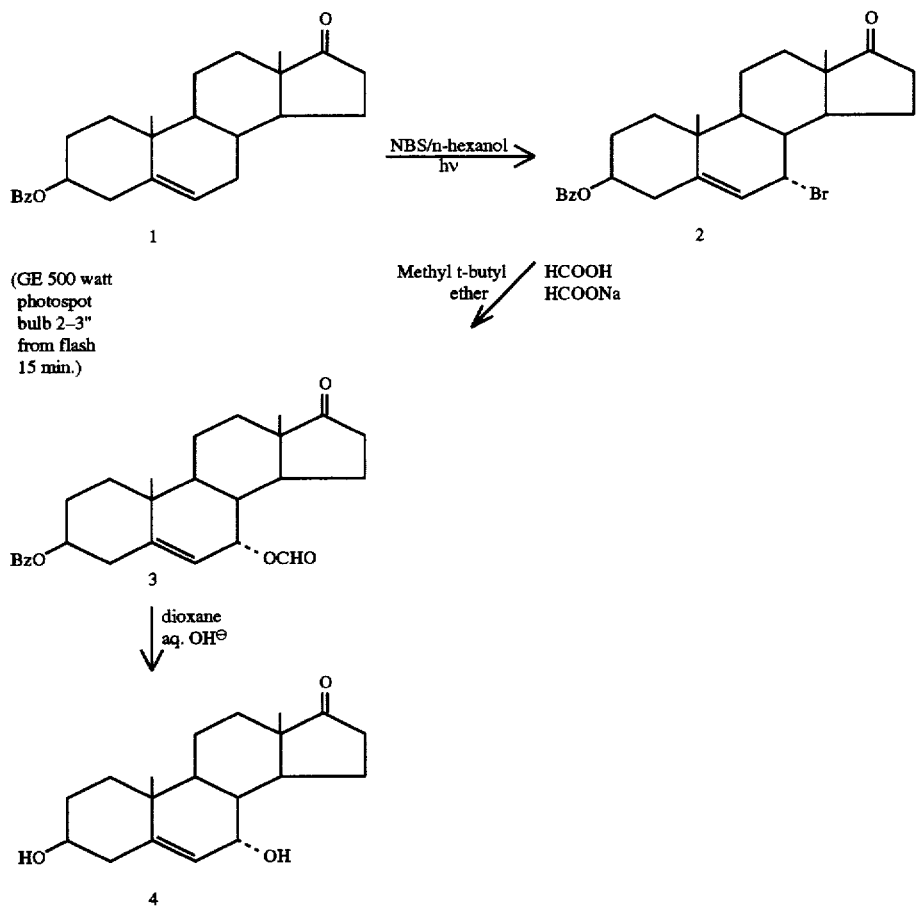

Alternatively, irradiation for approximately 15 minutes of 3β-benzyloxy-5-androsten-17-one 1 in the presence of NBS produces the 7-αBromo-3β-benzyloxy-5-androsten-17-one 2. The light source is provided by a G.E. 500 watt photospot bulb, which is placed 2-3" from the flask. Reaction of 2 with sodium formate and formic acid in the presence of methyl t-butyl ether produces the formate ester 3. Substitution with aqueous base, such as OH⁻, results in the 3β,7α-dihydroxy-5-androsten-17-one 4 .

Carbon-11 Hydroxylation

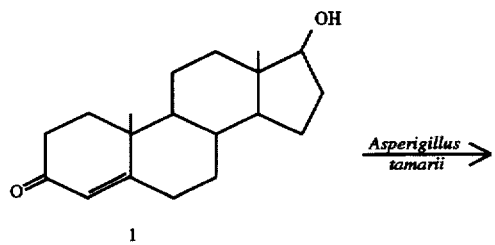

-continued
Carbon-11 Hydroxylation

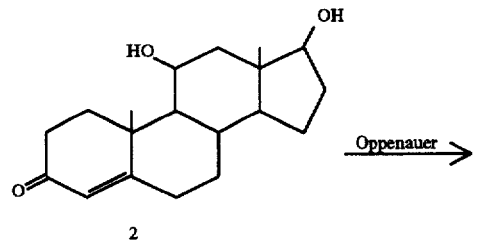

D. R. Brannon, J. Martin, A. C. Ochlschlager, N. N. Durham, and L. H. Zalkow, J. Org. Chem. 1965. 30, 760.

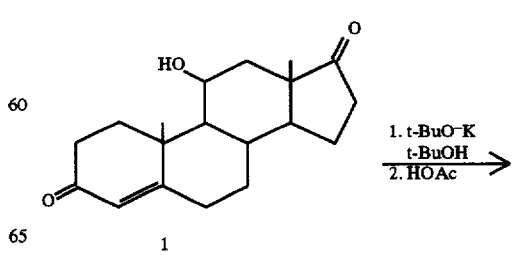

41
-continued

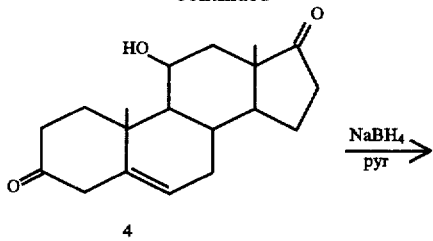
4

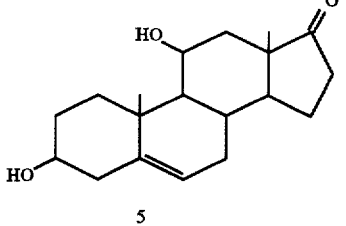
5

Hydroxylation of testosterone 1 at Carbon-11 using *Aspergillus tamarii* affords 11β,17β-dihydroxyandrost-4-en-3-one 2. Oppenauer oxidation of 2 oxidizes the 17β-alcohol in the presence of the hindered 11β-hydroxyl group to yield 11β-hydroxyandrost-4-en-3,17-dione, 3. Migration of the double bond out of conjunction by treatment with potassium t-butoxide followed by protonation with acetic acid yields 11β-hydroxyandrost-5-en-3,17-dione 4. Selective reduction of 4 yields 3β,11β-dihydroxyandrost-5-en-17-one, 5.

Hydroxylation at Carbon-16

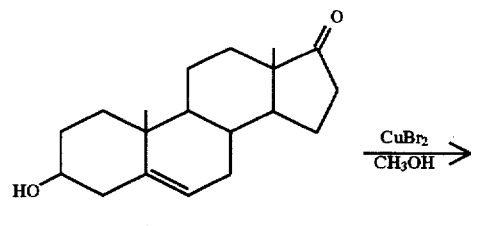
1

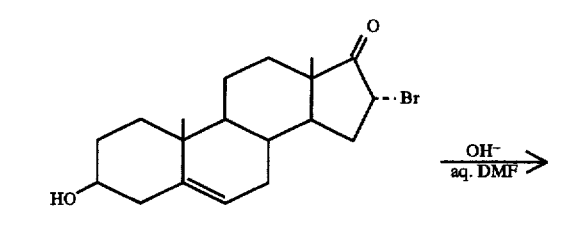
2

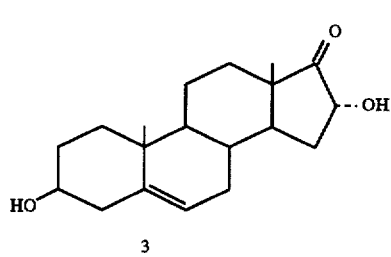
3

Bromination of DHEA (1) with cupric bromide yields 16α-bromo-DHEA, 2. Treatment of the bromo ketone 2 with sodium hydroxide in aqueous dimethylformamide gave 3β,16α-dihydroxyandrost-5-en-17-one, 3. See M. Numazawa, M. Nagaoka, Y. Osawa, J. Org. Chem. 1982, 47, 4024.

42

The following procedures are representative of procedures for halogenation at Carbon-1, 2, 3, 4, 6, 7, 11 or 16.

Halogenation at Carbon-1

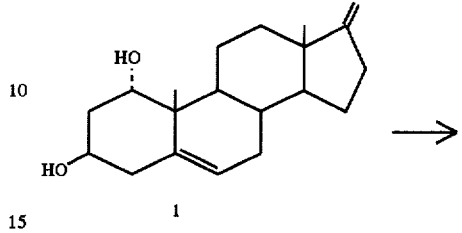
1

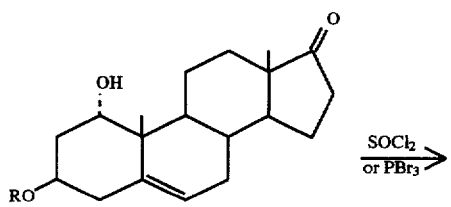
2

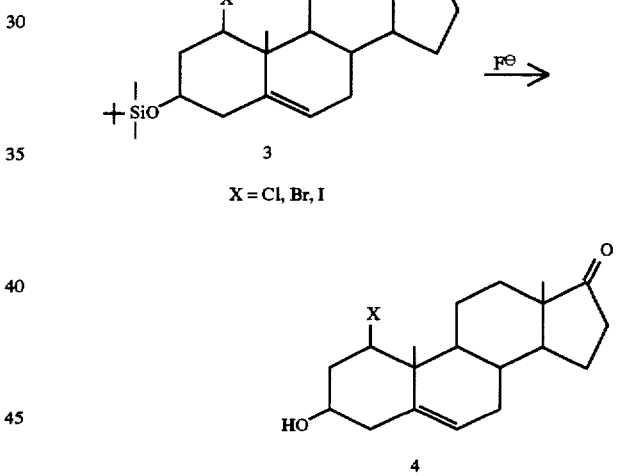
3

X = Cl, Br, I

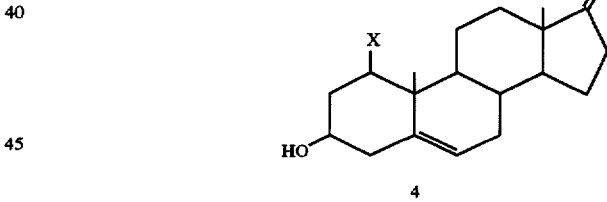
4

Selective protection of the Carbon-3 hydroxyl in the presence of the 1α-hydroxyl group should yield 2. For example, 1α,3β-dihydroxyandrost-5-en-17-one 1 reacts with t-butyl-dimethyl silyl chloride in the presence of imidazole using dimethylformamide as a solvent to yield 1α,3β-dihydroxyandrost-5-en-17-one 3t-butyldimethylsilyl ether, 2. Reaction of 2 with thionyl chloride, or phosphorous tribromide or catechol phosphochloridate followed by iodine yields the corresponding 1β-chloro, bromo or iodo derivatives 3. Reaction of 3 (R=Cl, Br, I) with tetrabutyl ammonium fluoride yields 1β-halo-3β-hydroxy androst 5-en-17-one, 4 (R=Cl, Br or I). The fluoride (4, R=F) may be synthesized via a similar route using an ester as the protecting group at C-3 and reacting the 1α-hydroxyl group with diethyl (2-chloro-1,1,2-trifluoroethyl)amine. Hydrolysis should yield 1β-fluoro-3β-hydroxyandrost-5-en-17-one, 4, R=F.

Halogenation at Carbon-2

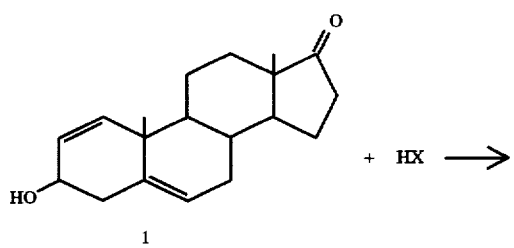

Addition of HX across the C-1 double bond in 3β-hydroxyandrosta-1,5-diene-17-one, 1, yields a mixture of the C-1 and C-2 halogenated steroids. Separation affords 2-halo-3β-hydroxyandrost-5-en-17-one (2, R=F, Cl, Br, I).

Halogentation at Carbon-3

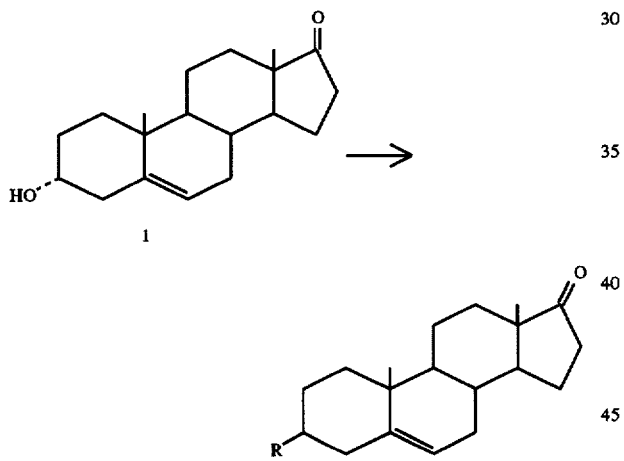

2a R = F
b R = Cl
c R = Br
d R = I

Reaction of 3β-hydroxyandrost-5-en-17-one 1 with diethyl (2-chloro-1,1,2-trifluoroethyl)amine yields 3β-fluoroandrost-5-en-17-one 1. Reaction of 1 with thionyl chloride yields 3β-chloroandrost-5-en-17-one, 2b. Reaction of 1 with phosphorus tribromide yields 3β-bromoandrost-5-en-17-one, 2c. Reaction of 1 with catechol phosphochloridate followed by iodine yields 3β-iodoandrost-5-en-17-one 2d.

Halogenation at Carbon-4

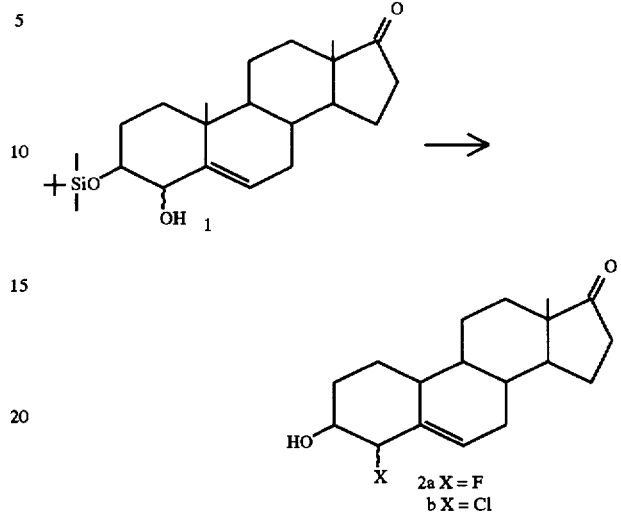

2a X = F
b X = Cl
c X = Br
d X = I

With the 3β-hydroxyl group protected as its t-butyldimethylsilyl ether the C-4 hydroxyl may be chlorinated using thionyl chloride. Treatment with fluoride ion cleaves the silyl ether to yield 4ξ-chloro-3β-hydroxyandrost-5-en-17-one, 2b. Reaction of 3,4-dihydroxyandrost-5-en-17-one 3-t-butyldimethylsilyl ether 1 with O-phenylene phosphochloridite, followed by displacement with bromide ion and cleavage of the silyl ether with fluoride ion yields 4ξ-bromo-3β-hydroxyandrost-5-en-17-one, 2c. Reaction of 1 with catechol phosphochloridate, followed by iodine and cleavage of the silyl ether with fluoride yields 4ξ-iodo-3β-hydroxyandrost-5-en-17-one, 2d. Fluorination of 3β,4ξ-dihydroxyandrost-5-en-17-one 3-acetate with diethyl (2-chloro-1,1,2-trifluoroethyl)amine followed by hydrolysis of the ester yields 4ξ-fluoro-3β-hydroxyandrost-5-en-17-one, 2a.

Halogenation at Carbon-6

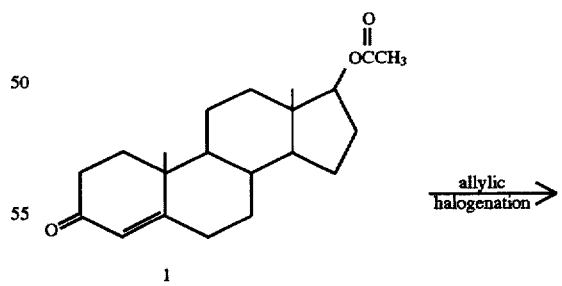

allylic halogenation →

Halogenation at Carbon-6

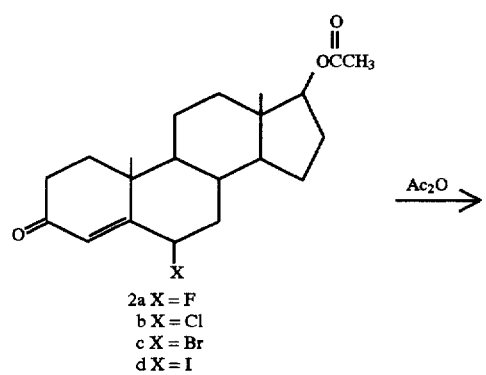

2a X = F
b X = Cl
c X = Br
d X = I

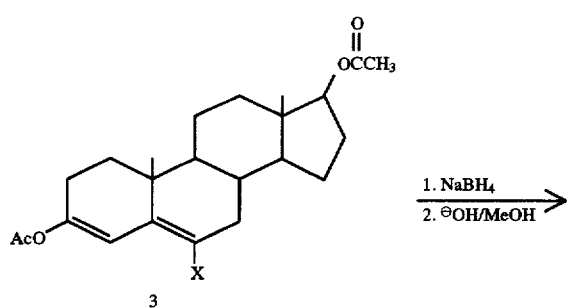

3

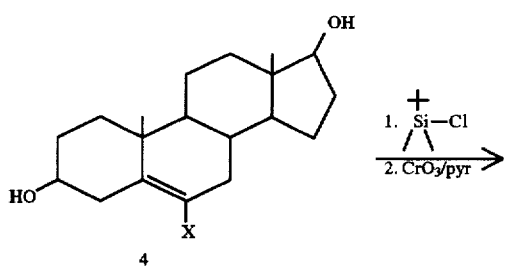

4

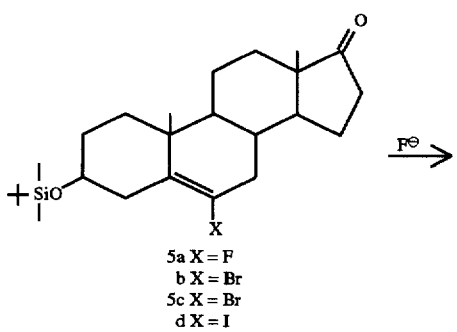

5a X = F
b X = Br
5c X = Br
d X = I

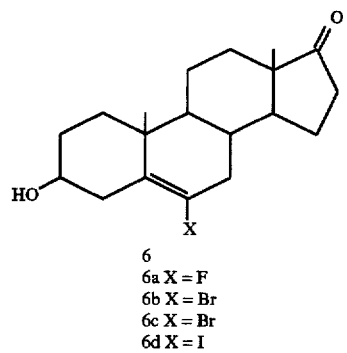

6
6a X = F
6b X = Br
6c X = Br
6d X = I

Allylic bromination of 17β-hydroxyandrost-4-en-3-one 17-acetate 1 using N-bromosuccinimide together with a radical initiator such as light or benzoyl peroxides or aliphatic azo compounds [RR'C(CN)—N=N—C(CN)RR'] e.g. azobisisobutyronitrile yields 6β-bromo-17β-hydroxyandrost-4-en-3-one 17-acetate, 2. Allylic chlorination of 1 using sulfuryl chloride together with a radical initiator such as light or benzoyl peroxide or aliphatic azo compounds yields 6β-chloro-17β-hydroxyandrost-4-en-3-one 17-acetate, 2c. Allylic iodination of 1 using mercuric iodide and light yields 6β-iodo-17β-hydroxyandrost-4-en-3-one-17-acetate, 2. Acetylation of 2 with acetic anhydride and p-toluene sulfonic acid in toluene yields 6-halo-3,17β-dihydroxyandrosta-3,5-diene 3,17-diacetate 3. Sodium borohydride reduction of 3 followed by basic hydrolysis of the C-17 acetate yields 6-haloandrost-5-en-3β,17β-diol, 4. Selective protection of the C-3 hydroxyl group as its t-butyldimethylsilyl ether followed by chromium trioxide oxidation of the C-17-hydroxyl group yields 6-halo-3β-hydroxyandrost-5-en-17-one 3-t-butyldimethylsilyl ether 5. Treatment of 5 with fluoride ion yields 6-halo-3β-hydroxyandrost-5-en-17-one, 6. The C-6 fluoro analogue may be synthesized from the C-6 bromo diacetate, 3c, by treatment with silver fluoride. Following the above sequence, reaction of 6-fluoro-3,17β-dihydroxyandrosta-3β-diene-3,17-diacetate, 3a with sodium borohydride yields, 6-fluoro-3β-hydroxyandrost-5-en-17-one, 6a.

Halogenation at Carbon-7

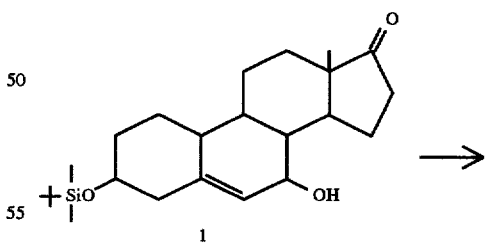

1

Halogenation at Carbon-7

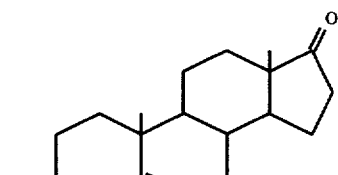

2a X = F
b X = Cl
c X = Br
d X = I

Reaction of 3β,7-dihydroxyandrost-5-en-17-one-3-t-butyldimethylsilyl ether 1 with thionyl chloride yields the C-7 chloro-steroid. Deprotection of the 3β-hydroxyl group affords 7-chloro-3β-hydroxyandrost-5-en-17-one, 2b. Reaction of 1 with catechol phosphochloridate followed by displacement with bromide ion and deprotection yields 7-bromo-3β-hydroxyandrost-5-en-17-one, 2c. Similarly reaction of 1 with catechol phosphochloridate followed by displacement with iodine and deprotection yields 7-iodo-3β-hydroxyandrost-5-en-17-one, 2d. Fluorination of 3β,7-dihydroxyandrost-5-en-17-one 3-acetate with diethyl (2-chloro-1,1,2-trifluoro-ethyl)amine followed by hydrolysis of the ester yields 7-fluoro-3β-hydroxyandrost-5-en-17-one, 2a.

Halogenation at Carbon-11

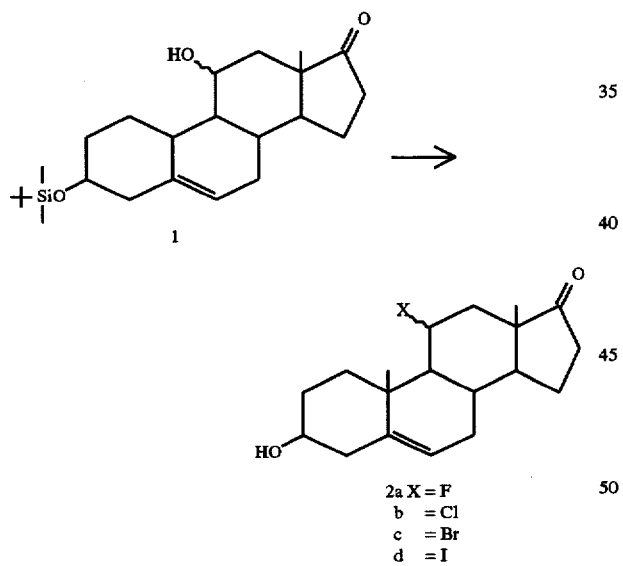

2a X = F
b = Cl
c = Br
d = I

Reaction of 3β,11α-dihydroxyandrost-5-en-17-one 3-t-butyldimethylsilyl ether 1 with OPPC followed by chloride yields the C-11 chloro steroid. Deprotection of the 3β-hydroxyl group affords 11ξ-chloro-3β-hydroxyandrost-5-en-17-one, 2b. Reaction of 1 with OPPC followed by displacement with bromide ion and deprotection yields 11ξ-bromo-3β-hydroxy-androst-5-en-17-one, 2c. Similarly reaction of 1 with OPPC followed by displacement with iodine and deprotection yields 11ξ-iodo-3β,hydroxyandrost-5-en-17-one 2d. Fluorination of 3β,11α-dihydroxyandrost-5-en-17-one 3-acetate with diethyl (2-chloro-1,1,2-trifluoroethyl)amine followed by hydrolysis of the ester yields 11ξ-fluoro-3β-hydroxy-androst-5-en-17-one, 2a.

Halogenation at Carbon-16

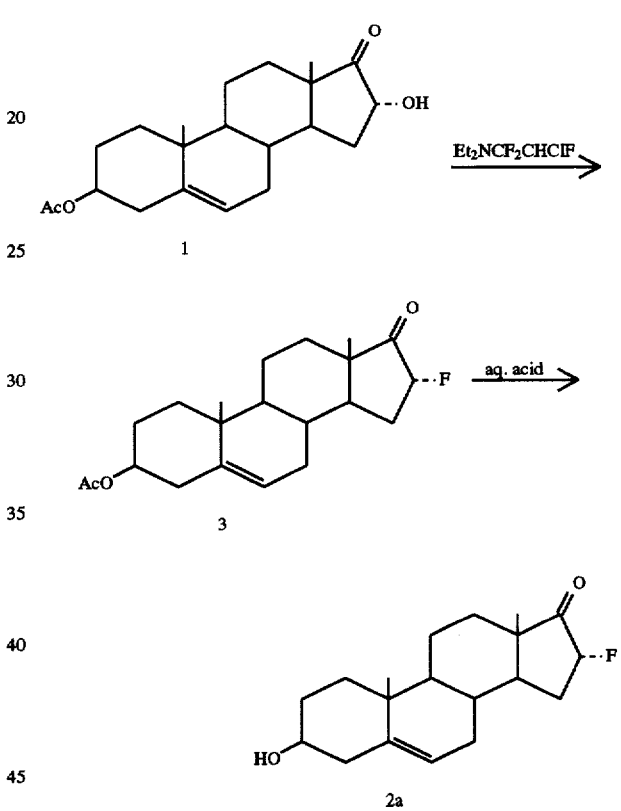

Reaction of 3β,16α-dihydroxyandrost-5-en-17-one 3β-acetate 1 with a fluorinating agent such as diethyl (2-chloro-1,1,2-trifluoroethyl)amine affords 16α-fluoro-3β-hydroxyandrost-5-en-17-one 3-acetate 3. Hydrolysis of the ester with aqueous acid yields 16α-fluoro-3β-hydroxyandrost-5-en-17-one, 2a.

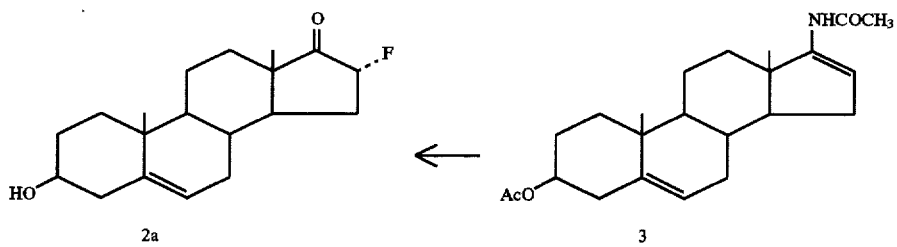

Alternatively, 2a could be prepared by treating an enamide, e.g., the enamide of Formula 3 with a fluorinating agent, such as perchloryl fluoride. Hydrolysis of the fluoro enamide acetate with aqueous acid gives 2a.

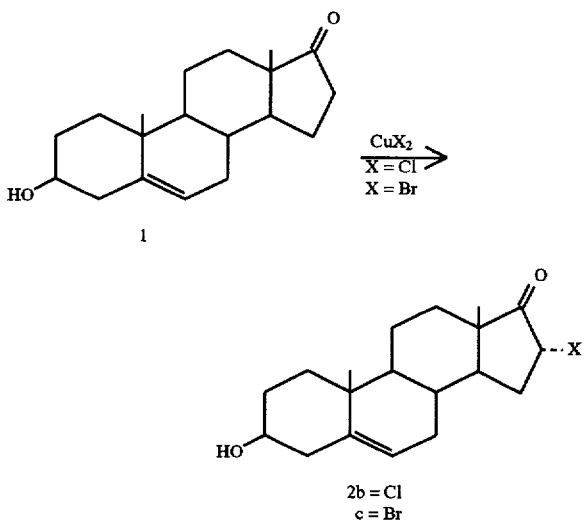

Reaction of 3β-hydroxyandrost-5-en-17-one 1 with cupric bromide yields 16α-bromo-3βhydroxyandrost-5-en-17-one, 2c[1]. Similarly, reaction of 1 with cupric chloride yields 16α-chloro-3β-hydroxyandrost-5-en-17-one, 2b.

[1]E. R. Glazier J. Org. Chem. 1962, 27, 4397

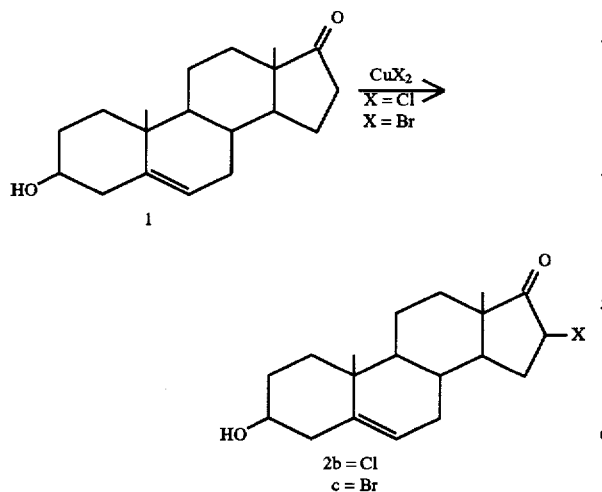

Reaction of 3β,17-dihydroxyandrosta-5,16-diene 17-acetate 1 with mercuric acetate followed by treatment with potassium iodide yields the C-16αiodide which hydrolyses with acid to yield 3β-hydroxy-16α-iodoandrost-5-en-17-one, 2d. Reaction of 2d with silver fluoride yields 3β-hydroxy-16α-fluoroandrost-5-en-17-one, 2a.

Alternatively, 2d can be formed from the reaction of 1 with N-iodo-succinimide.

In addition, the reaction of 2c with NaI/acetone overnight results in a mixture of 16α and 16βI-3β-hydroxy-5-androsten-17-ones. In any event, using the procedures outlined herein-above, the 3β-hydroxy derivatives can be converted to other groups representative of R₃, e.g., 3-alkyl derivatives. As indicated above, the 16αhalo-3-alkyl derivatives can be prepared by halogenation of DHEA followed by alkylation. Alternatively, the 16α-halo 3-alkyl derivatives can be prepared by first alkylating DHEA at the 3 position followed by halogenation. For example, the 16 chloro derivative can be prepared by first converting DHEA 1 to the 3-alkyl derivative, 2 in accordance with the procedure outlined in the section entitled Carbon-3-Alkylation, supra. The 3 alkyl derivative can then be chlorinated by the following procedure: The reaction of 2 with acetic anhydride affords the enol acetate, 3. The reaction of 3 with N-chlorosuccinimide yields the 3-alkyl-16α-chloro-5-androsten-17-one (4).

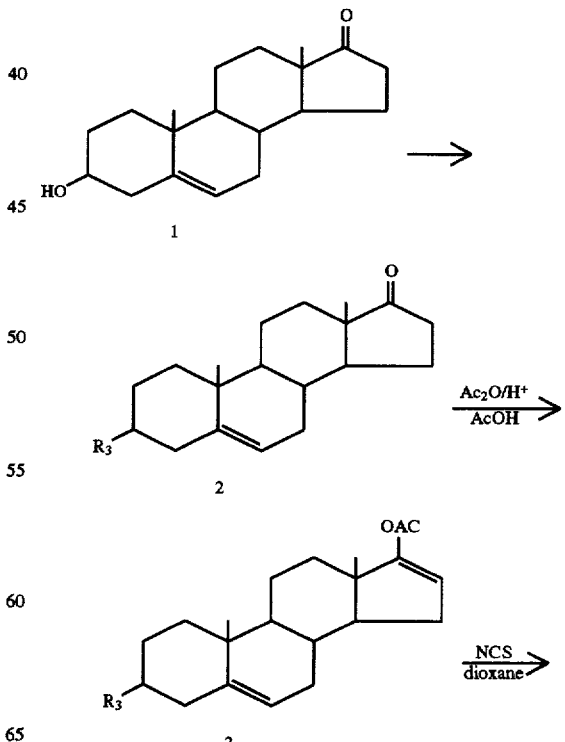

-continued

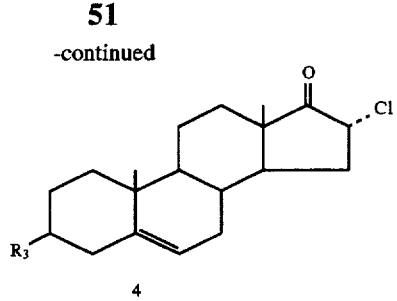

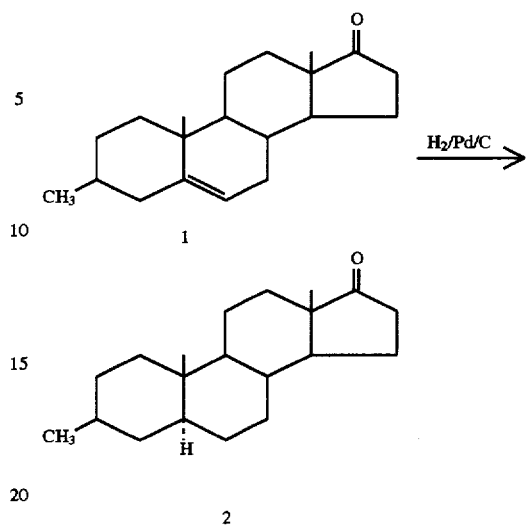

Similarly, the alkyl derivatives of 16 halo-5-androsten-17-one derivatives can be prepared using synthetic pathways known in the art. For example, using the procedure of the alkylation method described supra the 16-halo DHEA derivatives produced by the procedures described hereinabove is alkylated to produce the alkyl derivative of 16-halo-5-androsten-17-ones. As an example, 16 halo DHEA can be alkylated in the 3-position using the techniques described hereinabove to form 3 alkyl-16-halo-5-androsten-17-ones. Alternatively, the alkyl derivatives can be prepared using the methods described supra and then halogenated by the methods described hereinabove. For example, halogenation of 3-alkyl-5-androsten-17-one by the method described hereinabove would afford the corresponding 3-alkyl-16-halo-5-androsten-17-ones.

The following procedures are illustrative for the preparation of compounds of the present invention encompassed by the structure:

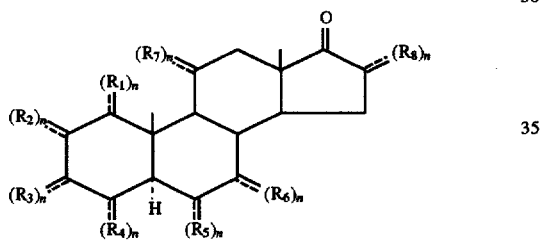

wherein $R_1$, $R_2$, $R_3$, $R_4$, $R_5$, $R_6$, $R_7$, $R_8$ and n are as defined hereinbefore.

Catalytic hydrogenation of 3β-substituted androst-5-enes yields almost exclusively 3β-substituted 5α-androstanes (for references see J. R. Lewis and C. W. Shoppee, *J. Chem. Soc.* 1955, 1365). Therefore all the syntheses of the substituted androst-5-enes described above can be used for the syntheses of the substituted 5α-androstanes, except those molecules which contain reducible double bonds such as the ethenyl and alkynyl derivatives. For these molecules the following syntheses are described.

Firstly an example of catalytic hydrogenation for the synthesis of 5α-androstanes from androst-5-enes is the synthesis of 3β-methyl-5α-androstan-17-one 2 from 3β-methylandrost-5-en-17-one 1. 3β-Methylandrost-5-en-17-one 1 (400 mg), prepared as described previously was dissolved in glacial acetic acid (80 ml). Palladium on carbon (10%, 100 mg) was added and the solution maintained under an atmosphere of hydrogen. When hydrogen uptake ceased, the solution was filtered through celite and evaporated to give solid which was recrystallized from methanol to yield 3β-methyl-5α-androstan-17-one, 2, (320 mg, 80% yield). MP 107°–108° C., $^1$H NMR (CDCl$_3$) δ 0.86 (d, 3H, J-5 Hz, methyl at C-3), 0.85 (s, 3H, C-19 Me), 0.79 (s, 3H, C-18 Me).

Anal Calc for $C_{20}H_{32}O$: C, 83.26%, H 11.18% Found: C, 82.99%, H 11.35%

Alkenylation and Alkynylation at Carbon-1.

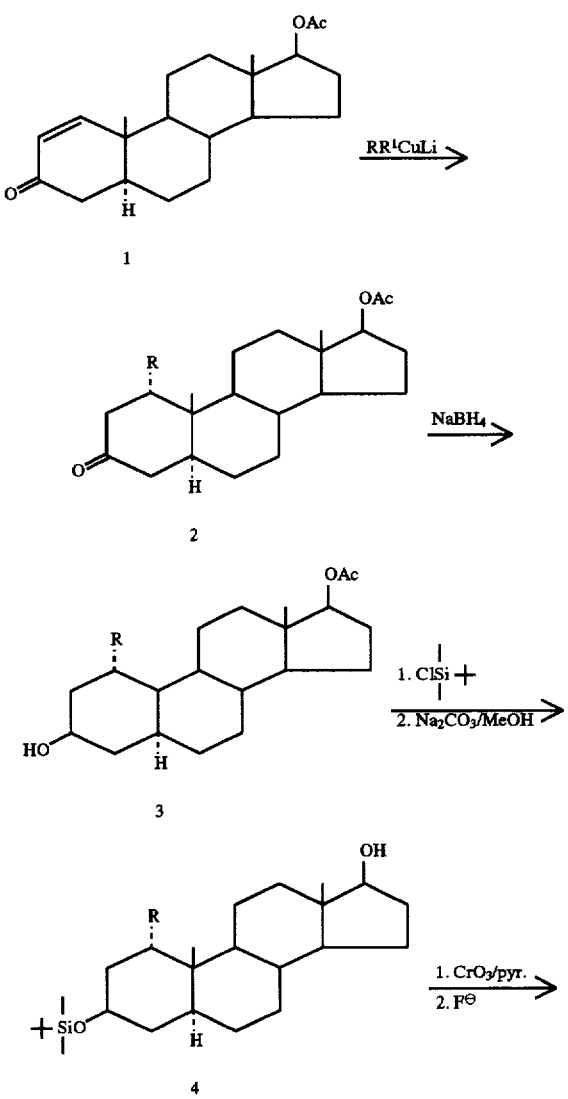

53
-continued
Alkenylation and Alkynylation at Carbon-1.

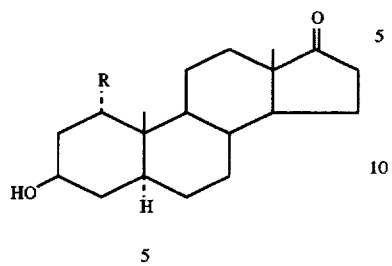

5

The following procedures are illustrative for alkenylation and alkynylation at carbon-1.

Michael addition to 17β-hydroxy-5α-androst-1-en-3-one 17-acetate, 1, using a dialkenyl lithium cuprate, (RR¹CuLi, R=R¹=CH=CHR²) yields the 1α-alkenyl-17β-hydroxy-5α-androstan-3-one 17-acetate 2. Reduction of the C-3 ketone in 2 yields the 3β-hydroxy steroid 3. Protection of the 3β-hydroxyl group as a dimethyl-t-butylsilyl ether followed by hydrolysis of the C-17 acetate yields 1α-alkenyl-3β, 17β-dihydroxy-5α-androstan 3-dimethyl-t-butylsilyl ether, 4. Oxidation of the C-17-hydroxyl group and deprotection of the 3β-hydroxyl group with fluoride ion affords 1α-alkenyl-3β-hydroxy-5α-androstan-17-one, 5. (R=CH=CHR' where R'=alkyl). Another method for preparing 5 (R=C≡CR' where R'=alkyl) may be carried out using the above procedure but with a different organo cuprate reagent. Using 2-tri-n-butylstannyl ethenyl 1'-pentynyl lithium cuprate (R R'CuLi is equivalent to [C₃H₇C≡C—Cu—CH=CHSnnBu₃]Li), (E. J. Corey and R. H. Wollenberg, *J. Amer. Chem. Soc.* 1974, 96, 5581), tri-n-butylstannylethylene is added to 1 to yield 2 with R=CH=CHSnn-Bu₃. Oxidation using lead tetraacetate proceeds with loss of tin and affords the corresponding acetylide 2, (R=C≡CH). Following through the reaction sequence as above yields 1α-ethynyl-3β-hydroxy-5α-androstan-17-one 5, R=C≡CH.

Alenylation and Alkynylation at Carbon-2.

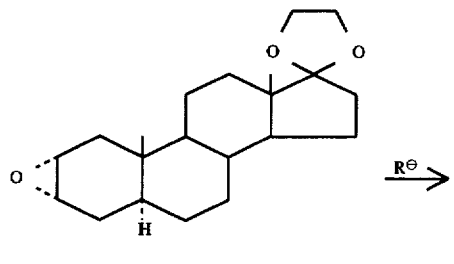

1

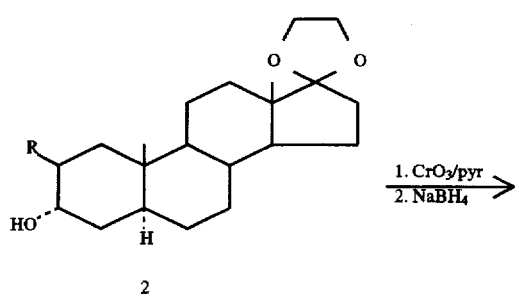

2

54
-continued
Alenylation and Alkynylation at Carbon-2.

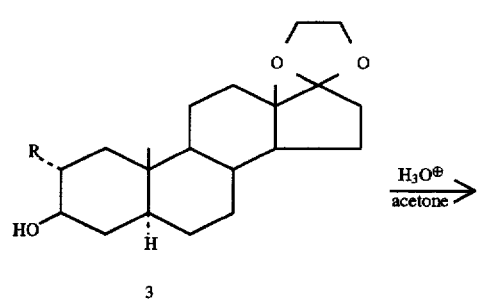

3

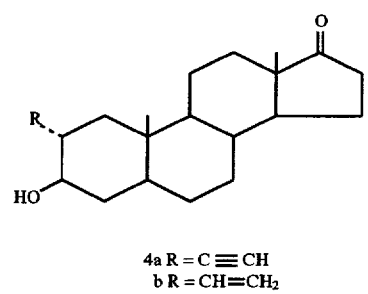

4a R = C≡CH
b R = CH=CH₂

Reaction of 2α, 3α-epoxy-5α-androstan-17-one 17-ketal 1 with lithium acetylide ethylene diamine complex yields 2β-ethynyl-5α-androstan-3β-ol-17-one 17-ketal 2, (R=C≡CH). Epimerization of the C-3 alcohol by oxidation to the C-3 ketone (chromium trioxide/pyridine) and reduction with sodium borohydride affords 2β-ethynyl-5α-androstan-3β-ol-17-one 17-ketal 3 (R=C≡CH). Deprotection of the 17-ketone by treatment with aqueous acid yields 2α-ethynyl-5α-androstan-3β-ol-17-one 4a. The 2α-ethenyl steroid can be synthesized from the ethynyl derivative by careful catalytic reduction with Lindlar catalyst to yield 2α-ethenyl-3β-hydroxy-5α-androstan-17-one, 4b.

Alkenylation and Alkynylation at Carbon-3.

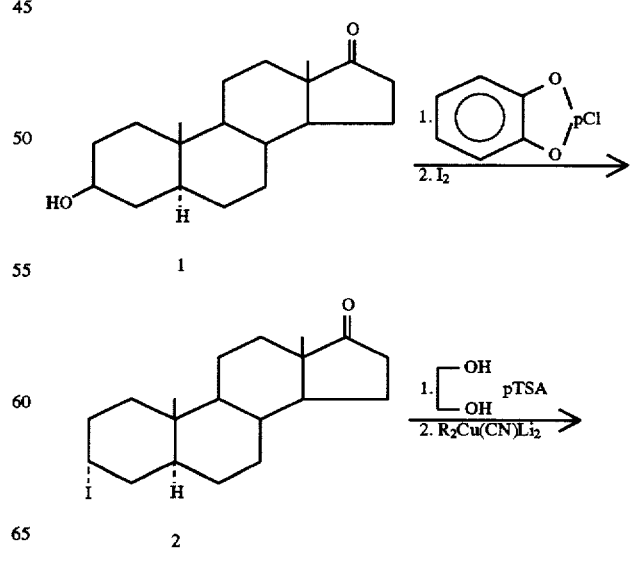

Alkenylation and Alkynylation at Carbon-3.

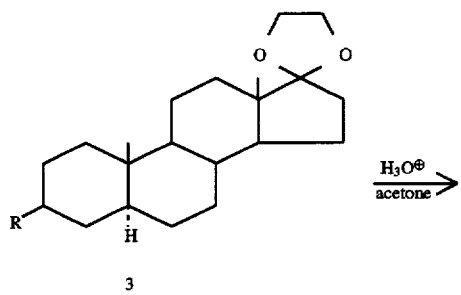

Reaction of 3β-hydroxy-5α-androstan-17-one with catechol phosphochloridate followed by iodine affords 3α-iodo-5α-androstan-17-one, 2. Protection of the C-17 ketone as a ketal followed by nucleophilic displacement of the C-3α-iodo group yields the 3β-substituted steroid 3. For alkenylation at C-3, such as introduction of a vinyl group, i.e. 3 (R=CH=CH₂), divinyl cyano dilithio cuprate, [(CH₂=CH)₂Cu(CN)]Li₂ is used. Hydrolysis of the C-17 ketal yields 3β-ethenyl-5α-androstan-17-one, 4 (R=CH=CH₂). Alkynylation using 2-tri-n-butylstannyl ethenyl 1'-pentynyl cyano dilithio cuprate, [C₃H₇C≡C—Cu—CH=CHSn-nBu₃(CN)]Li₂, yields the 3β-ethynyl derivative 3 (R=C≡CH). Hydrolysis of the C-17 ketal yields 3β-ethynyl-5α-androstan-17-one, 4, (R=C≡CH).

Alkenylation and Alkynylation at Carbon-4.

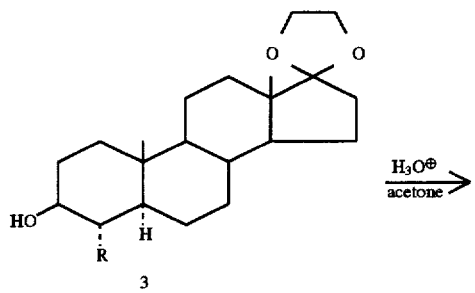

4a R = C≡CH
b R = CH=CH₂

Reaction of 3α,4α-epoxy-5α-androstan-17-one 17-ketal 1 with lithium acetylide diethylamine complex affords 4β-ethynyl-3α-hydroxy-5α-androstan-17-one 17-ketal 2 (R=C≡CH). Epimerization of the C-3 alcohol by oxidation to the C-3 ketone with chromium trioxide/pyridine followed by reduction with sodium borohydride affords 4α-ethynyl-3β-hydroxy-5α-androstan-17-one 17-ketal 3 (R=C≡CH). Careful hydrolysis of the C-17 ketal affords 4α-ethynyl-3β-hydroxy-5α-androstan-17-one, 4a (R=C≡CH). The 4α-ethenyl derivative, 4b, can be synthesized from the ethynyl derivative, 4a, by careful catalytic reduction with Lindlar catalyst or metal ammonia reduction to yield 4α-ethenyl-3β-hydroxy-5α-androstan-17-one, 4b.

Alkenylation and Alkynylation at Carbon-4.

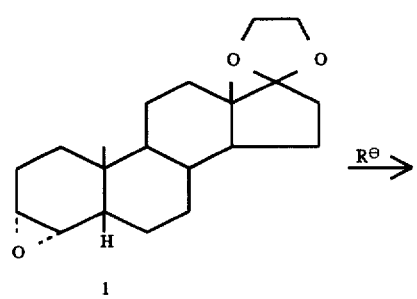

Alkenylation and Alkynylation at Carbon-6.

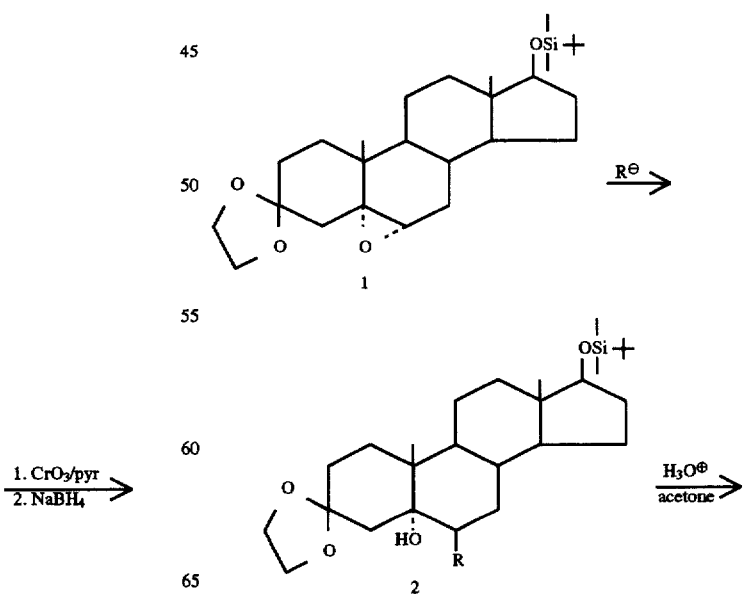

-continued
Alkenylation and Alkynylation at Carbon-6.

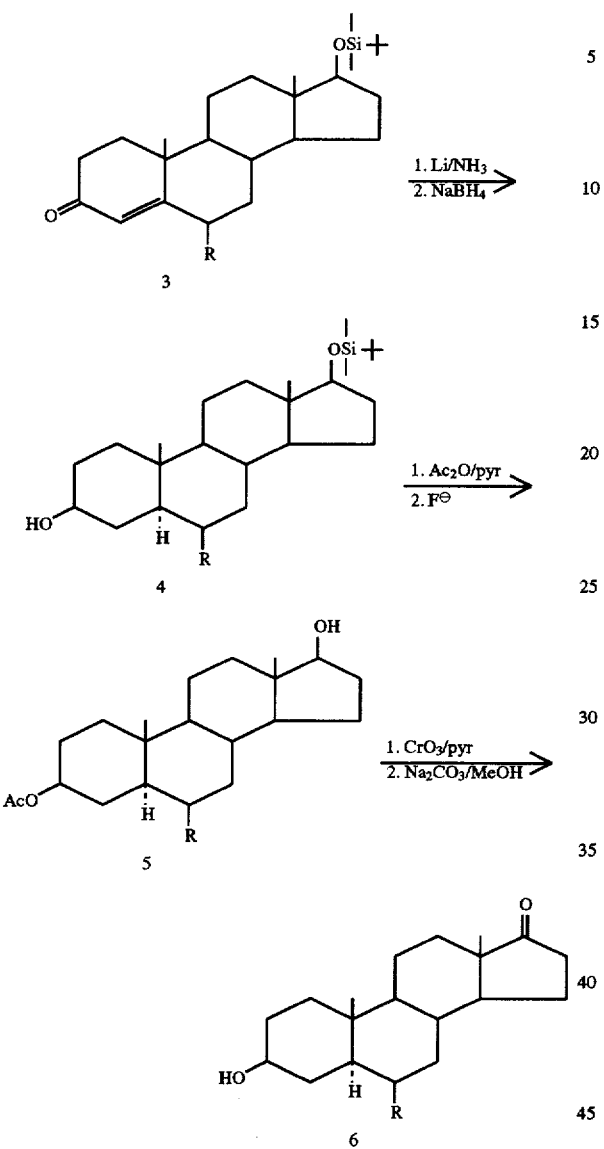

Reaction of 5α,6α-epoxy-3β-dimethyl-t-butylsilyl-oxyandrostan-3-one 3-ketal 1, with lithium acetylide-ethylenediamine complex yields 6β-ethynyl-5α-hydroxy-3β-dimethyl-t-butylsilyloxyandrostan-3-one 3-ketal, 2. Hydrolysis of the C-3 ketal and dehydration of the consequent β-hydroxy ketone yields the enone 3. If the C-17 silyl group is lost under these hydrolysis conditions the C-17 hydroxyl group will be reprotected. Reduction of 6β-ethynyl-17β-dimethyl-t-butylsilyloxyandrost-4-en-3-one, 3, with excess lithium in ammonia followed by rapid quenching with ammonium chloride affords primarily the 3-keto-4,5α-dihydro compound. (A. Bowers, H. J. Ringold, and E. Denot, J. Amer. Chem. Soc. 1958, 80, 6115). Sodium borohydride reduction of the C-3 ketone yields 6β-ethynyl-5α-androstan-3β,17β-diol 17-dimethyl-t-butylsilyl ether, 4. Protection of the C-3 alcohol as an acetate and deprotection at C-17 with fluoride ion yields 6β-ethynyl-5α-androstan-3β,17β-diol 3-acetate, 5. Oxidation of the C-17 hydroxyl group with chromium trioxide/pyridine followed by deprotection of the C-3-hydroxyl group yields 6β-ethynyl-5α-androstan-3β-ol-17-one, 6. Higher homologues can be synthesized from 6 by first protecting the ketone and alcohol then using the acetylide anion to react with primary alkyl halides. The C-6 ethenyl derivates (6 R=CH=CH$_2$) can be prepared by reduction of the corresponding C-6 ethynyl derivatives.

Alkenylation and Alynylation at Carbon-7.

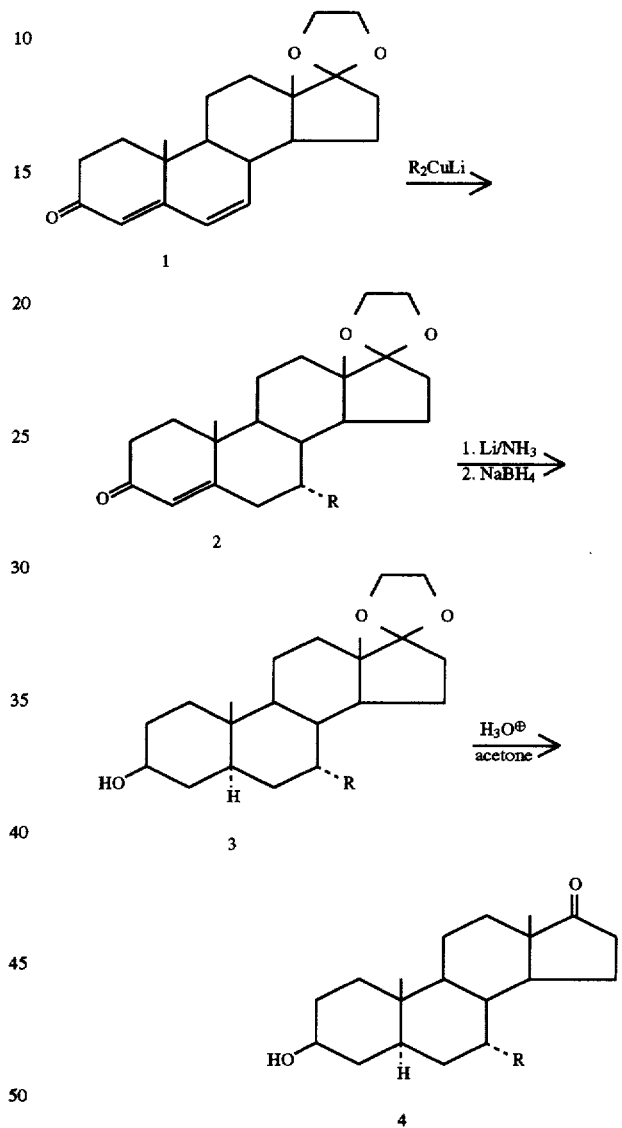

Alkenylation of androsta-4,6-dien-3,17-dione 17-ketal 1 with 2-tri-n-butylstannyl ethenyl 1'-pentynyl lithium cuprate ([C$_3$H$_7$C≡C—Cu—CH=CHSn nBu$_3$]Li) yields the 7α-alkenyl steroid 2 (R=CH=CHSn nBu$_3$). Oxidation using lead tetraacetate proceeds with the loss of tin and affords the corresponding acetylene 2 (R=C≡CH). Reduction of 7α-ethynylandrost-4-en-3,17-dione 17-ketal 2, (R=C≡CH), with excess lithium in ammonia followed by rapid quenching with ammonium chloride affords primarily the 3-keto-4,5α-dihydro compound. Sodium borohydride reduction of the C-3 ketone yields 7α-ethynyl-5α-androstan-3β-ol-17-one 17-ketal 3. Careful acid hydrolysis of the C-17 ketal yields 7α-ethynyl-5α-androstan-3β-ol-17-one 4 (R=C≡CH). Higher homologues can be synthesized from 4, by first protecting the ketone and alcohol, then using the acetylide anion to react with primary alkyl halides. The C-7 ethenyl derivatives 4 (R=CH=CH$_2$) can be prepared by reduction of the corresponding C-7 ethynyl derivatives.

Alkenylation and Alkynylation at Carbon-11.

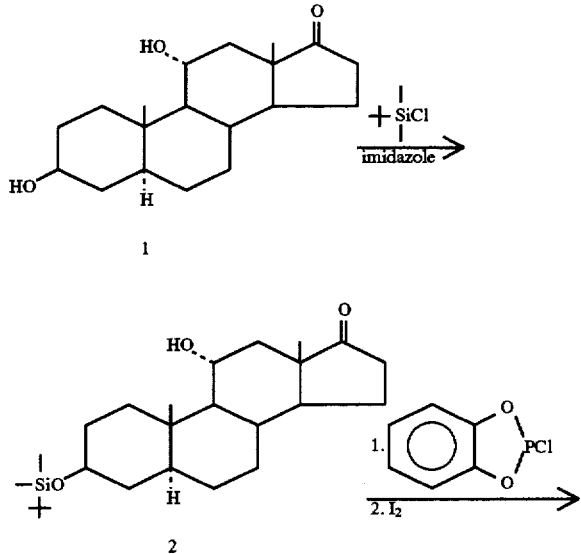

Alkenylation and Alkynylation at Carbon-11.
-continued

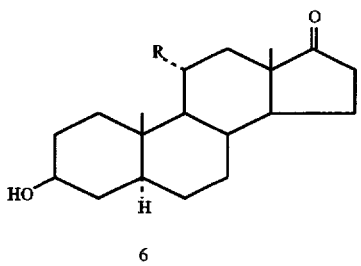

Reaction of the less hindered 3β-hydroxy-5α-androstan-17-one 1 with t-butyldimethylsilyl chloride yields the 3β-t-butyldimethylsilyl ether 2. Treatment of this first with catechol phosphochloridate followed by displacement with iodine yields 3β-hydroxy-11β-iodo-5α-androstan-17-one 3-dimethyl-t-butylsilyl ether 3. Protection of the C-17 ketone as the 1,3-dioxolane 4 followed by alkenylation using dialkenyl dilithio cyano cuprate, (RCH=CH)$_2$Cu(CN)Li$_2$ yields 11α-alkenyl-3β-hydroxy-5α-androstan-17-one-3-t-butyldimethylsilyl ether 5. Deprotection of the C-17 ketone and 3β alcohol affords 11α-alkenyl 3β-hydroxy-5α-androstan-17-one 6. If 6 has R=2'-tri-n-butylstannyl ethenyl, then lead tetraacetate oxidation affords 11α-alkynyl-3β-hydroxy-5α-androstan-17-one. 6, (R=C≡CH).

Alkenylation and Alkynylation at Carbon-16.

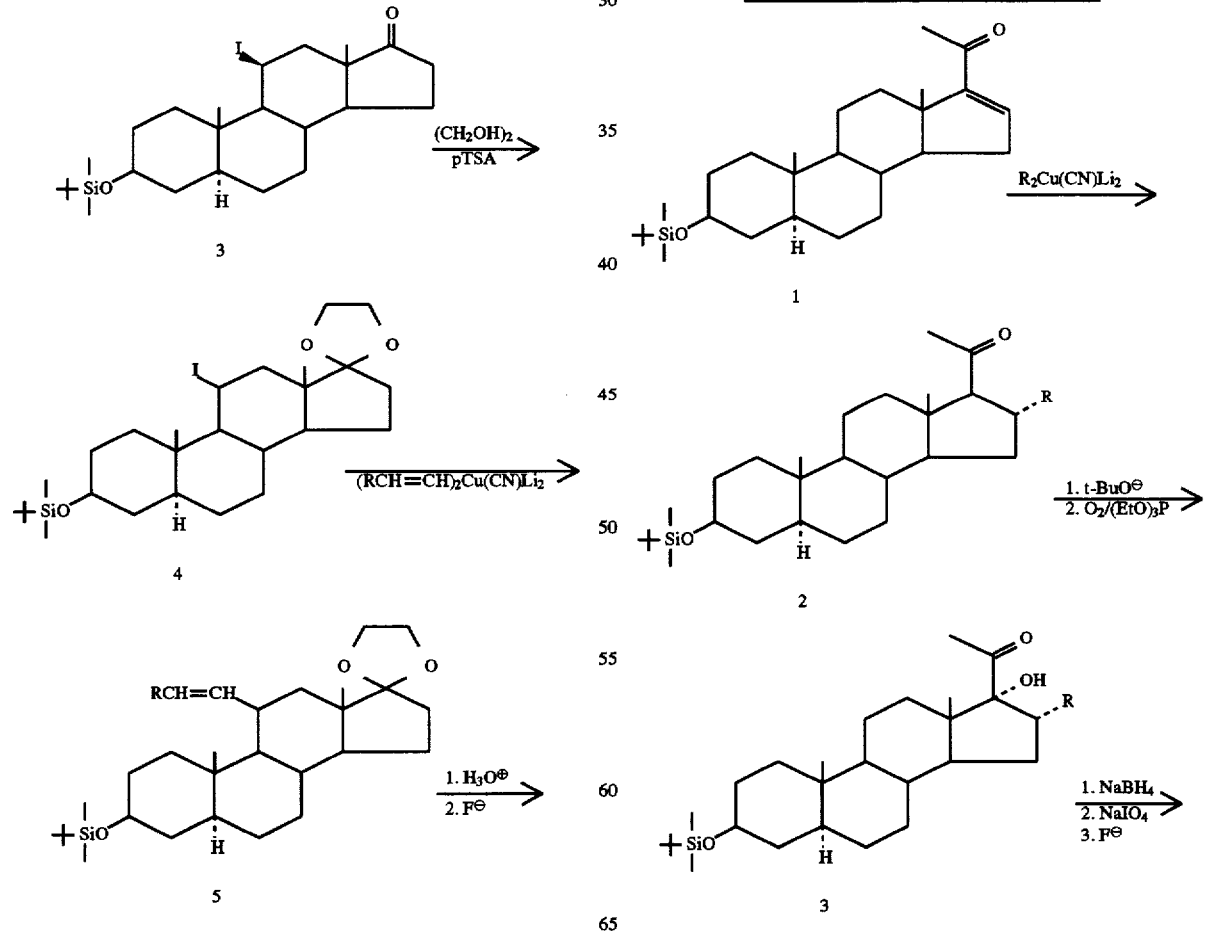

-continued

Alkenylation and Alkynylation at Carbon-16.

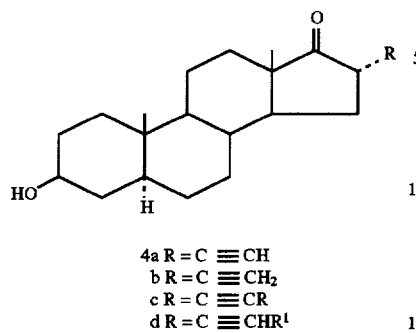

4a R = C ≡ CH
b R = C ≡ CH₂
c R = C ≡ CR
d R = C ≡ CHR¹

Michael addition of a suitably substituted organo copper reagent such as 2-tri-n-butylstannyl ethenyl 1'-pentynyl lithium cuprate ([C₃H₇C≡C—Cu═CH═CH—Sn nBu₃] Li) to 3β-hydroxy-5α-pregna-16-en-20-one 3-t-butyl dimethylsilyl ether 1 yields a 16α-tri-n-butylstannyl ethylene (2, R═CH═CHSn nBu₃). Lead tetracetate oxidation proceeds with the loss of tin and yields the corresponding acetylide. Treatment of 2 with t-butoxide followed by oxygen generates a C-16α-hydroperoxide which is reduced by triethylphosphite to 16α-ethynyl-3β,17β-dihydroxy-5α-pregnan-20-one 3-t-butyldimethylsilyl ether 3. Reduction of the C-20 ketone to an alcohol followed by cleavage of the diol with sodium periodate and deprotection of the 3β-hydroxyl group with fluoride, yields 16α-ethynyl-3β-hydroxy-5α-androstan-17-one, 4a (R═C≡CH). Careful reduction of the acetylene in 4a should afford the 16α-vinyl substituted steroids, 4b (R═CH═CH₂). Higher homologues of these substituents may be synthesized via acetylide chemistry using 4a with its hydroxyl and ketone groups first protected. Reduction of the substituted acetylene will afford both E and Z olefinic substituents at C-16.

The following examples further illustrate the invention:

EXAMPLE I

3β,16β-dimethylandrost-5-en-17-one

To a solution of 16β-methyl-3β-hydroxy-5,16-pregnadien-20-one was added toluene, ethylene glycol, and p-toluene-sulfonic acid. The resulting solution was refluxed overnight forming the 20-ketal. The procedure for this ketalization step is described in JACS, 76, 5674 (1954). Tosyl chloride in pyridine was added to the above product to form the 3β-tosylate derivative. The 3β-tosylate was refluxed overnight with 10% NaI/acetone to form the 3β-iodo-16-methyl-5,16-pregnadien-20-one-ethylene ketal. This product was methylated with lithium dimethylcuprate in ether and tetrahydrofuran at −78° C. under a nitrogen atmosphere to form the 3β,16-dimethyl-5,16-pregnadien-20-one ethylene ketal. This product was deketalized by refluxing in the presence of acetone/p-toluenesulfonic acid. The resulting 3β,16-dimethyl,5,16-pregnadien-20-one was converted to the C-20-oxime by refluxing in ethanol and pyridine with an excess of hydroxylamine hydrochloride. This product was subjected to a Beckmann rearrangement in the presence of p-acetamidobenzenesulfonyl chloride/pyridine according to the procedure by Rosenkranz, et al. in *J. Org. Chem.*, 21, 520–522 (1956). The product, 17-acetamido-3β,16-dimethyl-5,16-androstadiene was refluxed in tetrahydrofuran/hydrochloric acid solution. 3β,16α-dimethyl-5-androst-en-17-one was formed, separated and purified by normal phase HPLC using a 1 in.×25 cm silica gel preparative column at a flow rate of 30 ml/min and using ethyl acetate/hexane (in a gradient ranging from 0 to 20%) as the eluent. The product was recrystallized from methanol and characterized by NMR and IR. Colorless crystals were isolated:

3β,16β-dimethyl-5-androsten-17-one m.p. 86.5°–88.5° C.

EXAMPLE II

3β-methyl-16α-fluoro-5-androst-5-en-17-one

Starting from 3β-hydroxy-5,16 pregnadien-20-one and following the procedure of Example I, the 20-oxime of 3β-methyl-5,16 pregnadien-20-one was formed. Beckmann rearrangement of this product in the presence of p-acetamidobenzenesulfonyl chloride/pyridine according to the procedure by Rosenkranz, et al. in *J. Org. Chem.* 21, 520–522 (1956) followed by treatment of the resulting enamide with perchloryl fluoride and acid hydrolysis affords the above-identified product.

EXAMPLE III

16α-fluoro-3β,16β-dimethyl-5-androst-en-17-one

The procedure is identical to the formation of 3-βmethyl-16α-fluoro-androst-5-en-17-one except that the starting material is 3β,16-dimethyl-5, 16-pregnadien-20-one. The final product which was purified by normal phase HPLC using ethylacetate-hexane as eluent, and recrystallized from methanol, formed a colorless crystal which melted at 129°–130° C.

EXAMPLE IV

16α-bromo-3β-methyl-5-androsten-17-one

3β-methyl-5-androsten-17-one (4.0 g, 14 mmol) and CuBr₂ (9.4 g, 4.2 mmol) were dissolved in methanol (250 ml) and refluxed for 24 hours. The hot solution was filtered to remove the white precipitate and the filtrate was cooled to yield 3.1 g (61%) of 16α-bromo-3β-methylandrost-5-en-17-one. An analytical sample was prepared by passing an ether solution of the steroid through a small plug of neutral alumina. Evaporation and recrystallization from methanol gave white needles: mp 193°–195° C.; NMR (CDCl₃) δ 5.30 (br.d, 1H, H-6), 4.52 (t, 1H, 16β-H), 0.98 (s, 3H, C-19-Me), 0.90 (s, 3H, C-18 Me); IR (KBr) 2910, 1735, 1445, 1365, 1020; MS: 366 (M⁺, 100), 364 (96), 351 (75), 349 (70), 285 (35), 283 (44), 282 (23), 281 (46), 267 (25); Anal. Calcd for C₂₀H₂₉OBr:C,65.70; H, 8.00. Found C, 65.54, H, 8.11.

EXAMPLE V

16β-bromo-3β-methyl-5-androsten-17-one

The 16α-bromo derivative (365 mg, 1 mmole) that was formed in Example IV was refluxed in 10 ml isopropanol and 30 ml toluene 635 mg (5 mmole) of AgF for 18 hours. The reaction mixture was washed with brine and filtered through anhydrous Na2SO₄ and dried. The reaction mixture was subjected to preparative HPLC on a silica gel column. The most mobile product was obtained as platelets from CH₃OH in a yield of 130 mg m.p. 186°–188°.

EXAMPLE VI

16α-iodo-3β-methyl-5-androsten-17-one

16β-iodo-3β-methyl-5-androsten-17-one

The 16α-bromo derivative that was formed in Example IV was refluxed with sodium iodide in acetone overnight.

The mixture of the 16α-iodo and the 16β-iodo derivatives were formed which were separated by normal phase HPLC, using silica gel as adsorbent in a column 1 in.×25 cm, using ethyl acetate:hexane (gradient from 0→20%) as the eluent.

EXAMPLE VII

Preparation of 3β-Iodo-16α-Fluoro-5-Androsten-17-one (See Corey and Anderson, JOC 32, 4160, 1967)

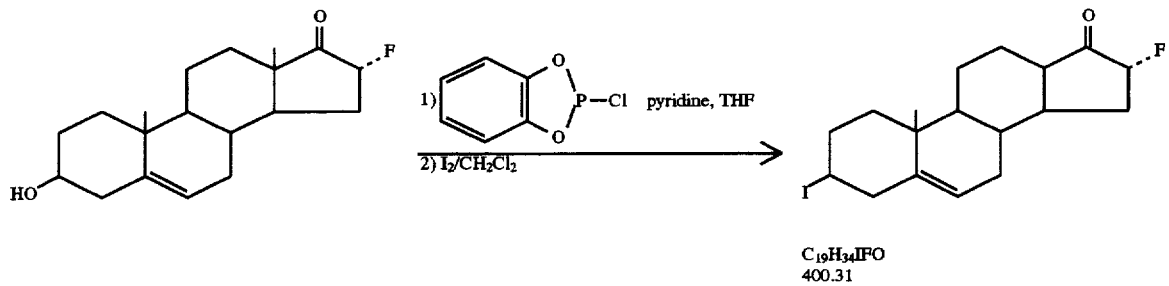

$C_{19}H_{34}IFO$
400.31

To a solution of pyridine (0.41 ml) and O-phenylenephosphorochloridite (0.6 ml) in anhydrous THF (10 ml) at 0° was added 1.53 g (5 mmoles) of the hydroxyfluoroketone in 10 ml of THF. After stirring for two hours at room temperature, the pyridinium chloride was filtered off and washed with THF. After removal of the solvent in vacuo, the crude phosphite ester was dissolved in 25 ml of methylene chloride and treated with 1.27 g of iodine for three hours at room temperature. The reaction mixture was washed succesively with 15 ml of 1N sodium hydroxide and water, filtered through anhydrous sodium sulfate, and the product was crystallized from methylene chloride methanol in a yield of 1.85 g (92.5%), mp 165°–167° (dec.) λ max 1755 cm$^{-1}$ (16-fluoro-17-one).

EXAMPLE VIII

Preparation of 16α-methyl-3β-hydroxy-5-androsten-17-one, 16α-methyl-3β-iodo-5-androsten-17-one, 16β-methyl-3β-hydroxy-5-androsten-17-one, 16β-methyl-3β-iodo-5-androstene-17-one, 16α-methyl-16α-fluoro-3β-hydroxy-5-androsten-17-one and 16β-methyl-16α-fluoro-3β-iodo-5-androsten-17-one

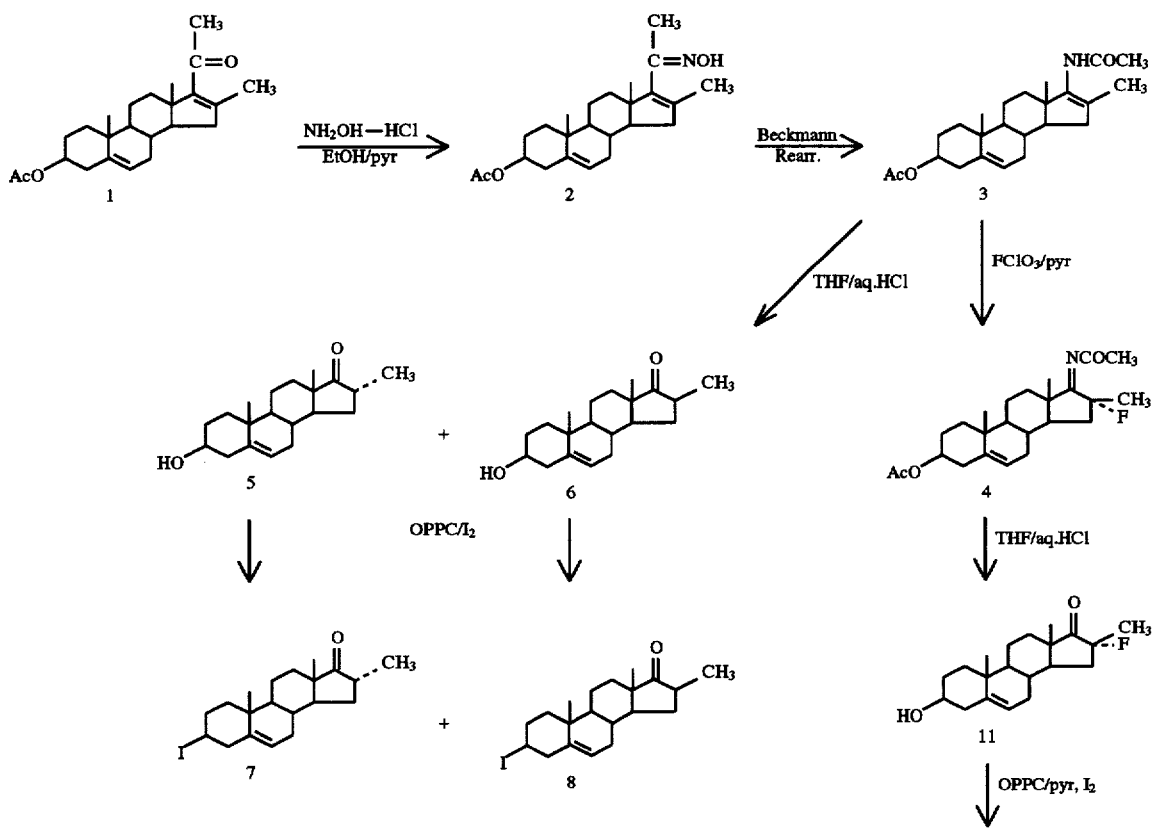

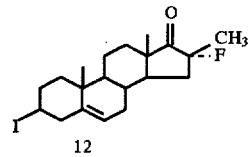

I. Preparation of 16-methyl-3β-acetoxy-5,16-pregnadien-20-one oxime (2)

A solution of 16-methyl-3β-acetoxy-5,16-pregnadien-20-one (3.70 g, 10 mmoles) was refluxed in a mixture of ethanol (100 ml) and pyridine (10 ml) containing 3.50 g (50 mmoles) of hydroxylamine hydrochloride for one hour. The reaction mixture was added to water and the crude product was filtered and washed with water. Solution in methylene chloride, filtration through anhydrous sodium sulfate, and concentration to dryness in vacuo gave the crude oxime.

II. Beckmann Rearrangement of I.

Treatment of the crude oxime from 3.70 g of 20-one in 15 ml of pyridine with 3.75 g of p-acetamidobenzene-sulfonyl chloride was carried out for 2 hours at 10°. The reaction mixture was added to ice water, furnishing a filterable solid which was washed thoroughly with water. The dried product was 17-acetamido-16-methyl-5,16-androstadien-3β-ol acetate (3), weighing 3.88 g.

III. Reaction of 3 with Perchloryl Fluoride/Pyridine.

A solution of the 16-methyl enamide acetate (1.94 g) in pyridine (100 ml) was treated with $FClO_3$ for 4 minutes as described in Example IB. The reaction mixture was added to ice water and cold, concentrated HCl was added until the reaction mixture has a pH 1. The resulting precipitate was filtered off and washed with water. The product was dissolved in methylene chloride and filtered through anhydrous sodium sulfate, affording the crude fluoro methyl enamide acetate (4).

IV. Preparation of 16β-methyl-16α-fluoro-3β-hydroxy-5-androsten-17-one (11).

A solution of (4) in tetrahydrofuran (100 ml) and water (100 ml) was refluxed in 10 ml of concentrated hydrochloride acid for 14 hours. The reaction mixture was partitioned between methylene chloride and water and the organic layer was filtered through anhydrous sodium sulfate. The crude hydroxy methyl fluoro ketone was subjected to preparative HPLC on a silica gel column in isopropyl alcohol/n-hexane. Crystallization of the major product from methanol gave long needles (420 mg, mp 177–180; 90 mg, mp 170–173). The mother liquor residue (350 mg) from the crystalline product was employed in the next step.

V. Preparation of 16β-methyl-16α-fluoro-3β-iodo-5-androsten 17-one (12)

The crude 3β-ol (4, 350 mg) from the previous step was added in 5 ml of methylene chloride to 5 ml of methylene chloride containing 90 μl of pyridine and 130 μl of O-phenylenephosphorochloridite at 0° C. After standing for 2 hours at room temperature the crude phosphite was treated with 280 mg of iodine and the resulting mixture was stirred magnetically at room temperature for 2½ hours. The reaction mixture was washed successively with 1N NaOH (6 ml) and water (10 ml) and filtered through sodium sulfate and dried, affording 12.

VI. Preparation of 16α and 16β-methyl-3β-hydroxy-5-androsten-17-ones

The crude methyl enamide acetate (3, 1.94 g) was refluxed in 100 ml each of THF and water with 10 ml of concentrated HCl for 3½ hours. Following the usual work-up the crude hydroxy methyl ketones (5 and 6) were converted to the 3-acetates. Silica gel thin layer chromotography using isooctane-ethyl acetate (21:4) roughly showed a 3:1 mixture of polar ($R_f$ 0.17) and mobile ($R_f$ 0.21) products, representing a mixture of the 16α-methyl and 16β-methyl-17-ones, respectively. Crystallization of the original 3-hydroxy mixture gave 425 mg of pure 16β-methyl-5-androsten-17-one (6), mp 168°–170°. The mother liquor residue (660 mg) represented a mixture of 16α and 16β-methyl-3-hydroxy-17-ones (5 and 6).

VII. Preparation of 16-α and 16β-methyl-3β-iodo-5-androsten-17-one

A solution of this mixture plus 6 ml of methylene chloride was added to 6 ml of methylene chloride containing 180 μl of pyridine and 260 μl of O-phenylenphosphorochloridite at 0° C. and the mixture stood at room temperature for 2 hours. After addition of iodine (560 mg) to the crude phosphite, the reaction proceeded for 2½ hours at room temperature. The reaction mixture was washed with 10 ml of 1N NaOH and 10 ml of water. The mixture of iodides (7 and 8) was subjected to preparative HPLC on a silica gel column in ethyl acetate hexane. The more mobile product, designated 16α-methyl-3β-iodo-5-androsten-17-one (7) crystallized from methanol as needles (120 mg), mp 150°–151.5°.

μmax 1728 $cm^{-1}$ (characteristic of 16α-methyl-17-ones according to Neef, et al., JOC 43, 4579, 1978).

The less mobile product, designated 16β-methyl-3β-iodo-5-androsten-17-one (8) crystallized as needles (200 mg) from methanol, mp 151–153, μmax 1734 $cm^{-1}$ (characteristic of 16β-methyl-17-ones according to Neef, et al.).

EXAMPLE IX

3β,16β-dimethyl-5α-androstan-17-one

To a solution of 3β,16β-dimethylandrost-5-en-17-one prepared in Example I in 500 ml of ethanol is added 5% Pd on C and the mixture is exposed to a hydrogen atmosphere while stirring. The catalyst is filtered off and the above-identified product is isolated.

Similarly, using the appropriate starting materials the following compounds are prepared:

3βmethyl-16αfluoro-5α-androstan-17-one

16αfluoro-3β,16β-dimethyl-5α-androstan-17-one

3β-methyl-16α-hydroxy-5α-androstan-17-one

16β-methyl-16α-bromo-5α-androstan-17-one

EXAMPLE X

3β-methyl-16α-chloro-5-androsten-17-one 800 mg of 3β-methyl-16β-trifluoromethylsulfonyloxy-5-androsten-17-one, prepared from 3β-methyl-16α-hydroxy-5-androsten-17-one and trifluoromethane sulfonic acid was placed in 16 ml DMF and was treated with 100 mg Lithium chloride at room temperature. The reaction mixture was stirred magnetically for 21 hours. Water is then added and the resulting crystalline ppt was collected. The crystals were washed with additional water and were then dissolved in CH$_2$Cl$_2$, filtered through anhydrous sodium sulfate and the solvent was evaporated off. The resulting crystals were recrystallized from CH$_3$OH, yielding 570 mg of final product. m.p. 159°–165° C.

EXAMPLE XI

16α,16β-difluoro-3β-methyl-5-androsten-17-one

Formylation of 3-methyl-5-androsten-17-one using the procedure of C. H. Robinson, et al., J. Org. Chem. 28, 975 (7963) gives the corresponding 16-hydroxymethylenes. Fluorination of the hydroxy methylene-17-one in a t-butyl alcohol/potassium t-butoxide system (six moles of butoxide per mole of steroid) with perchloryl fluoride, according to the procedure of Robinson, et al., JOC 28, 975, 1963, affords the 16,16-difluoro-3β-methyl-5-androsten-17-one.

EXAMPLE XII

16α,16β-difluoro-3β-methyl-5α-androstan-17-one

Reacting 3β-methyl-5α-androstan-17-one according to the procedure in Example XI affords the final product.

EXAMPLE XIII

3β,16,16-Trimethyl-5-Androsten-17-one

Treatment of 3β-methyl-5-androsten-17-one in t-butyl alcohol and potassium t-butoxide with excess methyl iodide gives the above-identified product.

EXAMPLE XIV

3β,16,16-Trimethyl-5α-Androstan-17-one

Treatment of 3β-methyl-5-androstan-17-one in t-butyl alcohol and potassium t-butoxide with excess methyl iodide gives the above-identified product.

EXAMPLE XV

3β-Hydroxy-4α-methylandrost-5-en-17-one

A. 6β-Bromo-17β-hydroxy-4-methylandrost-4-en-3-one 4-methyltestosterone (1 g, 3.31 mmol), N-bromosuccinimide (0.589 g, 3.31 mmol) and benzoyl peroxide (20 mg) were refluxed in dry carbon tetrachloride (50 ml) for 15 min. The reaction mixture was then cooled to 0° C. and the precipitated material was separated by filtration. The filtrate was washed with 5% sodium bicarbonate, then water and the organic layer was then dried and the solvent removed to give 6β-bromo-4-methylandrost-4-en-3-one, m.p. 124°–125° C., $^1$H NMR:δ5.4 (m, 1H), 3.68 (t, 3H ), 1.86 (s, 3H), 1.52 (s, 3H), 0.85 (s, 3H).

B. 4α-methylandrost-5-en-3β,17β-diol

The 6β-bromide (190 mg, 0.5 mmol) was added to a solution of Red-A1 (300 eq) in toluene (40 ml). The reaction mixture was stirred at 80° C. for 24 hours, cooled to 0° C. and sodium hydroxide (20 ml of a 20% sol.) was added slowly. The mixture was extracted with ethyl acetate (2×100 ml), and the organic layer washed with water, and then brine. The organic layer was then dried, and evarporated to yield 4α-methylandrost-5-en-3β,17β-diol, m.p. 210°–214° C. IR:3500 cm$^{-1}$ (OH strong), no C=O. M.S. m/e 304.2 (100%), 286 (52), 271 (38), 105(35).

Similar results were obtained when the 6β-bromide was reduced with a large excess of LAH (80 mmol) using ether as a solvent.

C. 3β-Hydroxy-4α-methylandrost-5-en-17-one

To the diol formed in B above, (0.723 g, 2.38 mmol) dissolved in dimethylformamide (140 ml) was added manganese dioxide and the mixture stirred for four days. The maganese dioxide was filtered off and ethyl acetate added to the filtrate. The organic layer was washed with aqueous sodium bicarbonate, brine, and dried. Evaporation of the solvents followed by intensive chromatography of the residue over silica gel afforded 3β-hydroxy-4α-methylandrost-5-en-17-one. IR 3493 (OH), 1745 (C=O). $^1$H NMR (CDCl$_3$):δ 5.64 (m, 1H, H-6), 3.06 (m, 1H,H-3α), 1.72 (bis, 4 CH$_3$), 1.07 (s, 3H, 19-CH$_3$) 0.89 (s, 3H, 18-CH$_3$). M.W., calculated for C$_{20}$H$_{30}$O$_2$=302.2247; Found 302.2242.

EXAMPLE XVI

3α-Hydroxy-1α-methylandrost-5-en-17-one

A. 3,17β-Dihydroxy-1α-methylandrosta-3,5-diene diacetate

17β-Hydroxy-1α-methylandrost-4-en-3-one (1α-methyltestosterone, 1.0 g, 3.3 mmol) was dissolved in pyridine (10 ml) and acetic anhydride (10 ml) and stirred at room temperature under a drying tube for 18 hours. The mixture was poured into cold water and the precipitate collected and washed with additional cold water. After drying, the solid was chromatographed on flash SiO$_2$ and eluted with 5% ether—95% hexane. There was obtained 1.18 g (93%) of 3,17β-dihydroxy-1α-methylandrosta-3,5-diene diactate 51, which was recrystallized from methanol-water: mp 111°–112° C.; NMR (CDCl$_3$) δ 5.65 (d, J=3 Hz, 1H, H-4), 5.52 (br s, 1H, H-6), 4.64 (t, 1H, H-17), 2.10 (s, 3H, Ac), 2.02 (s, 3H, Ac), 1.05 (s, 3H, C-18 Me), 0.83 (s, 3H, C-19 Me), 0.86 (d, 3H, C-1 Me); IR (KBr) 2910, 1745, 1730, 1360, 1245, 1215; MS 386 (M$^+$, 4), 358(1), 344(100), 329(2), 315 M* (344–329), 301(1), 151(1), 43(13); Anal. Calcd for C$_{24}$H$_{34}$O$_4$: C, 74.57; H, 8.86. Found: C, 74–39; H, 8.62.

B. 3β,17β-Dihydroxy-1α-methylandrost-5-en-17-acetate

The diacetate formed hereinabove (1.00 g, 2.67 mmol) was dissolved in 95% ethanol (100 ml). Sodium borohydride (1.00 g, 26.3 mmol) was added and the mixture stirred at room temperature under a drying tube for 8 hours. Acetic acid (1.5 ml) was carefully added and the solution was evaporated to dryness. The solid was taken up in methylene chloride (30 ml) and washed with dilute hydrochloric acid, water, then dried over magnesium sulfate, filtered, evaporated, and chromatographed on flash SiO$_2$. Elution with 10% ethyl acetate—90% hexane gave 465 mg (52%) of 3α,17β-dihydroxy-1α-methylandrost-5-en-17-acetate: NMR (CDCl$_3$) δ 5.51 (br d, 1H, H-6), 4.61 (t, 1H, H-17), 4.04 (br s, 1H, OH), 2.01 (s, 3H, Ac), 1.08 (s, 3H, C-18 Me), 0.79 (d, J=4 Hz, 3H, C-1 Me), 0.81 (s, 3H, C-19 Me); IR (KBr), 3400, 2890, 1725, 1360, 1245, 1035; MS 346 (M$^+$, 26), 328(77), 313(12), 286(12), 262(10), 253(14), 202(11), 43(100); Anal. Calcd for C$_{22}$H$_{34}$O$_3$: C, 76.26; H, 9.89. Found: C, 76.08; H, 9.72.

C. 3α,17β-Dihydroxy-1α-methylandrost-5-en-3-t-butyldimethylsilyl-17-acetate

3α,17β-Dihydroxy-1α-methylandrost-5-en-17-acetate formed hereinabove (3.4 g, 0.98 mmol) was dissolved in freshly distilled dimethylformamide (10 ml). Imidazole (0.61 g) and tert-butyldimethylsilyl chloride (0.77 g, 5.1 mmol) were added and the mixture stirred for 18 hours at room temperature. Water (30 ml) was added and the solution extracted with ether (2×100 ml). The combined organic layers were dried over magnesium sulfate, filtered, and evaporated to dryness to afford 0.44 g (97%) of 3α,17β- dihydroxy-1α-methylandrost-5-en-3-t-butyldimethylsilyl-17-acetate: NMR (CDCl$_3$) δ 5.38 (br d, 1H, H-6), 4.60 (t, 1H, H-17), 3.91 (s, 1H, H-3), 2.01 (s, 3H, 17-Ac), 1.05 (s, 3H, C-19 Me), 0.91 (s, 9H, t-Bu), 1.06 (s, 3H, C-18 Me), 0.80 (d, J=4 Hz, 3H, C-1 Me); IR (KBr) 2950, 1740, 1460, 1365, 1250, 1055; MS 460 (M$^+$, 16), 445(3), 403(100), 343(6), 327(35), 269(17) 199(17), 142(34); Anal. Calcd for C$_{28}$H$_4$O$_3$Si: C, 72.99; H, 10.50. Found: C, 73.17; H, 10.48.

D. 3α,17β-Dihydroxy-1α-methylandrost-5-en-3-t-butyldimethylsilyl ether

3α,17β-Dihydroxy-1α-methylandrost-5-en-3-t-butyldimethylsilyl-17-acetate formed hereinabove (0.44 g, 0.95 mmol) was dissolved in tetrahydrofuran (5 ml), methanol (20 ml), water (5 ml) and potassium bicarbonate (1 g) and refluxed for 18 hours. The solution was filtered, evaporated to dryness, taken up in chloroform (20 ml) and washed with dilute hydrochloric acid and then water. The organic layer was dried over magnesium sulfate, filtered and evaporated to give 3α,17β-dihydroxy-1α-methylandrost-5-en-3-t-butyldimethylsilyl ether, 0.39 g (97%): mp 126°–127° C.; NMR (CDCl$_3$) δ 5.39 (br s, 1H, H-6), 4.01 (br s, 1H, H-3β), 3.57 (t, 1H, H-17), 1.12 (s, 3H, C-19 Me), 0.92 (s, 9H, t-butyl), 1.10 (s, 3H, C-18 Me), 0.79 (d, 3H, C-1 Me); IR (KBr) 3420, 2920, 1460, 1250, 1050; MS 418 (M$^+$, 3), 403(2), 361(100), 343(3), 286(63), 271(10), 253(9); Anal. Calcd for C$_{26}$H$_{46}$O$_2$Si: C, 74.58; H, 11.07. Found: C, 74.36; H, 11.29.

E. 3α-Hydroxy-1α-methylandrost-5-en-17-one

3α,17β-Dihydroxy-1α-methylandrost-5-en-3-t-butyldimethylsilyl ether formed hereinabove (0.20 g, 0.478 mmol) and sodium acetate (20 mg, 0.24 mmol) were dissolved in dry methylene chloride (15 ml). Pyridinium chlorochromate (0.3 g, 1.43 mmol) was added in one portion and the mixture stirred for 2 hours. The solution was diluted with ether (30 ml) and passed through a small plug of florisil. Evaporation of the solvent gave 200 mg (100%) of 3α-hydroxy-1α-methylandrost-5-en-17-on-3-tertbutyldimethyl silyl ether which was used without further purification. Several runs were combined. This compound (1.1 g, 2.64 mmol) was dissolved in dry tetrahydrofuran (20 ml) tetra n-butylammonium fluoride (8.0 ml, 7.9 mmol) was added and the solution stirred for 2 hours. An additional portion (5.0 ml) of (n-Bu)$_4$NF was added and the solution refluxed for 48 hours. Water (60 ml) was added and the mixture extracted with ethyl acetate (100 ml). The organic layer was separated, dried, filtered and evaporated. The residue was chromatographed on SiO$_2$ and eluted with 5% ether-95% hexane. There was obtained 0.64 g (80%) of 3α-hydroxy-1α-methylandrost-5-en-17-one: mp 167°–169° C.; NMR (CDCl$_3$) δ 5.55 (br s, 1H, H-6), 4.07 (br s, 1H, H-3β), 1.11 (s, 3H, C-18 Me), 0.89 (s, 3H, C-19 Me), 0.81 (s, 3H, C-1 Me); IR (KBr) 3460, 2930, 1715, 1450, 1360; Anal. Calcd fop C$_{20}$H$_{30}$O$_2$: C, 79.42; H, 9.99. Found: C, 79.18; H, 10.17.

EXAMPLE XVII

Catalytic Hydrogenation of 3β-methylandrost-5-en-17-one

3β-Methylandrost-5-en-17-one (0.4 g, 1.4 mmol) was dissolved in acetic acid (80 ml). Palladium (10%) on carbon (100 mg) was added and the solution hydrogenated at atmospheric pressure until hydrogen uptake ceased. The solution was filtered through celite and evaporated to give a white solid (320 mg, 80%) which was recrystallized from methanol. HPLC and GC analyses showed 100% pure 3β-methyl-5α-androstan-17-one: mp 107°–108° C.; NMR (CDCl$_3$) δ 0.86 (d, J=9 Hz, 3H, C-3 Me), 0.85 (s, 3H, C-19 Me), 0.79 (s, 3H, C-18 Me); IR (KBr) 2920, 1740, 1445, 1365; MS 288 (M$^+$, 100) 273(18) 270(9) 255(14) 244(32), 217(17), 163(17), 123(40); Anal. Calcd for C$_{20}$H$_{32}$O: C, 83.26; H, 11.18. Found: C, 82.99; H, 11.35.

Similarly, by using the above procedure, the following compound were prepared from the corresponding 5-androstene compounds:

3α-Iodo-5α-androstan-17-one (56%)

mp 123°–125° C.; NMR (CDCl$_3$) δ 4.95 (br s, 1H, H-3β), 0.86 (s, 3H, C-19 Me), 0.83 (s, 3H, C-18 Me); IR (KBr) 2910, 2850, 1730, 1435, 1050; MS 400 (M$^+$, 1), 383(1), 308(1), 273(57), 255(42), 173(17), 93(66), 41(100); Anal. Calcd for C$_{19}$H$_{29}$OI: C, 57.00; H, 7.30. Found: C, 56.96; H, 7.35.

3βMethyl-5α-androstan-17-one (88%)

mp 107°–110° C.; NMR (CDCl$_3$) δ 0.85 (s, 3H, C-19 Me), 0.78 (s, 3H, C-18 Me), 0.87 (d, J=5 Hz, 3H, C-3 Me); identical by mixed melting point and GC to material prepared via DHEA route.

3β-Vinyl-5α-androstan-17-one (119) (90%)

mp 100.5°–101.5° C; NMR (CDCl$_3$) δ 5.77–4.93 (m, 3H, vinyl), 0.86 (s, 3H, C-19 Me), 0.80 (s, 3H, C-18 Me); IR (KBr) 2910, 1735, 1625, 1435; MS 300 (M$^+$, 100) 285 (24) 282 (46) 267 (19) 256 (18), 24 (10), 229 (10), 190 (10); Anal. Calcd for C$_{21}$H$_{32}$O: C, 83.94; H, 10.73. Found: C, 83.86; H, 10.62.

EXAMPLE VIII

16α-Hydroxy-3β-methylandrost-5-en-17-one

16α-Bromo-3β-methylandrost-5-en-17-one (1.00 g, 2.74 .mmol) was dissolved in dimethylformamide (90 mL). Sodium hydroxide (165 mg, 4.1 mmol) in water (10 mL) was added and the solution stirred for 2 h. at room temperature. The solution was poured into 1% HCl (200 mL) and extracted with ethyl acetate (2×50 mL). The organic layer was washed with 5% sodium biocarbonate, water, then dried over magnesium sulfate and filtered. Evaporation gave a pale yellow solid which was chromatographed on flash silica gel and eluted with ether/hexane (10/90). Recrystallization from ether gave 0.54 g (65%) 16α-hydroxy-3β-methylandrost-5-en-17-one mp 166°–168° C.; NMR (DMSO-d$_6$) δ 5.30 (br s, 1H, H-3), 4.38 (t, 1H, 16β-H), 2.0–1.05 (m, complex), 0.98 (s, 3H, C-19 Me), 0.95 (d, J=8 Hz, 3H, C-3 Me), 0.87 (s, 3H, C-18 Me); IR (KBr) 3440, 2900, 1735, 1445, 1365, 1010; MS 302 (m$^+$, 100), 287(24), 274(7), 259(7), 241(7), 230(72), 215(41), 159(31); Anal. Calcd for C$_{20}$H$_{30}$O$_2$: C, 79.42; H, 9.99. Found: C, 79.24; H, 10.04.

EXAMPLE XIX

3β,16α-Dimethylandrost-5-en-17-one

Diisopropyl amine (1.165 g, 11.5 mmol) was dissolved in dry tetrahydrofuran (30 mL) at −78° C. under N$_2$. n-Butyl lithium (4.44 mL of a 2.6M solution in hexane, 11.5 mmol) was added via syringe and the solution warmed to −23° C. (CO$_2$, CCl$_4$) for 0.25 h. 3β-Methylandrost-5-en-17-one (3.0 g, 10.4 mmol) in dry tetrahydrofuran (30 mL) was added via syringe and the solution stirred for 0.25 h. Methyl iodide (7.0 g, 49.33 mmol) in dry tetrahydrofuran (30 mL) was added dropwise and the mixture stirred at room temperature for 1.5 h. The solution was quenched with saturated ammonium chloride and the organic layer separated, dried over magnesium sulfate, filtered, and evaporated. The residual solid was chromatographed on flash silica gel (120 g) and eluted with 1/99 (v/v) ether hexane to give 3β,16α-dimethylandrost-5-en-17-one (2.32 g, 74%). mp 109°–110° C. (recrystallized from methanol); NMR (CDCl$_3$) δ 5.29 (br s, J=5 Hz, 1H, H-6), 2.52 (m, 1-H, H-16), 1.07 (d J=8 Hz, 3H, C-16 Me), 0.99 (s, 3H, C-19 Me), 0.91 (s, 3H, C-18 Me); IR (KBr) 2900, 1730, 1450, 1430, 1370; MS 300 (M$^+$, 100), 285(62), 282(2), 272(12), 267(17), 229(20), 217(30), 159(17); Anal. Calcd for C$_{21}$H$_{32}$O: C, 83.93; H, 10.73. Found: C, 83.79; H, 10.52.

In order to determine the pharmacological activity of the novel and other steroids of the present invention, the following experiments were carried out. For comparative purposes, Androst-5-en-17-one 15 (Desoxy DHEA) was synthesized in accordance with T. Nambara and H. Takahaski, *Chem Pharm Bull Jap.*, 1970, 18, 2309 m.p. 106° (lit. value 108°–109° C.)

Inhibition of G6PDH

The compounds listed below are screened as inhibitors of purified bovine adrenal G6PDH activity as one predictor of cancer preventive action. The assay for testing the inhibition of purified bovine adrenal G6PDH is according to the procedure by Oertel, G. W. and Rebelein, I. in Biochem. Biophys. Acta, 184, 459–460 (1969). The results are given below in Table I:

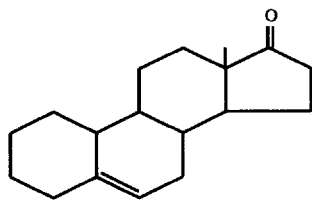

15

TABLE I

| G6PDH INHIBITION TEST | | | |
|---|---|---|---|
| Compound | No. | Conc. | Per Cent Inhibition |
| (structure) | 1 | 10 μm | 53 |
|  |  | 1 μm | 36 |
|  |  | 0.1 μm | 12 |
| (structure) | 2 | 10 μm | 82 |
|  |  | 1 μm | 64 |
|  |  | 0.1 μm | 36 |
| (structure) | 3 | 10 μm | 80 |
|  |  | 1 μm | 69 |
|  |  | 0.1 μm | 10 |
| (structure) | 4 | 10 μm | 90 |

TABLE I-continued

G6PDH INHIBITION TEST

| Compound | No. | Conc. | Per Cent Inhibition |
|---|---|---|---|
| (3-HO, Δ5, 17-one, 16α-Br steroid) | 5 | 10 μm | 74 |
| (3-HO, 5α-H, 17-one, 16α-Cl steroid) | 6 | 10 μm | 72 |
| (3-HO, 5α-H, 17-one, 16α-I steroid) | 7 | 10 μm | 51 |
| (3-HO, 5α-H, 17-one, 16α-F steroid) | 8 | 10 μm | 66 |
| (3-F, Δ5, 17-one steroid) | 9 | 10 μm | 22 |
| (3-HO, 5α-H, 17-one steroid) | 10 | 10 μm | 35 |
| (3-HO, 4-CH3, 5α-H, 17-one steroid) | 11 | 10 μm | 35 |

TABLE I-continued

G6PDH INHIBITION TEST

| Compound | No. | Conc. | Per Cent Inhibition |
|---|---|---|---|
| (structure: 3β-OH, 4α-CH₃, Δ5, 17-one steroid) | 11a | 10 μM<br>1 μm | 87<br>72 |
| (structure: 3-OH, 4,4-diCH₃, Δ5, 17-one steroid) | 12 | 10 μm | 48 |
| (structure: 3β-C₂H₅, Δ5, 17-one steroid) | 13 | 10 μm<br>1 μm<br>0.1 μm | 73<br>55<br>58 |
| (structure: Δ5, 17-one steroid, no 3-substituent) | 14 | 10 μm<br>1 μm<br>0.1 μm | 73<br>30<br>— |
| (structure: 2α-CH₃, 3-OH, Δ5, 17-one steroid) | 15 | 10 μm<br>1 μm<br>0.1 μm | 46<br>40<br>26 |
| (structure: 3β-CH₃, Δ5, 17-one steroid) | 16 | 10 μm<br>1 μm<br>0.1 μm | 53<br>40<br>25 |

TABLE I-continued
G6PDH INHIBITION TEST
| Compound | No. | Conc. | Per Cent Inhibition |
|---|---|---|---|
| 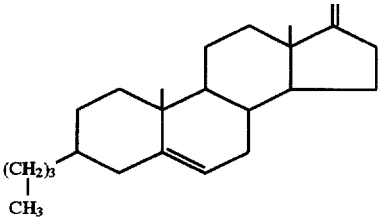 | 17 | 10 μm<br>1 μm<br>0.1 μm | 60<br>45<br>49 |
| 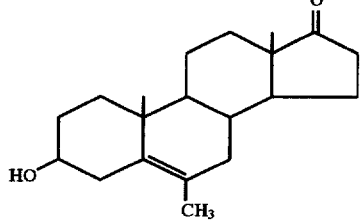 | 18 | 10 μm<br>1 μm<br>0.1 μm | 45<br>18<br>10 |
| DHEA | 1 | 10 μm<br>1 μm | 51, 52<br>20, 23 |
| 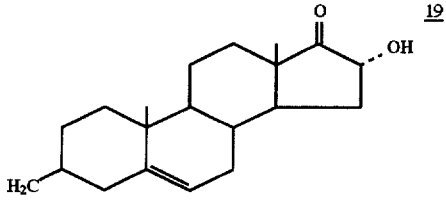 | 19 | 10 μm<br>1 μm | 64, 67<br>29, 27 |
| 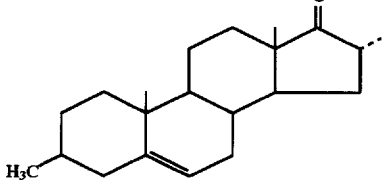 | 20 | 10 μm<br>1 μm | 46, 52<br>55, 56 |
| DHEA | 1 | 10 μm<br>1 μm | 58, 57<br>24, 27 |
| 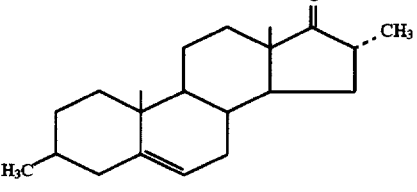 | 21 | 10 μm<br>1 μm | 48, 55<br>36, 42, 31, 41 |
| DHEA | 1 | 10 μm<br>1 μm | 53, 57<br>17, 17 |
| 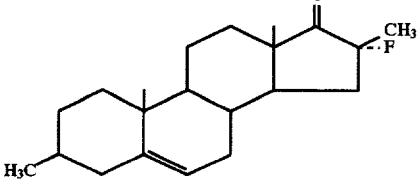 | 22 | 10 μm<br>1 μm | 65, 71<br>53, 63 |

Inhibition of TPA (Tumor Promoter) Stimulation of Mouse Epidermal DNA

Synthesis rate by orally administered steroids

The inhibition of tumor promoter stimulation of mouse epidermal DNA synthesis rate by steroids may also contribute to cancer preventive activity. The following assay is used:

ICR male mice (7–9 weeks old) were shaved on the back 1–2 days before use. Only mice showing no hair regrowth were used. Animals were orally intubated with a particular steroid suspended by homogenization in sesame oil or with sesame oil alone (controls). One hour later TPA (10 µg in 0.2 ml of acetone) or acetone vehicle was applied topically to the shaved skin. Twenty hours later, mice were injected i.p. with 60 µCi of $^3$H-thymidine 20 minutes before sacrifice. The animals were killed by cervical dislocation and the residual hair was removed with a depilatory agent. Epidermal scrapings were prepared according to the procedures of Hennings et al. (Cancer Res. 28, 53, 1968), homogenized in distilled water at 4° C., and the macromolecules precipitated with 0.4N trichloroacetic acid (TCA). Following 6 washes with absolute ethanol at room temperature, the nucleic acids were hydrolyzed with 0.5N TCA at 70° C. for 5 minutes. The hydrolysate (0.2 ml aliquots) were counted in an Intertechnique scintillation counter and assayed for DNA by the diphenylamine reaction.

The data are expressed as counts per minute (cpm) of tritium per µg of DNA.

|  | cpm/µg DNA |
|---|---|
| Control (no TPA and no steroid) | 37 ± 6.1 (number (n) of animals = 3) |
| TPA | 101 ± 20 |
| TPA + DHEA (compound 1)* (400 mg/kg) | 42 ± 7 |
| TPA + DHEA (200 mg/kg) | 88 ± 9.3 |
| TPA + DHEA (100 mg/kg) | 87 ± 8.2 |
| TPA + Compound 2* (200 mg/kg) | 100 ± 6.0 |
| TPA + Compound 2* (100 mg/kg) | 97 ± 15 |
| TPA + Compound 3* (200 mg/kg) | 64 ± 10 |
| TPA + Compound 3* (100 mg/kg) | 113 ± 21 |

*of Table 1

Conclusion

DHEA is active at blocking the TPA stimulation in DNA synthesis rate at 400 mg/kg but not at 200 mg/kg or 100 mg/kg. Compound 2 is not active at 200 mg/kg or 100 mg/kg. Other tests in which compound 2 or compound 3 and DHEA were given by i.p. injection in a dose-response experiment indicated that 2 is about as active as DHEA and compound 3 was more active in blocking the TPA stimulation in DNA synthesis rate.

Compound 3 appears somewhat more active than DHEA at the dose of 200 mg/kg administered orally.

Compound 2 or 3 in comparison with DHEA by Intraperitoneal Injection.

Steroids were suspended in sterile 95% saline—5% Emulphor and injected intraperitoneally. Otherwise conditions were the same as when steroids were orally administered.

| Compound 2 vs. DHEA | cpm/µg DNA |
|---|---|
| Control (no steroid or TPA) | 63 ± 3.9 (n = 2) |
| TPA | 170 ± 2.2 |
| DHEA (10 mg/kg i.p.) + TPA | 66 ± 2.1 |
| DHEA (2 mg/kg i.p.) + TPA | 105 ± 12 |
| DHEA (0.4 mg/kg i.p.) + TPA | 157 ± 4.2 |
| Cpd 2 (10 mg/kg i.p.) + TPA | 58 ± 0.9 |
| Cpd 2 (2 mg/kg i.p.) + TPA | 94 ± 1.3 |
| Cpd 2 (0.4 mg/kg i.p.) + TPA | 148 ± 3.0 |

| Compound 3 vs. DHEA | cpm/µg DNA |
|---|---|
| Control (no steroid or TPA) | 46 ± 5.3 |
| TPA | 114 ± 37 |
| Cpd 3 (10 mg/kg i.p.) + TPA | 8.9 ± 3.0 |
| Cpd 3 (2 mg/kg i.p.) + TPA | 27 ± 8.8 |
| Cpd 3 (0.4 mg/kg i.p.) + TPA | 32 ± 2.4 |

Compound 16* vs. DHEA

A similar oral dose-response experiment with compound 16 and DHEA was performed.

|  | cpm/µg DNA |
|---|---|
| Control (no TPA, no steroid) | 55 ± 3.7 (n = 2) |
| TPA | 162 ± 2.1 |
| TPA + DHEA (400 mg/kg) | 50 ± 2.8 |
| TPA + DHEA (200 mg/kg) | 155 ± 1.6 |
| TPA + DHEA (100 mg/kg) | 169 ± 11 |
| TPA + Compound 16* (400 mg/kg) | 39 ± 1.1 |
| TPA + Compound 16* (200 mg/kg) | 44 ± 2.5 |
| TPA + Compound 16* (100 mg/kg) | 100 ± 19 |

*of Table I
Conclusion: Compound 16 is about 3X as active as DHEA in this test.

Both of the above tests, i.e., the inhibition of mammalian glucose-6-phosphate dehydrogenase (G6PDH) and the inhibition of tumor promoter (TPA) stimulation of $^3$H-thymidine incorporation in mouse epidermis are recognized as indicators of cancer prophylactic activity. The following Table compares the efficacy of representative compounds of the present invention in these two tests with that of DHEA:

TABLE 3

| | G6PDH Inhibition | Inhibition of TPA Effect on Epidermis Following Oral Administration |
|---|---|---|
| DHEA | 1X | 1X |
| 3β-hydroxy-5α-androstan-17-one | ~1.5X | ~1X |
| 5α-androstan-17-one | >2X | ~1.5X |
| DHEA | 1X | 1X |
| 3β-methyl-androst-5-en-17-one | ~1X | 3X |
| 3β,16α-dimethyl-androst-5-en-17-one | ~0.5X | not tested |
| 16α-hydroxy-3β-methyl-androst-5-en-17-one | ~2X | 5X |
| 3β-chloro-androst-5-en-17-one | 0.5X | 1–1.5X |
| DHEA | 1X | 1X |

TABLE 3-continued

| | G6PDH Inhibition | Inhibition of TPA Effect on Epidermis Following Oral Administration |
|---|---|---|
| 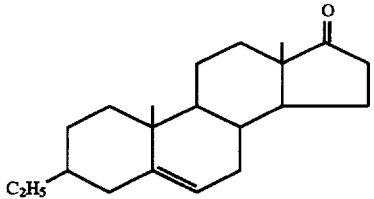 | ~1.5X | not tested |
| 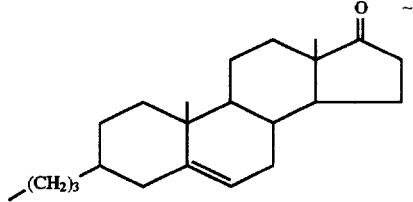 | ~2X | not tested |
| 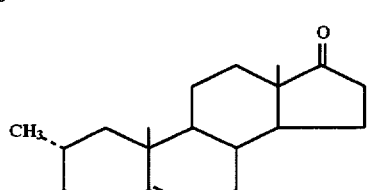 | ~1X | not tested |
| 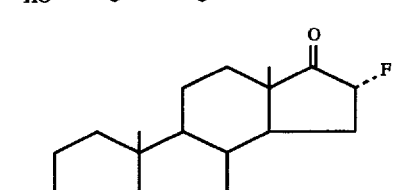 | ~5–10X | >10x (most active compound) |

BACKGROUND INFORMATION ON ACTIONS OF DMBA AND TPA

Skin tumors can be induced in the mouse either by weekly application of a carcinogen such as 7,12-dimethylbenzylanthracene (DMBA), or alternatively, by a single sub-threshold dose of the carcinogen followed by twice weekly applications of the tumor promoter tetradecanoylphorbol-13-acetate (TPA). In order to exert its carcinogenic effect, DMBA must be metabolized by an NADPH-dependent mixed-function oxidase to chemically reactive intermediates which bind covalently to DNA and produce mutations leading to malignant transformation. Dehydroepiandrosterone (DHEA) and 3β-methylandrost-5-en-17-one inhibit 7,12-dimethylbenz(a)anthracene (DMBA)-initiated and 12-O-tetradecanoylphorbol-13-acetate (TPA)-promoted skin papilloma formation in mice, Carcinogenesis, 5, 464–466 and DHEA inhibits the rate of binding of topically applied $^3$H-DMBA to A/J mouse skin DNA (Table 4). The potent androgen, testosterone, is without inhibitory effect. This effect of DHEA very probably is a result of the inhibition of G6PDH and lowering of the intracellular pool of NADPH, which is a co-factor for the mixed-function oxidase activation of DMBA. Topical DHEA or 3β-methylandrost-5-en-17-one application also inhibits DMBA produced papillomas and carcinomas in the complete carcinogenesis model (Pashko, L. L. Hard, G. C.; Rovito, R. J.; Williams, J. R.; Sobel, E. L.; and Schwartz, A. G. (1985). Inhibition of 7,12-dimethylbenz(a)anthracene induced skin papillomas and carcinomas by dehydroepiandrosterone and 3β-methylandrost-5-en-17-one in mice, Cancer Res., 45, 164–166).

Tumor promoters, such as TPA, stimulate hyperplasia and DNA synthesis when applied to the skin, and it is believed that this stimulation is an important step in the enhancement of tumorigenesis. This stimulation of epidermal DNA synthesis rate by TPA can be demonstrated by an enhanced rate of $^3$H-thymidine incorporation in mouse epidermis 20 hours after TPA application. Again, topical DHEA treatment abolishes this stimulation (Table 5).

The inhibition of the TPA stimulation of epidermal $^3$H-thymidine incorporation by DHEA may also result from G6PDH inhibition. The pentose-phosphate pathway provides both ribose-phosphate for ribonucleotide synthesis as well as NADPH which is needed both for the reduction of folic acid to tetrahydrofolic acid (required for ribonucleotide and thymidylate synthesis) as well as for the activity of ribouucleotide reductase. DHEA, over a range of $10^{-5}$M to $10^{-4}$M, slows the growth of many different cell lines in culture. One HeLa cell strain, TCRC-2, is particularly sensitive to DHEA-induced growth inhibition. This growth inhibition can be almost completely overcome by adding to the culture medium a mixture of the deoxynucleosides of adenine, guanine, cytosine, and thymine, which is consistent with the hypothesis that DHEA inhibits cell growth through G6PDH inhibition (Dworkin, C. R., Gorman, S. D., Pashko, L. L., Cristofallo, V. J. and Schwartz, A. G. (1986). Inhibition of growth of HeLa and WI-38 cells by dehydroepiandrosterone and its reversal by ribo-and deoxyribounucleosides, Life Sci., 38, 1451–1457).

FOOD RESTRICTION AND CANCER PREVENTION

It has been known for 45 years that reducing the food intake of laboratory mice inhibits the development of a broad spectrum of spontaneous and chemically induced tumors (Tannenbaum, A. (1940); The Inhibition and Growth of Tumors. Introduction. I. Effects of Underfeeding, Am. J. Cancer, 38, 335–350), but the mechanism of this effect is not clear. It appears that food restriction of mice for two weeks inhibits both the binding of $^3$H-DMBA to skin DNA as well as the TPA stimulation of epidermal $^3$H-thymidine incorporation (Tables 4 and 6) to a degree comparable to that observed with an application of 400 ug of DHEA. Both these effects of food restriction very likely result from a depression in G6PDH activity (Table 7). Thus inhibition of G6PDH activity may be an important component in the cancer preventive effects of both food restriction and DHEA treatment.

Administration of DHEA at a daily dose of approximately 400 mg/kg in long-term experiments has been shown to inhibit the development of breast, lung, and colon tumors. This dose of DHEA, when administered repeatedly over a period of a few weeks, also produces an anti-weight effect. However, a single administration of DHEA at 400 mg/kg to mice does not inhibit $^3$H-DMBA binding to skin DNA and does not inhibit the TPA stimulation in epidermal $^3$H-thymidine incorporation to a degree comparable to that produced by either food restriction or a topical application of 400 ug of DHEA. (Tables 8&9 vs. Tables 4,5&6) However, treatment of mice for four weeks with 400 mg/kg of DHEA does inhibit $^3$H-DMBA binding to skin DNA, but this regimen of DHEA treatment also produces an anti-weight effect, which is due to both a reduction in food intake and to a decrease in the efficiency of food utilization. Thus the cancer preventive effect of DHEA may result indirectly from its anti-weight action rather than from a direct effect of DHEA or target cells.

However, compounds 19 and 20, when administered orally to mice, inhibit $^3$H-DMBA binding to skin DNA and TPA stimulation in $^3$H-thymidine incorporation to a degree comparable to that produced by food restriction at doses well below 400 mg/kg, whereas DHEA is inactive. (Tables 8, 9, 10, 11 and 12) At these dosages the new compounds do not produce an anti-weight effect. Therefore, the cancer preventive activities of the present compounds are more potent than the cancer preventive activity of DHEA, and in addition, the cancer preventive activity of the present new steroids has been dissociated from the anti-obesity effect.

TABLE 4

EFFECT OF STEROID TREATMENT OR TWO WEEKS OF FOOD RESTRICTION ON ($^3$H) DMBA BINDING TO SKIN DNA

| TREATMENT | SPECIFIC ACTIVITY (cpm/ug DNA) |
|---|---|
| Ad libitum fed | 116 ± 5.2 |
| Ad libitum fed plus DHEA | 66 ± 13 |
| Ad libitum fed plus testosterone | 164 ± 8.4 |
| Food restricted (two weeks) | 57 ± 14 |

Binding of [$^3$H]DMBA to mouse skin DNA was determined as described in Pashko, L. L., and Schwartz, A. G. (1983), Effect of food restriction, dehydroepiandrosterone, or obesity on the binding of $^3$H-7 12-dimethylbenz(a) anthracene to mouse skin DNA, J. Gerontol., 38, 8–12. Values are mean±SD for 3 individual determinations, with pooled tissue from 2 mice used for each determination. DHEA or testosterone (400 ug in 0.2 ml acetone) was applied to the skin one hour before [$^3$H]DMBA. The mean weight of the food restricted mice was 18.5±1.0 gm, n=6, of the ad libitum fed, 27.4±1.0 gm, n=6, of the ad libitum fed treated with DHEA, 28.2±0.9 gm, n=6, and of the ad libitum fed treated with testosterone, 28.3±0.9 gm, n=6, following two weeks of feeding. The average food consumed was, in gm/mouse/day, 2.2, 3.8, 3.8 and 4.0 for the food restricted, ad libitum fed, ad libitum fed plus DHEA, and ad libitum fed plus testosterone groups, respectively.

*Significantly less than ad libitum fed mice, p<0.01;

**Significantly greater than ad libitum fed mice, p<0.01.

TABLE 5

INHIBITION OF TPA STIMULATION OF $^3$H-THYMIDINE INCORPORATION IN EPIDERMIS BY DHEA

| TREATMENT | SPECIFIC ACTIVITY (cpm/ug DNA) |
|---|---|
| No steroid | 66 ± 1.8 |
| No steroid plus TPA | 174 ± 35 |
| TPA plus DHEA (100 ug) | 52 ± 5.8 |
| TPA plus DHEA (400 ug) | 22 ± 6.5 |
| TPA plus testosterone (100 ug) | 128 ± 13 |
| TPA plus testosterone (400 ug) | 142 ± 5.9 |

Incorporation of $^3$H-thymidine into A/J mouse epidermal DNA was determined as described in Pashko, L. L., Schwartz, A. G., Abou-Gharbia, M. and Swern, D. (1981), Inhibition of DNA synthesis in mouse epidermis and breast epithelium by dehydroepiandrosterone and related steroids, Carcinogenesis, 2, 717–721. Values are mean±SD for 3 separately treated mice in each group 20 hours after TPA application. DHEA or testosterone was added topically in 0.2 ml acetone one hour before TPA addition.

TABLE 6

EFFECT OF TWO WEEKS OF FOOD RESTRICTION ON TPA STIMULATION OF EPIDERMAL $^3$H-THYMIDINE INCORPORATION

| TREATMENT | SPECIFIC ACTIVITY (cpm/ug DNA) |
|---|---|
| Ad libitum fed | 54 ± 0.8 |
| Ad libitum fed plus TPA | 193 ± 25 |
| Food restricted (two weeks) plus TPA | 34 ± 6.8 |

Incorporation of $^3$H-thymidine into A/J mouse epidermal DNA was determined as described in Table 5. Values are mean±SD for 3 separately treated mice in each group. The mean weight of the food restricted mice was 18.3±0.6 gm n=3, and of the ad libitum fed was 26.7±1.4, n=6, following two weeks of feeding. The average food consumed was 2.4 gm/mouse/day for food restricted and 4.9 gm/mouse/day for ad libitum fed mice.

TABLE 7

EFFECT OF TWO WEEKS OF FOOD RESTRICTION ON EPIDERMAL G6PDH ACTIVITY

| TREATMENT | SPECIFIC ACTIVITY (nmoles NADPH/mg protein min) |
|---|---|
| Ad libitum fed | 43.4 ± 6.0 |
| Food restricted (two weeks) | 18.1 ± 5.1 |

Epidermal G6PDH activity was determined as described in Ziboh, V. A., Dreize, M. A., and Hsia, S. L. (1970), Inhibition of lipid synthesis and glucose-6-phosphate dehydrogenase in rat skin by dehydroepiandrosterone, *J. Lipid Res.*, 11, 346–351 and Glock, G. E. and McClean, P. (1953). Further studies on the properties of glucose-6-phosphate dehydrogenase and 6-phosphogluconate dehydrogenase of rat liver, *Biochem. J.*, 55, 400–408. Values are mean±SD for three separate determinations, with pooled epidermal tissue from 4 mice used for each determination. The mean weight of the food restricted mice was 18.4±0.8 gm, n=12. The average food consumed was 2.4 gm/mouse/day for food restricted and 3.9 gm/mouse/day for the ad libitum fed mice.

TABLE 8

Effect of Orally Administered DHEA or 19 on TPA Stimulation of $^3$H-Thymidine Incorporation in Mouse Epidermis

| TREATMENT | SPECIFIC ACTIVITY (cpm/ug DNA) |
|---|---|
| No steroid | 58.1 ± 6.7 (n = 3) |
| No steroid plus TPA | 155 ± 13.8 (n = 3) |
| TPA plus DHEA (400 mg/kg p.o.) | 59.5 ± 5.4 (n = 2) |
| TPA plus DHEA (200 mg/kg p.o.) | 118 ± 4.5 (n = 3) |
| TPA plus 19 (400 mg/kg p.o.) | 2.1 ± 3.0 (n = 3) |
| TPA plus 19 (200 mg/kg p.o.) | 6.9 ± 2.3 (n = 3) |

Male ICR mice were orally intubated with steroid suspended in sesame oil (0.5 ml/mouse) at the indicated dose. Mice not receiving steroid were given sesame oil alone. One hour later mice received topical application of TPA and 20 hours later the rate of $^3$H-thymidine incorporation into the epidermis was determined as described in Table 4.

TABLE 9

Effect of Orally Administered DHEA, 19, or two weeks of Food Restriction on [$^3$H] DMBA Binding to Skin DNA

| TREATMENT | SPECIFIC ACTIVITY (cpm/ug DNA) |
|---|---|
| No steroid | 65.7 ± 9.6 (n = 3) |
| DHEA (400 mg/kg, p.o.) | 73.1 ± 16.5 (n = 3) |
| 19 (400 mg/kg, p.o.) | 20.4 ± 1.1 (n = 3) |
| No steroid, Food restricted | 32.3 ± 3.5 (n = 3) |

Male A/J mice were orally intubated with steroid suspended in sesame oil (0.5 ml/mouse) at the indicated dose. Mice not receiving steroid were given sesame oil alone. Food restricted mice received approximately 60% of food of Ad libitum fed for two weeks. One hour after oral intubation, topical [$^3$H]DMBA was applied to the skin, and the amount bound to DNA was determined 12 hours later as described in Table 4.

TABLE 10

Effect of Orally Administered 19 or 20 on TPA Stimulation of $^3$H-Thymidine Incorporation in Mouse Epidermis

| TREATMENT | SPECIFIC ACTIVITY (cpm/ug DNA) |
|---|---|
| TPA plus 19 (150 mg/kg, p.o.) | 14.9 ± 2.6 (n = 3) |
| TPA plus 19 (100 mg/kg, p.o.) | 57 ± 7.9 (n = 3) |
| TPA plus 19 (50 mg/kg, p.o.) | 171 ± 19 (n = 3) |
| TPA plus 20 (150 mg/kg, p.o.) | 11 ± 2.2 (n = 3) |
| TPA plus 20 (100 mg/kg, p.o.) | 13.6 ± 2.4 (n = 3) |
| TPA plus 20 (50 mg/kg, p.o.) | 16.3 ± 1.6 (n = 3) |

Male ICR mice were orally intubated with steroid suspended in sesame oil (0.5 ml/mouse) at the indicated dose. Mice not receiving steroid were given sesame oil alone. One hour later mice received topical application of TPA, and 20 hours later the rate of $^3$H-thymidine incorporation into the epidermis was determined as described in Table 4.

TABLE 11

Effect of Orally Administered DHEA or 20 on [$^3$H] DMBA Binding to Skin DNA

| TREATMENT | SPECIFIC ACTIVITY (cpm/ug DNA) |
|---|---|
| No steroid | 142 ± 5.9 (n = 3) |
| DHEA (400 mg/kg, p.o.) | 92 ± 17.6 (n = 3) |
| 20 (200 mg/kg, p.o.) | 43.7 ± 1.5 (n = 3) |
| 20 (100 mg/kg, p.o.) | 48.4 ± 2.6 (n = 3) |

Male A/J mice were orally intubated with steroid suspended in sesame oil (0.5 ml/mouse) at the indicated dose. Mice not receiving steroid were given sesame oil alone. One hour after oral intubation, topical [$^3$H]DMBA was applied to the skin, and the amount bound to DNA was determined 12 hours later as described in Table 4.

TABLE 12

Effect of Orally Administered 19 on TPA Stimulation of $^3$H-Thymidine Incorporation in Mouse Epidermis

| TREATMENT | SPECIFIC ACTIVITY (cpm/ug DNA) |
|---|---|
| TPA plus 19 (200 mg/kg, p.o.) | 10.5 ± 1.6 (n = 3) |
| TPA plus 19 (150 mg/kg, p.o.) | 13.7 ± 1.7 (n = 3) |
| TPA plus 19 (75 mg/kg, p.o.) | 23.6 ± 1.2 (n = 3) |

Experimental conditions are the same as in Table 5.

Anti-Obesity Test

Male A/J mice (5 weeks old) were obtained from the Jackson Laboratory and were housed in polycarbonate cages (5 mice/cage) in animal quarters maintained at 24°±1° C. with 12 hours of light and 12 hours of darkness each day. One week after arrival, the mice were placed on a chow diet containing varying concentrations of DHEA or other steroid. Animals were weighed weekly; food consumption was determined weekly by subtracting the amount of food remaining in the cage from the amount added.

| | Compound 3 vs. DHEA | | |
|---|---|---|---|
| Week | Control (no steroid) | mean weekly weight in grams (n = 5) DHEA 0.7% | Cpd 3 0.35% | Cpd 3 0.7% |

| Week | Control (no steroid) | DHEA 0.7% | Cpd 3 0.35% | Cpd 3 0.7% |
|---|---|---|---|---|
| 0 | 21.6 ± 2.6 | 21.1 ± 2.8 | 21.8 ± 2.2 | 21.6 ± 2.6 |
| 1 | 22.6 ± 2.1 | 15.2 ± 1.8 | 22.6 ± 1.8 | 20.0 ± 1.9 |
| 2 | 23.4 ± 1.8 | 17.0 ± 2.0 | 23.6 ± 1.8 | 21.3 ± 1.8 |
| 3 | 24.6 ± 2.3 | 17.8 ± 1.1 | 24.8 ± 1.8 | 21.8 ± 1.6 |
| 4 | 25.4 ± 2.5 | 18.8 ± 1.1 | 24.6 ± 1.8 | 22.0 ± 1.6 |
| 5 | 26.0 ± 2.3 | 18.2 ± 1.3 | 24.8 ± 1.9 | 21.4 ± 1.1 |

There was an initial depression in food consumption in the DHEA treated mice in the first week. Thereafter the food consumption was equal to or slightly greater than the control mice.

| | | Compound 2 vs. DHEA | | |
|---|---|---|---|---|
| Week | Control | DHEA 0.35% | DHEA 0.7% mean weekly weight in grams (n= 5) | Cpd 2 0.35% | cpd 2 0.7% |

| Week | Control | DHEA 0.35% | DHEA 0.7% | Cpd 2 0.35% | cpd 2 0.7% |
|---|---|---|---|---|---|
| 0 | 21.6 ± 1.3 | 21.8 ± 2.2 | 22.0 ± 2.5 | 21.8 ± 1.6 | 21.3 ± 1.8 |
| 1 | 21.4 ± 2.1 | 20.0 ± 2.3 | 17.0 ± 1.9 | 21.8 ± 1.3 | 20.6 ± 2.3 |
| 2 | 22.0 ± 0.7 | 19.2 ± 1.8 | 17.8 ± 1.8 | 22.0 ± 1.2 | 20.6 ± 0.5 |
| 3 | 22.2 ± 0.8 | 19.6 ± 2.8 | 18.4 ± 1.8 | 22.8 ± 1.3 | 20.8 ± 0.8 |
| 4 | 24.0 ± 1.0 | 22.2 ± 2.4 | 19.2 ± 1.6 | 24.2 ± 1.1 | 22.6 ± 0.6 |
| 5 | 24.8 ± 0.8 | 21.8 ± 2.2 | 20.2 ± 1.9 | 24.4 ± 1.7 | 22.4 ± 0.5 |
| 6 | 25.2 ± 1.1 | 22.8 ± 2.3 | 19.8 ± 2.0 | 24.8 ± 1.5 | 23.5 ± 0.9 |
| 7 | 25.6 ± 1.1 | 23.2 ± 2.4 | 20.6 ± 2.2 | 25.4 ± 1.7 | 23.8 ± 0.8 |

| | Compound 16 vs. DHEA | | | |
|---|---|---|---|---|
| Week | Control | DHEA 0.18% | DHEA 0.35% mean weekly weight in grams (n = 5) | Cpd 16 0.18% | Cpd 16 0.35% |

| Week | Control | DHEA 0.18% | DHEA 0.35% | Cpd 16 0.18% | Cpd 16 0.35% |
|---|---|---|---|---|---|
| 0 | 21.6 ± 2.8 | 22.4 ± 1.8 | 22.4 ± 2.3 | 22.6 ± 2.7 | 22.0 ± 2.5 |
| 1 | 23.0 ± 1.6 | 20.4 ± 1.9 | 16.0 ± 1.6 | 19.8 ± 2.3 | 16.8 ± 1.6 |
| 2 | 24.4 ± 1.6 | 21.1 ± 0.5 | 20.2 ± 1.9 | 19.4 ± 2.1 | 18.2 ± 0.8 |
| 3 | 25.6 ± 1.9 | 22.4 ± 0.8 | 21.0 ± 0.8 | 19.4 ± 2.1 | 17.2 ± 1.7 |
| 4 | 26.6 ± 1.5 | 23.6 ± 1.5 | 22.2 ± 0.9 | 19.6 ± 2.2 | 17.0 ± 1.2 |

Compound 16 is more than 2× as active as DHEA in this test.

TABLE 13

ANTI-OBESITY ACTION OF 19 AND DHEA

Male A/J (5 weeks old) were obtained from the Jackson Laboratory and were housed in polycarbonate cages (5 mice/cage) in animal quarters maintained at 24°±1° C. with 12 hours of light and 12 hours of darkness each day. One week after arrival, the mice were placed on a diet containing either DHEA, 19, or without steroid. Animals were weighed weekly. The concentration of DHEA or 19 used in the food was 0.54%.

| Week | Control (no steroid) | DHEA | 19 |
|---|---|---|---|
| 0 | 20.5 ± 1.1 | 21.2 ± 1.4 | 21.1 ± 0.8 |
| 1 | 20.8 ± 0.8 | 16.8 ± 1.6 | 19.1 ± 0.9 |
| 2 | 22.7 ± 1.1 | 16.7 ± 2.0 | 18.4 ± 1.0 |
| 3 | 23.9 ± 1.9 | 18.8 ± 1.1 | 18.7 ± 1.4 |
| 4 | 23.5 ± 1.8 | 19.0 ± 2.0 | 19.7 ± 1.1 |
| 5 | 24.8 ± 1.4 | 19.6 ± 2.8 | 20.6 ± 0.4 |

Anti-obesity Action

Male A/J mice (5 weeks old) were obtained from the Jackson Laboratory and were housed in polycarbonate cages (5 mice/cage) in animal quarters maintained at 24°±1° C. with 12 hours of light and 12 hours of darkness each day. One week after arrival, the mice were placed on a show diet containing DHEA, 16, or 21 at 0.36%. Animals were weighed weekly.

| | mean weekly weight in grams ± S.D. (n = 5) | | |
|---|---|---|---|
| Week | Control (no steroid) | DHEA | 16 | 21 |

| Week | Control (no steroid) | DHEA | 16 | 21 |
|---|---|---|---|---|
| 0 | 22.4 ± 2.2 | 23.2 ± 1.3 | 23.3 ± 2.5 | 22.7 ± 1.9 |
| 1 | 23.5 ± 2.2 | 21.8 ± 1.0 | 18 ± 1.5 | 20.1 ± 2.1 |
| 2 | 24.7 ± 2.5 | 20.8 ± 1.0 | 17.1 ± 1.6 | 19.9 ± 2.3 |
| 3 | 24.8 ± 2.2 | 21.4 ± 0.5 | 15.7 ± 1.3 | 22.2 ± 2.3 |

A comparison of the anti-obesity activity of representative compounds with that of DHEA is depicted below in Table 14:

TABLE 14

| Compound | Anti-obesity Activity |
|---|---|
| DHEA | 1X |
| 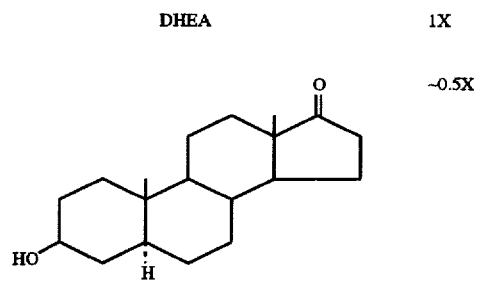 | ~0.5X |

TABLE 14-continued

| Compound | Anti-obesity Activity |
|---|---|
| (steroid structure with C=O at top, H at bottom) | ~0.5X |
| (steroid structure with C=O, CH₃, double bond) | ~3X |
| (steroid structure with C=O, OH, CH₃, double bond) | ~0.8X |
| (steroid structure with C=O, CH₃, CH₃, double bond) | ~1X |
| (steroid structure with C=O, Cl, double bond) | ~1X |
| (steroid structure with C=O, C₂H₅, double bond) | ~0.5X |

Anti-Hyperglycemic Activity

Coleman et al. (Diabetes 31, 830, 1982) reported that administration of DHEA (0.4% of the diet) produced a marked hypoglycemic effect in C57BL/KsJ-db/db mice and significantly prolonged their lifespan. The authors noted that "diabetes is more severe and develops more rapidly in males and can be improved or circumvented by combined estradiol and progesterone treatment" and suggested that the therapeutic effect of DHEA might result from its metabolism to estrogens. Compound 16 (which has been found herein to be devoid of estrogenic activity in the rat uterotrophic test) was tested in this model.

C57BL/KsJ-db/db 8 week old female mice were obtained and housed in polycarbonate cages in animal quarters maintained at 24° C. with 12 h of light and 12 h of darkness each day.

Mice were placed on a control chow or a chow diet containing either 0.4% DHEA or 0.2% of compound 16.

For determination of blood glucose levels, mice were bled from the orbital sinus using a heparinized capillary tube. 0.2 ml of blood was added to 1.8 ml of water to hemolyze the blood and glucose concentration was determined using the glucose oxidase assay.

| Blood Glucose Levels (mg/deciliter) | | | |
|---|---|---|---|
| Week | Control (n = 6) | DHEA (0.4%) (n = 6) | Cpd. 16 (0.2%) (n = 6) |
| 0 | 232 ± 43 | 232 ± 28 | 244 ± 32 |
| 1 | 336 ± 37 | 132 ± 14 | 143 ± 21 |
| 2 | 394 ± 20 | 135 ± 37 | 134 ± 13 |
| All mice placed on control diet. | | | |
| 24 hrs. | 399 ± 15 | 192 ± 32 | 147 ± 10 |
| 48 hrs. | 397 ± 13 | 310 ± 37 | 262 ± 23 |

When mice were taken off diets containing DHEA or compound 16 and placed on control diet, blood glucose level's increased at 24 and 48 hrs. but significantly more slowly in the mice that had received compound 16.

The following are additional data on the anti-hyperglycemic effect of compound 16 vs. DHEA.

| Blood Glucose Levels (mg/deciliter) | | | |
|---|---|---|---|
| Week | Control (n = 7) | DHEA (0.4%) (n = 7) | Cpd 16 (0.2%) (n = 7) |
| 0 | 213 ± 54 | 214 ± 59 | 216 ± 61 |
| 1 | 292 ± 29 | 161 ± 19 | 135 ± 15 |
| 2 | 335 ± 20 | 145 ± 19 | 118 ± 12 |
| 3 | 354 ± 27 | 117 ± 12 | 102 ± 8 |
| 4 | 387 ± 15 | 112 ± 4 | 105 ± 5 |

Compound 16 is more effective in lowering blood glucose concentration at an administered dose of 0.2% in the diet than is DHEA at a dose of 0.4%.

A comparison of the anti-diabetic activity of representative compounds with that of DHEA is depicted below in Table 15:

TABLE 15

| Compound | Anti-diabetic Activity |
|---|---|
| DHEA | 1X |
| [structure] | 3X |
| [structure] | 1X |

Anti-Autoimmune Activity

New Zealand Black (NZB) mice develop a progressive autoimmune, Coomb's positive hemolytic anemia with age. It has been previously found that long-term treatment of NZB mice with DHEA significantly inhibits the rate of development of the autoimmune anemia. In other studies reported herein, we have determined that certain steroids, such as compound 16, have retained the anti-obesity, cancer preventive, and anti-hyperglycemic action of DHEA without any apparent estrogenic effect. There is a reasonable probability that such steroids will also retain the anti-autoimmune activity of DHEA.

Anti-Hypercholesterolemic Activity

Six-week old female ICR mice were obtained and placed in animal quarters at 24° C. with 5 animals/cage with food and water ad libitum. All mice (except the control group) received 0.1% PTU (propylthiouracil) in their drinking water. Mice receiving DHEA or compound 4 were injected with the steroid i.p. (15 mg/kg) 3× weekly.

For serum cholesterol determinations, mice were bled from the orbital sinus. Blood was allowed to coagulate and was centrifuged to obtain serum. Cholesterol was measured according to the procedure of Rao et al. (Lipids 12, 1078, 1977).

| | | Serum Cholesterol (mg %) | | |
|---|---|---|---|---|
| Experimental Group | No. Mice | before treatment | 1 wk after treatment | 2 wk after treatment |
| Control (no steroid or PTU) | 30 | 53.8 ± 9.3 | 54.0 ± 4.0 | 59.2 ± 7.2 |
| PTU | 40 | 51.3 ± 6.1 | 75.6 ± 12.9 | 76.6 ± 2.4 |
| PTU + DHEA | 10 | 61.0 ± 6.8 | 57.3 ± 3.6 | 57.5 ± 3.2 |
| PTU + Cpd 4 | 10 | 58.1 ± 5.6 | 53.4 ± 5.2 | — |

Uterotrophic Test for Estrogenic Activity. Compound 16 vs. DHEA and Estradiol-benzoate. Compounds Given by Oral Administration.

Twenty-two day old rats were obtained from Charles River Laboratories. Animals were used at 29 days of age. Test steroids were suspended by homogenization in sesame oil. Rats were orally intubated at 1–2 P.M. for 3 days with a test steroid in sesame oil or with sesame oil alone (control). On the 4th day the animals were killed and the uteri were removed and weighed.

| | Mean Uterine Weight (Mgs) (n = 6) |
|---|---|
| Control (no steroid) | 166 ± 34 |
| DHEA (400 mg/kg) | 261 ± 23 (p < 0.001, greater than control) |
| Compound 16 (400 mg/kg) | 174 ± 20 |
| Compound 16 (200 mg/kg) | 189 ± 14 |
| Estradiol-benzoate (14 µg/kg) | 244 ± 44 (p < 0.01) |

Compound 2 vs. DHEA Compounds Administered by Subcutaneous Injection

Steroids were dissolved in 2 ml ethanol and brought up to 5 ml volume with propylene glycol. Concentrations were such that 1 µl/gm body weight delivered the indicated dose.

| | Mean Uterine Weight (Mgs) (n = 4 or 5) |
|---|---|
| Control (no steroid) | 152 ± 22 |
| DHEA (60 mg/kg) p < 0.02 | 290 ± 72 |
| DHEA (10 mg/kg) | 152 ± 17 |
| Compound 2 (60 mg/kg) | 127 ± 32 |
| Compound 2 (10 mg/kg) | 151 ± 32 |

The above test is being repeated at the oral dose of 400 mg/kg, which would have been more appropriate, since this is a therapeutic dose.

Conclusion

Neither compounds 16 nor 2 are estrogenic at doses at which DHEA is significantly estrogenic.

The compound 3β-methyl-5-androsten-17-one (cpd 16) was synthesized to overcome the estrogenic and possible androgenic effects of DHEA. DHEA injected at 60 mg/kg s.c. for 3 days into sexually immature rats produces uterine enlargement as a consequence of DHEA metablism into estrogens (Knudsen, T. T. and Makesh, V. B., 1975. Initiation of precocious sexual maturation in the immature rat treated with dehydroepiandrosterone, Endocrinology 97, 458). On the other band, injection of 16 results in a reduction in uterine weight.

EXPERIMENTAL DATA

Female CD rats, 26–27 days old, were used. Rats were injected subcutaneously for 3 days with either DHEA or 16 in propylene glycol. Control rats received propylene glycol alone. The rats were killed on the 4th day and the uteri were removed and weighed.

| Group | Mean Uterine Weight ± S.D. (mg/100 gm body weight) |
|---|---|
| Control | 195 ± 24 (n = 6) |
| DHEA (60 mg/kg) | 222 ± 77 (n = 6) |
| 16 (60 mg/kg) | 126 ± 87 (n = 6) |
| 16 (120 mg/kg) | 111 ± 27 (n = 6) |

Thus 16, when injected s.c. at a dose of 60 mg/kg or higher, apparently acts as an anti-estrogen.

ANTI-ANDROGENIC EFFECT OF 16

In addition to the anti-estrogenic action of 16, this steroid also has anti-androgenic properties. Treatment of male A/J mice with 16 for 4 weeks significantly reduced the weight of the seminal vesicles and prostate glands.

EXPERIMENTAL DATA

Male A/J mice (5 weeks old) were obtained from the Jackson Laboratory and were housed in polycarbonate cages (5 mice/cage) in animal quarters maintained at 24°±1° C. with 12 hours of light and 12 hours of darkness each day. One week after arrival, mice were placed on a chow diet containing either 0.18% or 0.09% 16 or without steroid. Mice were weighed weekly. After 4 weeks, the mice were killed, and the seminal vesicles plus prostate glands were dissected out and weighed.

| Group | Mean Seminal Vesicle plus Prostate Weight ± S.D. (mg/100 gm body weight) |
|---|---|
| Control | 5.5 ± 0.9 (n = 6) |
| 16 (0.09%) | 4.0 ± 0.7 (n = 6) |
| 16 (0.18%) | 3.4 ± 0.11 (n = 6) |

Both the anti-estrogenic and anti-androgenic activity of 16 would very likely make it unacceptable as a drug for humans.

Use of 16-Substituted Derivatives of DE-7 to Overcome Anti-Estrogenic and Anti-Androgenic Activities Because of the structural similarity between 16 and DHEA, it seemed reasonable that 16 might competitively inhibit the conversion of DHEA to 5-androsten-3,17-dione by the enzyme 3β-hydroxysteroid dehydrogenase. 5-Androsten-3,17-dione is a precursor to both testosterone and estrone. Thus 16 may competitively inhibit the conversion of endogenous DHEA into testosterone and estrone, and this may account for both the anti-estrogenic and anti-androgenic activity of this steroid.

In the paper entitled "Inhibitors of Human Placental $C_{19}$ and $C_{21}$ 3α-Hydroxysteroid Dehydrogenases" by A. S. Goldman and K. Sheth in *Biochimica biophysica Acta* 315, 253 (1973) a series of steroids were tested for their capacity to inhibit 3β-hydroxysteroid dehydrogenase. It was noted that either a 16αOH or 16 oxime substitution in the $\Delta^5$ androstene series or a 6βOH substitution in the $\Delta^4$ androstene series greatly reduced the capacity of the steroid in inhibiting the enzymatic conversion of DHEA into estrogens. Accordingly in order to overcome the anti-estrogenic and anti-androgenic activity of 16, the structure of compound 16 should be modified by the addition of substituents, such as OH, methyl, F, etc., in the 16α position.

Estrogenic and Anti-Estrogenic Activity

Female CD rats, 26–27 days old, were injected subcutaneously for 3 days with one of the compounds of the present invention at 60 mg/kg in propylene glycol. Controls received propylene glycol alone. On the 4th day the rats were killed and the uteri were dissected out and weighed. The results are given below:

ESTROGENIC AND ANTI-ESTROGENIC ACTIVITY

TABLE 16

Compound 21 was tested for estrogenic and anti-estrogenic action.

| Group | Mean Uterine weight ± S.D. (mg/100 gm body weight) |
|---|---|
| Control | 1.75 ± 0.5 (n = 6) |
| 16 | 1.28 ± 0.26 (n = 6) |
| 21 | 1.76 ± 0.21 (n = 6) |

The uterine weights/body weights of the cmpd. 16 treated rats were significantly greater than that of the cmpd. 21 treated rats (p<0.02).

ESTROGENIC AND ANTI-ESTROGENIC ACTIVITY TABLE 17

Compound 19 was tested for estrogenic and anti-estrogenic activity.

a. Activity in estrogen-anti-estrogen test

| Group | Mean Uterine Weight ± S.D. (mg/100 gm body weight) |
|---|---|
| Control | 2.22 ± 0.7 (n = 10) |
| 16 | 1.09 ± 0.24 (n = 9) |
| 19 | 2.16 ± 0.5 (n = 10) |

Cmpd. 19 shows no apparent estrogenic nor anti-estrogenic activity. On the contrary, cmpd. 16 gives highly significant anti-estrogenic activity.

ANDROGENIC AND ANTI-ANDROGENIC ACTIVITY (a) Male A/J mice (5 weeks old) were obtained from the Jackson Laboratory and were housed in polycarbonate cages (5 mice/cage) in animal quarters maintained at 24°±1° C. with 12 hours of light and 12 hours of darkness each day. One week after arrival, the mice were placed on a chow diet containing one of the test compounds of the present invention at 0.36%. After 4 weeks of treatment, the above mice were killed, and the seminal vesicles and prostate glands were dissected out and weighed.

| Group | Mean Seminal Vesicle plus Prostate Weight ± S.D. (mg/100 gm body weight) |
|---|---|
| Control | 6.2 ± 2.0 (n = 5) |
| DHEA | 6.5 ± 1.2 (n = 5) |
| 16 | 3.0 ± 0.3 (n = 5) |
| 21 | 5.1 ± 1.4 (n = 5) |

Cmpd. 16 treatment significantly reduced seminal vesicle plus prostate weight (p 0.05) whereas cmpd. 21 treatment did not.

ANDROGENIC AND ANTI-ANDROGENIC ACTIVITY con't.

| Group | Mean Seminal Vesicle plus Prostate Weight ± S.D. (mg/100 gm body weight) |
|---|---|
| Control | 6.32 ± 0.54 (n = 5) |
| DHEA | 5.02 ± 0.41 (n = 5) |
| 19 | 6.45 ± 0.65 (n = 5) |

Treatment of A/J mice for five weeks with 19 had no significant effect on seminal vesicle plus prostate gland weight. In numerous previous experiments treatment of A/J mice with 0.18% to 0.36% of 16 significantly reduced the seminal vesicle plus prostate gland weight. Interestingly, treatment with 0.54% of DHEA in this experiment also significantly reduced seminal vesical plus prostate gland weight (p<0.01). DHEA is both a potential androgen and estrogen, and conversion of DHEA into an estrogen could account for this effect. However, other mechanisms as well might produce this effect.

In conclusion, it appears that 19 and 21 have neither estrogenic, anti-estrogenic, androgenic, nor anti-androgenic activity, and are more effective inhibitors of G6PDH than is DHEA.

Using the protocols for Estrogenic and Anti-Estrogenic Activity and Androgenic and Anti-Androgenic Activity described hereinabove, it was determined that 3 chloro-5-androstene-17-one is also neutral steroid, i.e., it is without any demonstrable estrogenic, androgenic, anti-androgenic or anti-estrogenic activity.

Lack of Sex Steroid Hormonal or Anti-hormonal Activity

The following steroids have been tested and found to be neutral steroids, i.e., they were without demonstrable estrogenic, androgenic, anti-estrogenic, or anti-androgenic activity.

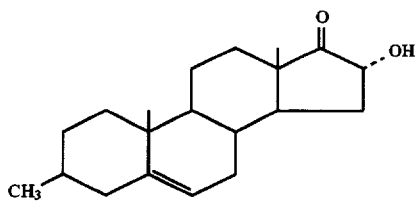

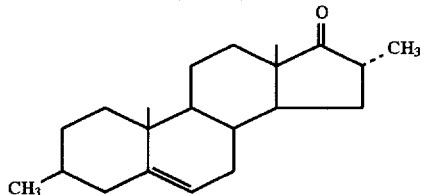

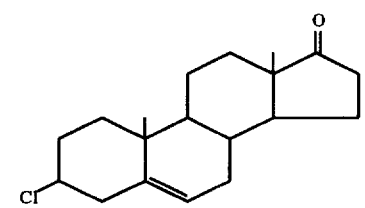

The compounds, i.e. therapeutic agents of this invention, may be administered alone or in combination with pharmaceutically-acceptable carriers, the proportion of which is determined by the solubility and chemical nature of the compound, chosen route of administration and standard pharmaceutical practice. For example, they may be administered orally in the form of tablets, pills or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

When given orally, the therapeutic doses of the compounds of the present invention are generally in the range of from about 4 to about 450 mg/kg/day depending upon the particular mammalian host and the particular effect desired, e.g. cancer preventive, anti-obesity, anti-diabetes, etc., when given parenterally, the compounds are administered generally in dosages of, for example, 0.5 to about 15 mg/kg/day, also depending upon the host and effect desired.

Obviously, other modifications and variations of the present invention are possible in light of the above teachings. It is, therefore, to be understood that changes may be made in the particular embodiments of this invention which are within the full intended scope of the invention as defined by the appended claims.

What is claimed is:

1. A process for inhibiting the enzyme G6PDH in a mammalian host which comprises administering to said host a compound in an amount effective to inhibit said G6PDH having the formula

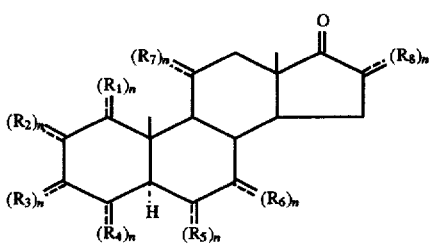

wherein $R_1$, $R_2$, $R_3$, $R_4$, $R_6$, $R_7$ and $R_8$ are independently selected from the group consisting of hydrogen, alkyl, alkenyl, alkynyl, halogen and hydroxyl; $R_5$ is hydrogen, alkyl, alkenyl, alkynyl or halogen, n is an integer from 1 to 2 inclusive with the proviso that when $R_1$–$R_8$ are alkenyl or alkynyl, n is 1, with the further proviso that said compounds are not 16α-halo-3βhydroxy 5α-androsten-17-one or 16α-Br-5-androstan-17-one.

2. The process according to claim 1 wherein said alkyl is lower alkyl having from 1 to 5 carbon atoms.

3. The process according to claim 1 wherein $R_3$ is hydroxy and $R_1$, $R_2$ and $R_4$ are hydrogen or alkyl.

4. The process according to claim 1 wherein $R_1$, $R_2$, $R_3$ and $R_4$ are selected from the group consisting of hydrogen and alkyl.

5. The process according to claim 1 wherein said compound has the formula:

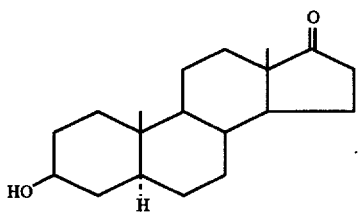

6. The process according to claim 1 wherein said compound has the formula:

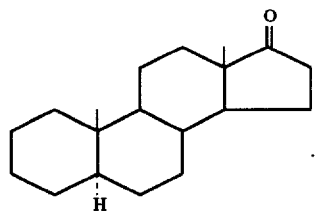

7. A process for inhibiting the enzyme G6PDH in a mammalian host which comprises administering to said host a compound in an amount effective to inhibit said G6PDH having the formula:

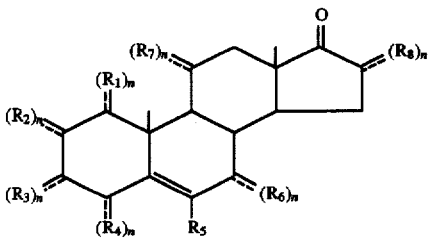

wherein $R_1$, $R_2$, $R_3$, $R_4$, $R_6$, and $R_7$ are each independently selected from the group consisting of hydrogen, alkyl, alkenyl, alkynyl, halogen and hydroxyl; $R_5$ is hydrogen, alkyl, alkenyl, alkynyl or halogen; $R_8$ is alkyl, alkenyl, alkynyl, halogen, or hydroxy; n is an integer from 1 to 2 inclusive with the proviso that when $R_1$, $R_2$, $R_3$, $R_4$, $R_5$, $R_6$, $R_7$ or $R_8$ is alkenyl or alkynyl, n is 1; and with the further proviso that said compound is not 3β-hydroxy-16α-bromo-5-androsten-17-one.

8. The process according to claim 7 wherein $R_3$ is hydroxy and $R_1$, $R_2$ and $R_4$ are hydrogen or alkyl.

9. The process according to claim 7 wherein said alkyl is lower alkyl having from 1 to 5 carbon atoms.

10. The process according to claim 7 wherein $R_1$, $R_2$, $R_3$ and $R_4$ are selected from the group consisting of hydrogen and alkyl.

11. A process for inhibiting the enzyme G6PDH in a mammalian host which comprises administering to said host a compound in an amount effective to inhibit said G6PDH having the formula:

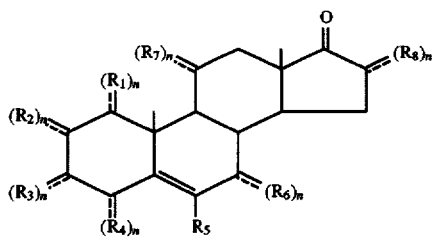

wherein $R_1$, $R_2$, $R_4$, $R_6$ and $R_7$ are each independently selected from the group consisting of hydrogen, alkyl, alkenyl, alkynyl, halogen and hydroxy;

$R_3$ is alkyl, alkenyl, alkynyl, or halogen;

$R_8$ is hydrogen, alkyl, alkenyl, alkynyl, halogen or hydroxy;

$R_5$ is hydrogen, alkyl, alkenyl, alkynyl or halogen; and n is an integer from 1 to 2 inclusive with the proviso that when $R_1$, $R_2$, $R_3$, $R_4$, $R_5$, $R_6$, $R_7$ or $R_8$ is alkenyl or alkynyl, n is 1.

12. The process according to claim 11 wherein $R_3$ is alkyl and $R_1$, $R_2$ and $R_4$ are hydrogen.

13. The process according to claim 11 wherein said compound has the formula:

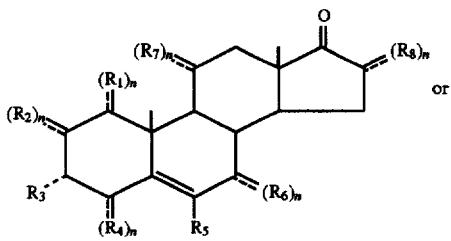

or

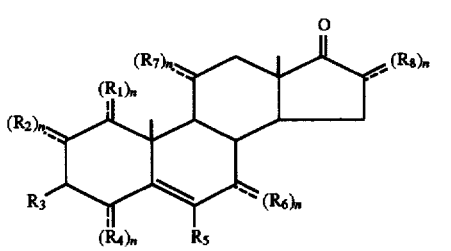

wherein $R_3$ is lower alkyl;

$R_1$, $R_2$, $R_4$, $R_5$, $R_6$ and $R_7$ are each independently hydrogen or lower alkyl;

$R_8$ is halogen, hydroxy, alkyl or hydrogen when it is in the α-position;

$R_8$ is lower alkyl or hydrogen when it is in the β-position; and n is 1 or 2.

14. The process according to claim 13 wherein $R_3$ is methyl.

15. The process according to claim 13 wherein the halogen is fluorine.

16. The process according to claim 13 wherein said alkyl is methyl.

17. The process according to claim 7 wherein said compound has the formula:

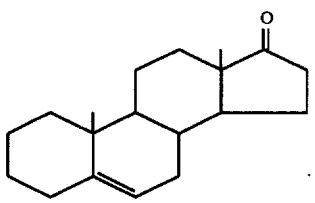

18. The process according to claim 11 wherein said compound has the formula:

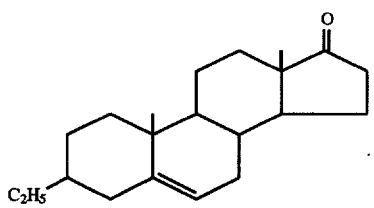

19. The process according to claim 11 wherein said compound has the formula:

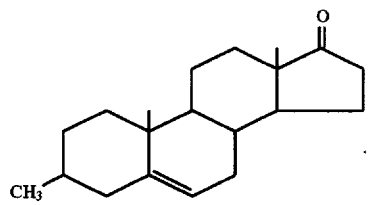

20. The process according to claim 11 wherein said compound has the formula:

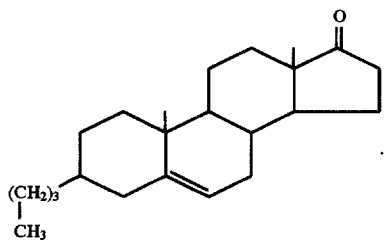

21. A process for inhibiting the enzyme G6PDH in a mammalian host which comprises administering to said host a compound in an amount effective to inhibit said G6PDH of the formula:

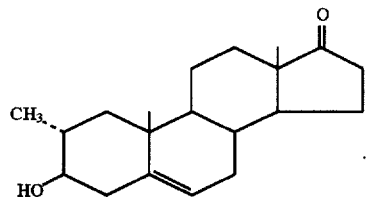

22. A process for the inhibiting the enzyme G6PDH in a mammalian host which comprises administering to said host a compound in an amount effective to inhibit said G6PDH of the formula:

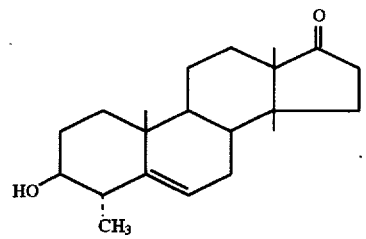

23. A process for inhibiting the enzyme G6PDH in a mammalian host which comprises administering to said host a compound in an amount effective to inhibit said G6PDH of the formula:

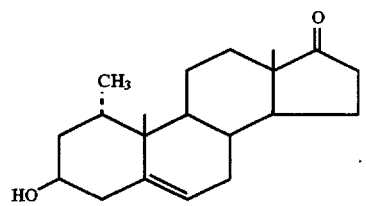

24. The process according to claim 14 wherein said compound has the formula:

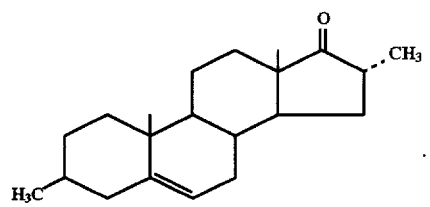

25. The process according to claim 14 wherein said compound has the formula:

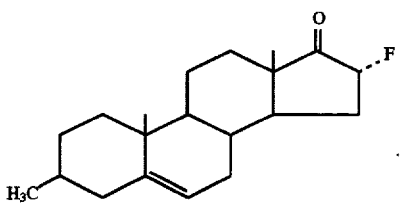

26. The process according to claim 14 wherein said compound has the formula:

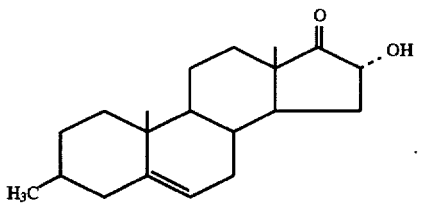

27. The process according to claim 11 wherein said compound has the formula:

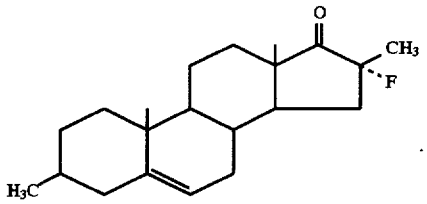

28. A process for the prophylaxis or treatment of hyperlipidemia said process comprising administering to a host an anti-hyperlipidemically effective amount of a compound having the formula:

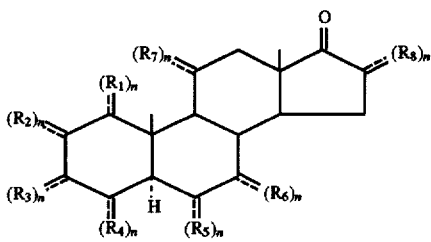

wherein $R_1$, $R_2$, $R_3$, $R_4$, $R_6$, $R_7$ or $R_8$ are selected from the group consisting of hydrogen, alkyl, alkenyl, alkynyl, halogen and hydroxyl, $R_5$ is hydrogen, alkyl, alkenyl, alkynyl or halogen, n is an integer from 1 to 2 inclusive with the proviso that when $R_1$–$R_8$ are alkenyl or alkynyl, n is 1.

29. The process of claim 28 wherein said alkyl is lower alkyl having from 1 to 5 carbon atoms.

30. The process according to claim 28 wherein $R_3$ is hydroxy and $R_1$, $R_2$, and $R_4$ are hydrogen or alkyl.

31. The process according to claim 28 wherein $R_1$, $R_2$, $R_3$ and $R_4$ are selected from the group consisting of hydrogen and alkyl.

32. The process according to claim 28 wherein said compound has the formula:

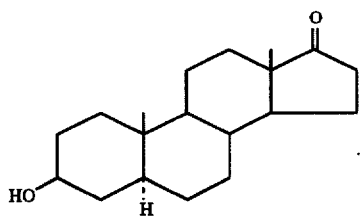

33. The process according to claim 28 wherein said compound has the formula:

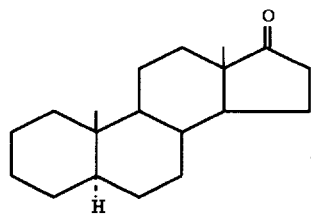

34. A process for the prophylaxis or treatment of hyperlipidemia said process comprising administering to a host an anti-hyperlipidemically effective amount of a compound having the formula:

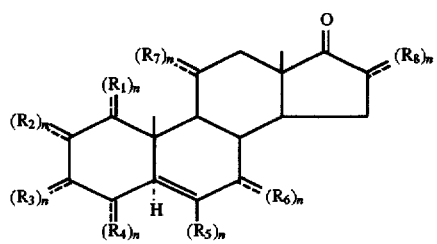

wherein
$R_1$, $R_2$, $R_3$, $R_4$, $R_6$, and $R_7$ are each independently selected from the group consisting of hydrogen, alkyl, alkenyl, alkynyl, halogen and hydroxy; $R_5$ is hydrogen, alkyl, alkenyl, alkynyl or halogen; $R_8$ is alkyl, alkenyl, alkynyl, halogen or hydroxy; n is an integer from 1 to 2 inclusive with the proviso that when $R_1$, $R_2$, $R_3$, $R_4$, $R_5$, $R_6$, $R_7$ or $R_8$ is alkenyl or alkynyl, n is 1.

35. A process for the prophylaxis or treatment of hyperlipidemia, said process comprising administering to a host an anti-hyperlipidemia effective amount of a compound having the formula:

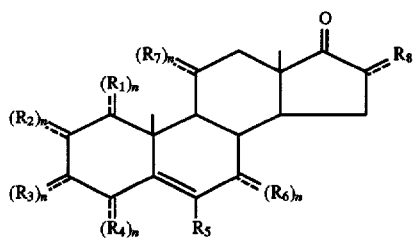

wherein
$R_1$, $R_2$, $R_4$, $R_6$, $R_7$ and $R_8$ are each independently selected from the group consisting of hydrogen, alkyl, alkenyl, alkynyl, halogen;
$R_5$ is hydrogen, alkyl, alkenyl, alkynyl or halogen;
$R_3$ is alkyl, alkenyl, alkynyl or halogen; and
n is an integer from 1 to 2 inclusive with the proviso that when $R_1$, $R_2$, $R_3$, $R_4$, $R_5$, $R_6$, $R_7$ or $R_8$ is alkenyl or alkynyl, n is 1.

36. The process according to claim 34 or 35 wherein said alkyl is lower alkyl having from 1 to 5 carbon atoms.

37. The process according to claim 34 wherein $R_1$, $R_2$, $R_3$ and $R_4$ are selected from the group consisting of hydrogen and alkyl.

38. The process according to claim 34 wherein $R_3$ is alkyl and $R_1$, $R_2$ and $R_4$ are hydrogen.

39. The process according to claim 34 wherein $R_3$ is hydroxy and $R_1$, $R_2$ and $R_4$ are hydrogen or alkyl.

40. The process according to claim 35 wherein said compound has the formula:

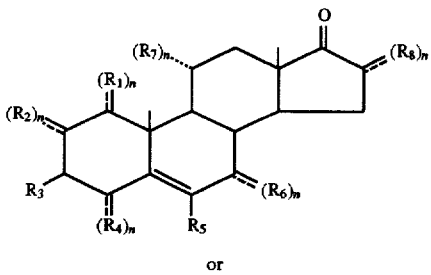

or

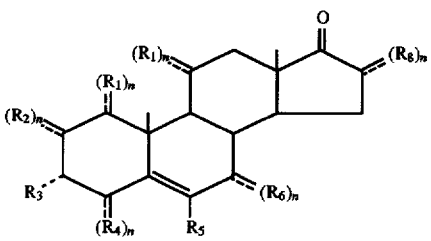

wherein $R_1$, $R_2$, $R_4$, $R_5$, $R_6$ and $R_7$ are each independently hydrogen or lower alkyl;

$R_3$ is lower alkyl;

$R_8$ is halogen, hydroxy, alkyl or hydrogen when it is in the α-position;

$R_8$ is lower alkyl or hydrogen when it is in the β-position; and n is 1 or 2.

41. The process according to claim 40 wherein $R_3$ is methyl.

42. The process according to claim 40 wherein halogen is fluorine.

43. The process according to claim 40 wherein said alkyl is methyl.

44. The process according to claim 34 wherein said compound has the formula:

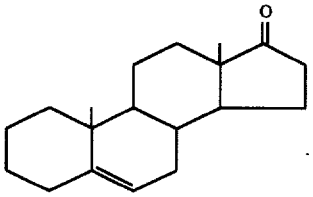

45. The process according to claim 35 wherein said compound has the formula:

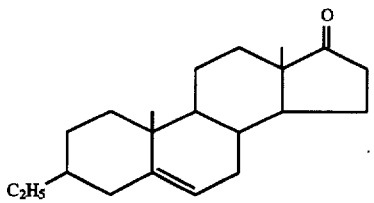

46. The process according to claim 35 wherein said compound has the formula:

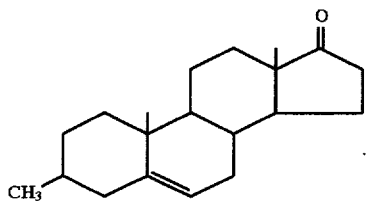

47. The process for the prophylaxis or treatment of hyperlipidemia, said process comprising administering to a host an anti-hyperlipidemically effective amount of a compound having the formula:

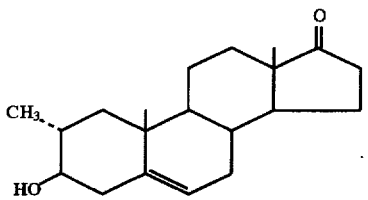

48. The process for the prophylaxis or treatment of hyperlipidemia, said process comprising administering to a host an anti-hyperlipidemically effective amount of a compound having the formula:

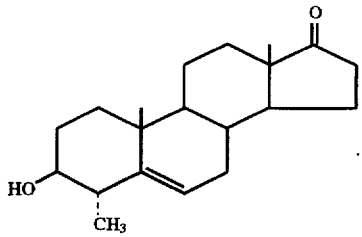

49. A process for the prophylaxis or treatment of hyperlipidemia, said process comprising administering to a host an anti-hyperlipidemically effective amount of a compound having the formula:

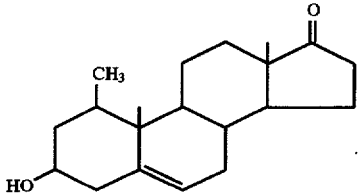

50. The process according to claim 41 wherein said compound has the formula:

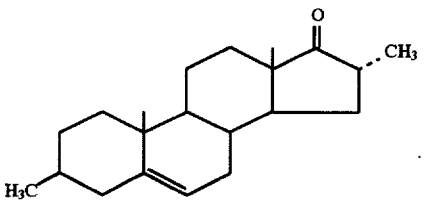

51. The process according to claim 41 wherein said compound has the formula:

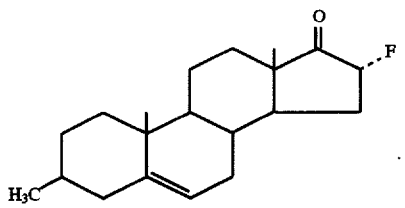

52. The process according to claim 41 wherein said compound has the formula:

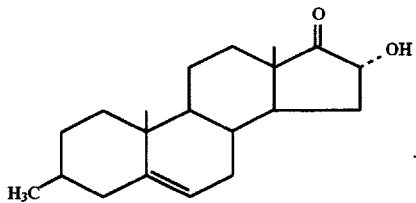

53. The process according to claim 41 wherein said compound has the formula:

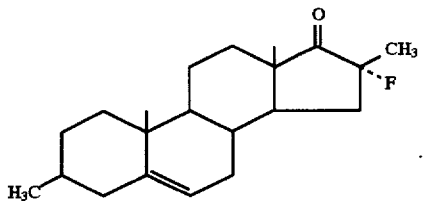

54. A process for the treatment of auto-immune disease, said process comprising administering to a host an anti-autoimmune effective amount of a compound of the formula:

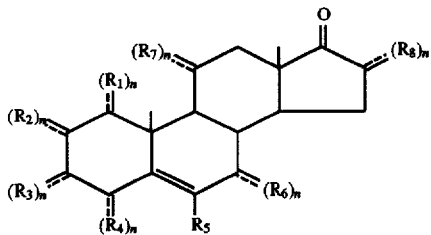

wherein, $R_8$ is alkyl, alkenyl, alkynyl, halogen or hydroxy;

$R_1$, $R_2$, $R_4$, $R_6$, $R_7$, and $R_8$ are each independently hydrogen, alkyl, alkenyl, alkynyl or halogen;

$R_5$ is hydrogen, alkyl, alkenyl, alkynyl or halogen;

$R_3$ is hydrogen, halogen, alkyl, alkenyl or alkynyl; and n is an integer from 1 to 2 inclusive with the proviso that when $R_1$, $R_2$, $R_3$, $R_4$, $R_5$, $R_6$, $R_7$ or $R_8$ are alkenyl or alkynyl, n is 1.

55. The process according to claim 54 wherein said disease is lupus erythematosis.

56. A process for the treatment of auto-immune disease, said process comprising administering to a host an anti-autoimmune effective amount of a compound of the formula:

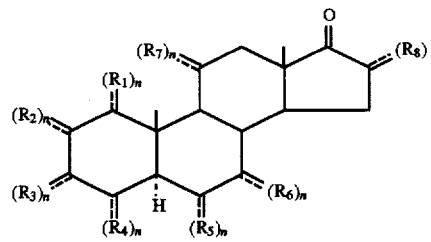

wherein, $R_1$, $R_2$, $R_4$, $R_6$ and $R_7$ are each independently hydrogen, alkyl, alkenyl, alkynyl or halogen;

$R_5$ is hydrogen, alkyl, alkenyl, alkynyl, or halogen;

$R_3$ is hydrogen, alkyl, alkenyl or alkynyl; and $R_8$ is halo, alkyl, alkenyl, alkynyl or hydroxy;

n is an integer from 1 to 2 inclusive with the proviso that when $R_1$, $R_2$, $R_3$, $R_4$, $R_5$, $R_6$, $R_7$ and $R_8$ are alkenyl or alkynyl, n is 1.

57. The process according to claim 58 wherein said disease is lupus erythematosis.

58. A process for the treatment of cancer selected from the group consisting of skin, breast, colon and lung cancer, said process comprising administering to a host an anti-cancer effective amount of a compound having the formula:

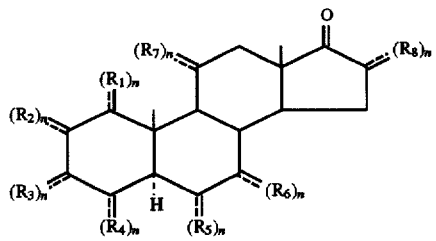

wherein $R_1$, $R_2$, $R_3$, $R_4$, $R_6$, $R_7$ and $R_8$ are each independently selected from the group consisting of hydrogen, alkyl, alkenyl, alkynyl, halogen and hydroxyl, $R_5$ is hydrogen, alkyl, alkenyl, alkynyl or halogen, n is an integer from 1 to 2 inclusive with the proviso that when $R_1$–$R_8$ are alkenyl or alkynyl, n is 1 and with the further proviso that said compounds are not 16α-halo-3β-hydroxy-5α-androstan-17-one or 16α-Br-5α-androstan-17-one.

59. The process according to claim 58 wherein said alkyl is lower alkyl having from 1 to 5 carbon atoms.

60. The process according to claim 58 wherein $R_3$ is hydroxy and $R_1$, $R_2$ and $R_4$ are hydrogen or alkyl.

61. The process according to claim 58 wherein $R_1$, $R_2$, $R_3$ and $R_4$ are independently selected from the group consisting of hydrogen and alkyl.

62. The process according to claim 58 wherein said compound has the formula:

63. The process according to claim 58 wherein said compound has the formula:

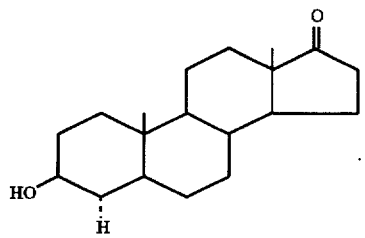

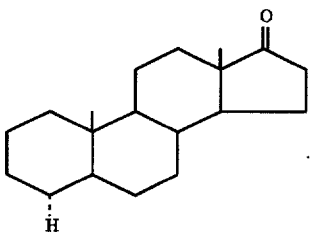

64. A process for the treatment of cancer selected from the group consisting of skin, breast, colon and lung cancer, said process comprising administering to a host an anti-cancer effective amount of a compound having the formula:

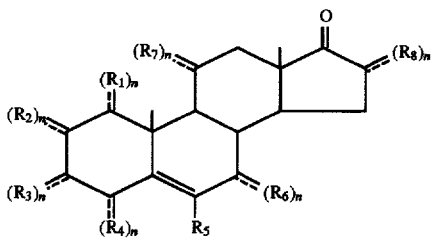

wherein $R_1$, $R_2$, $R_4$, $R_6$, $R_7$ and $R_8$ are each independently selected from the group consisting of hydrogen, alkyl, alkenyl, alkynyl, halogen and hydroxyl; $R_5$ is hydrogen, alkyl, alkenyl, alkynyl or halogen; $R_3$ is alkyl, alkenyl, alkynyl, halogen, or hydroxy; n is an integer from 1 to 2 inclusive with the proviso that when $R_1$, $R_2$, $R_3$, $R_4$, $R_5$, $R_6$, $R_7$ or $R_8$ is alkenyl or alkynyl, n is 1; and with the further provisos that $R_3$ may be hydroxyl only when any one of $R_1$, $R_2$, $R_4$, $R_5$, $R_6$, $R_7$ or $R_8$ is other than hydrogen and that said compound is not 3β-hydroxy-16α-bromo-5-androsten-17-one.

65. The process according to claim 64 wherein $R_3$ is hydroxy and $R_1$, $R_2$ and $R_4$ are hydrogen or alkyl.

66. The process according to claim 64 wherein said alkyl is lower alkyl having from 1 to 5 carbon atoms.

67. The process according to claim 64 wherein $R_1$, $R_2$, $R_3$ and $R_4$ are independently selected from the group consisting of hydrogen and alkyl.

68. The process according to claim 64 wherein $R_3$ is alkyl and $R_1$, $R_2$ and $R_4$ are hydrogen.

69. The process according to claim 64 wherein said compound has the formula:

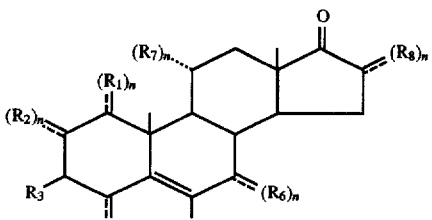

or

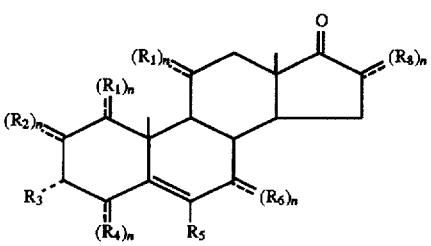

wherein $R_3$ is lower alkyl;

$R_1$, $R_2$, $R_4$, $R_5$, $R_6$ and $R_7$ are each independently hydrogen or lower alkyl;

$R_8$ is halogen, hydroxy, hydrogen or alkyl when it is in the α-position;

$R_8$ is lower alkyl or hydrogen when it is in the β-position; and n is 1 or 2.

70. The process according to claim 69 wherein $R_3$ is methyl.

71. The process according to claim 69 wherein halogen is fluorine.

72. The process according to claim 69 wherein $R_1$, $R_2$, $R_4$, $R_5$, $R_6$ and $R_7$ are hydrogen.

73. The process according to claim 64 wherein said compound has the formula:

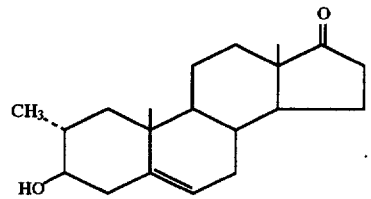

74. The process according to claim 64 wherein said compound has the formula:

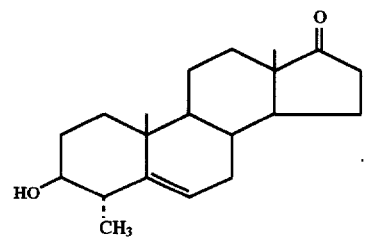

75. The process according to claim 64 wherein said compound has the formula:

76. The process according to claim 64 wherein said compound has the formula:

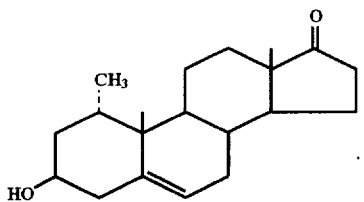

77. The process according to claim 69 wherein said compound has the formula:

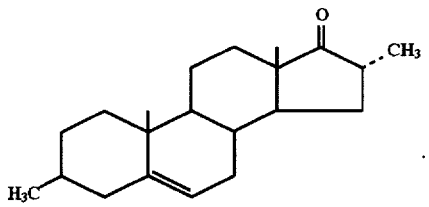

78. The process according to claim 69 wherein said compound has the formula:

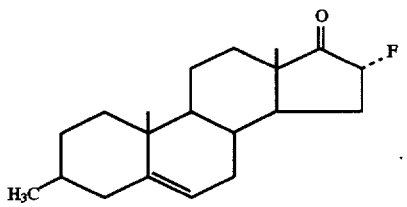

79. The process according to claim 69 wherein said compound has the formula:

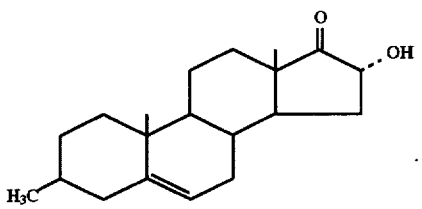

80. The process according to claim 1 wherein $R_3$ is hydrogen, alkyl, alkenyl, alkynyl or halogen.

81. The process according to claim 1 wherein $R_8$ is fluoro or chloro.

82. The process according to claim 1 wherein $R_1$, $R_2$, $R_4$, $R_5$, $R_6$ and $R_7$ are each independently hydrogen or lower alkyl;

$R_3$ is lower alkyl;

$R_8$ is halogen, hydroxy, hydrogen, or lower alkyl when it is in the α-position;

$R_8$ is halogen, hydrogen, or lower alkyl when it is in the β-position.

83. The process according to claim 82 wherein $R_1$, $R_2$, $R_4$, $R_5$, $R_6$ and $R_7$ are hydrogen.

84. The process according to claim 28 wherein $R_3$ is halogen, alkyl, alkenyl, or alkynyl.

85. The process according to claim 84 wherein $R_8$ is alkyl, halogen or hydroxy or hydrogen.

86. The process according to claim 28 wherein $R_3$ is alkyl, $R_1$, $R_2$, $R_4$, $R_5$, $R_6$ and $R_7$ are hydrogen or lower alkyl and $R_8$ is alkyl, halogen, hydroxy or hydrogen.

87. The process according to claim 86 wherein $R_3$ is lower alkyl.

88. A process for the treatment of cancer selected from the group consisting of skin, breast, colon and lung cancer, said process comprising administering to a host an anti-cancer effective amount of a compound having the formula:

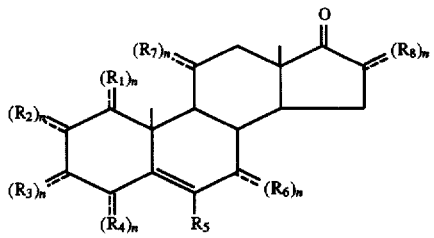

wherein $R_1$, $R_2$, $R_4$, $R_6$ and $R_7$ are each independently selected from the group consisting of hydrogen, alkyl, alkenyl, alkynyl, halogen and hydroxy;

$R_3$ is alkyl, alkenyl, alkynyl, halogen or hydrogen;

$R_8$ is alkyl, alkenyl, alkynyl or halogen or hydroxy;

$R_5$ is hydrogen, alkyl, alkenyl, alkynyl or halogen; and n is an integer from 1 to 2 inclusive with the proviso that when $R_1$, $R_2$, $R_3$, $R_4$, $R_5$, $R_6$, $R_7$ or $R_8$ is alkenyl or alkynyl, n is 1.

* * * * *

UNITED STATES PATENT AND TRADEMARK OFFICE
CERTIFICATE OF CORRECTION

PATENT NO.    : 5,714,481
DATED         : February 3, 1998
INVENTOR(S)   : Arthur Schwartz et al.

It is certified that error appears in the above-identified patent and that said Letters Patent is hereby corrected as shown below:

Title page,
Item [56], U.S. PATENT DOCUMENTS, after "3,976,691..." insert the following:
-- 3,983,144    Schwartz et al. . . . . . . . . . . . . . . 260/397.3 --

Column 19,
Line 34, "$^3$H" should read -- 3H --
Line 64, "1.3" should read -- (13) --

Column 20,
Line 18, "M$^+$, 100)" should read -- (M$^+$, 100) --
Line 36, "$C_{23}H360$" should read -- $C_{23}H_{36}O$ --
Line 42, "4β-methyl" should read -- 4α-methyl --

Column 21,
Line 36, "17β-o13" should read -- 17β-o1-3-one --

Column 25,
Line 52, "chloro,3β" should read -- chloro-3β --

Column 29,
Between structures in Column 29, insert title as follows:
-- Alkenylation and Alkynylation at Carbon-3 --

Column 33,
Line 47, "Depcotection" should read -- Deprotection --

Column 46,
Line 29, "2" should read -- 2d --

Column 48,
Line 4, "bcomide" should read -- bromide --

UNITED STATES PATENT AND TRADEMARK OFFICE
CERTIFICATE OF CORRECTION

PATENT NO. : 5,714,481
DATED : February 3, 1998
INVENTOR(S) : Arthur Schwartz et al.

It is certified that error appears in the above-identified patent and that said Letters Patent is hereby corrected as shown below:

Column 49,
Lines 44-50,

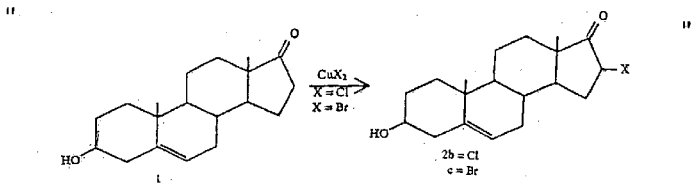

should read

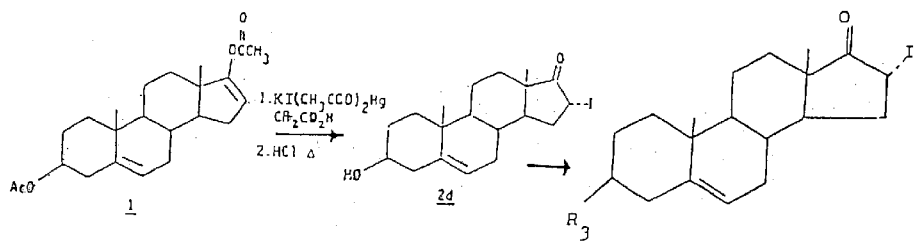

Column 61,
Line 26, "ethynyl-3β,17β-" should read -- ethynyl-3β,17α --
Line 66, "3β,16α-" should read -- 3β,16β --

Column 64,
Example VII, Formula: "$C_{19}H_{34}IFO$" should read -- $C_{19}H_{26}IFO$ --

Column 67,
Line 12, "(7963)" should read -- (1963) --

Column 69,
Line 53, "fop" should read -- for --

UNITED STATES PATENT AND TRADEMARK OFFICE
CERTIFICATE OF CORRECTION

PATENT NO.   : 5,714,481
DATED        : February 3, 1998
INVENTOR(S)  : Arthur Schwartz et al.

It is certified that error appears in the above-identified patent and that said Letters Patent is hereby corrected as shown below:

Column 75,
Per Cent Inhibition Formula 14, "10 $\mu$m 73" should read -- 10 $\mu$m 75 --

Column 77,
Formula 19, "$H_2C$" should read -- $H_3C$ --

Column 93,
Line 17, "level's" should read -- levels --

Column 95,
Line 5, "metablism" should read -- metabolism --
Line 9, "band" should read -- hand --

Column 104,
Lines 16-25,

"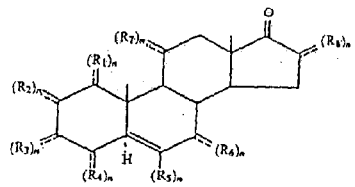"

should read

-- 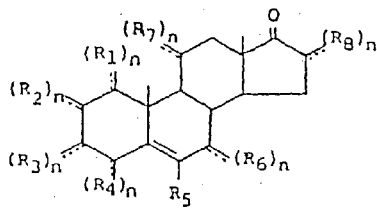 --

UNITED STATES PATENT AND TRADEMARK OFFICE
CERTIFICATE OF CORRECTION

PATENT NO.   : 5,714,481
DATED        : February 3, 1998
INVENTOR(S)  : Arthur Schwartz et al.

It is certified that error appears in the above-identified patent and that said Letters Patent is hereby corrected as shown below:

Column 110,
Lines 15-20,

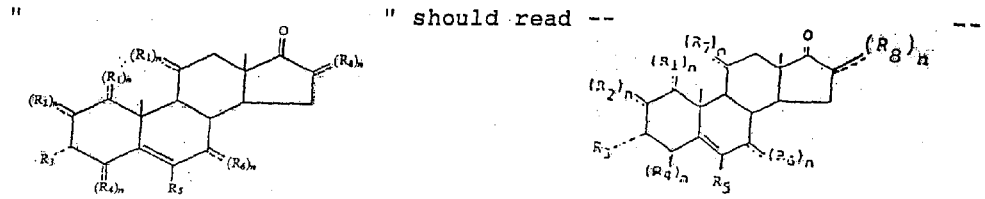

Signed and Sealed this

Twenty-fifth Day of November, 2003

JAMES E. ROGAN
*Director of the United States Patent and Trademark Office*